United States Patent
Will et al.

(10) Patent No.: US 11,116,221 B2
(45) Date of Patent: Sep. 14, 2021

(54) PEST CONTROL METHODS

(71) Applicants: Fraunhofer-Gesellschaft zur Foerderung der angewandten Forschung e.V, Munich (DE); Justus-Liebig-Universitaet Giessen, Giessen (DE)

(72) Inventors: Torsten Will, Giessen (DE); Andreas Vilcinskas, Fernwald (DE); Rainer Fischer, Aachen (DE)

(73) Assignees: FRAUNHOFER-GESELLSCHAFT ZUR FOERDERUNG DER ANGEWANDTEN FORSCHUNG E.V., Munich (DE); JUSTUS-LIEBIG-UNIVERSITAET GIESSEN, Giessen (DE)

( * ) Notice: Subject to any disclaimer, the term of this patent is extended or adjusted under 35 U.S.C. 154(b) by 1147 days.

(21) Appl. No.: 14/894,808

(22) PCT Filed: May 28, 2014

(86) PCT No.: PCT/EP2014/061084
§ 371 (c)(1),
(2) Date: Nov. 30, 2015

(87) PCT Pub. No.: WO2014/195209
PCT Pub. Date: Dec. 11, 2014

(65) Prior Publication Data
US 2016/0135466 A1 May 19, 2016

Related U.S. Application Data

(60) Provisional application No. 61/830,381, filed on Jun. 3, 2013.

(30) Foreign Application Priority Data

Jun. 3, 2013 (EP) .................................... 13170258

(51) Int. Cl.
| | | |
|---|---|---|
| *C12N 15/82* | (2006.01) | |
| *A01N 63/10* | (2020.01) | |
| *A01N 57/16* | (2006.01) | |
| *C07K 14/435* | (2006.01) | |
| *A01N 61/00* | (2006.01) | |
| *A01N 65/00* | (2009.01) | |

(52) U.S. Cl.
CPC ............ *A01N 57/16* (2013.01); *A01N 61/00* (2013.01); *A01N 63/10* (2020.01); *A01N 65/00* (2013.01); *C07K 14/43563* (2013.01); *C12N 15/8218* (2013.01); *C12N 15/8286* (2013.01); *Y02A 40/146* (2018.01)

(58) Field of Classification Search
None
See application file for complete search history.

(56) References Cited

PUBLICATIONS

GenBank AK342155 (published online Jun. 2009; see sequence appended to the restriction requirement).*
Mutti et al (Journal of Insect Science, 2006, 6(38): 1-7).*
Carolan et al (Proteomics, 2009, 9: 2457-2467).*
Pitino et al (PLoS One, 2011,6(10): e25709).*
PCT/EP2014/061084 International Search Report dated Jul. 24, 2014.
Mutti et al. "RNAi knockdown of a salivary transcript leading to lethality in the pas aphid, Acyrthosiphon pisum." Journal of Insect Science, Oct. 1, 2006, 6(38):1-7.
Pitino et al. "Silencing of Aphid Genes by dsRNA Feeding from Plants." PLOS ONE, Oct. 5, 2011, 6(10):e25709.
Rao et al. "Proteomic Profiling of Cereal Aphid Saliva Reveals Both Ubiquitous and Adaptive Secreted Proteins." PLOS ONE, Feb. 27, 2013, 8(2):e57413.
"Acyrthosiphon pisum ACYPI009881 mRNA, clone: 26G13, complete cds, full-insert cDNA sequence based on the ESTs (5'-EST:EX621355, 3'-EST:EX623288)." Sequence—Database Accession No. AK342155.1, Jun. 12, 2009.
"ID0AAH12AF07ZM1 ID0AAH Acyrthosiphon pisum cDNA clone ID0AAH12AF07 5', mRNA sequence." Sequence—Database Accession No. DV748157.1, Nov. 22, 2005.
"TSA: Acyrthosiphon pisum strain LSR1 Contig_82299.Acpicure mRNA sequence." Sequence—Database Accession No. HP323720.1, Sep. 27, 2010.
"Sitobion avenae isolate CGSA5 putative sheath protein (shp-1) mRNA, partial cds." Sequence—Database Accession No. JX417977.1, Oct. 3, 2012.
"Metopolophium dirhodum isolate CGMD3 putative sheath protein (shp-1) mRNA, partial cds." Sequence—Database Accession No. JX417978.1, Oct. 3, 2012.
Carolan et al. "The secreted salivary proteome of the pea aphid *Acyrthosiphon pisum* characterised by mass spectrometry." Proteomics, May 1, 2009, 9(9):2457-2467.
Bingsohn et al. "Knockdown of genes in the Toll pathway reveals new lethal RNA interference targets for insect pest control", Insect Molecular Biology, 2017, 26(1):92-102.
Huang et al. "Screening and Functional Analyses of Nilaparvata lugens Salivary Proteome", Journal of Proteome Research, 2016, 15:1883-1896.
Knorr et al. "Gene silencing in Tribolium castaneum as a tool for the targeted identification of candidate RNAi target in crop pests", Scientific Reports, Feb. 1, 2018, 8:2061.

(Continued)

*Primary Examiner* — Stephen Uyeno
(74) *Attorney, Agent, or Firm* — Wagenknecht IP Law Group PC

(57) ABSTRACT

The technology provided herein relates to methods of multi-species insect pest control by incorporating an inhibitor against the structural sheath protein (SHP) into the body of an agricultural target pest, and to pest control agents to be used in the method and to transgenic crop, greenhouse and ornamental plants.

7 Claims, 12 Drawing Sheets

Specification includes a Sequence Listing.

(56) References Cited

PUBLICATIONS

Rinkevich & Scott "Limitations of RNAi of a6 nicotinic acetylcholine receptor subunits for assessing the in vivo sensitivity to spinosad", Insect Science, 2013, 20:101-108.

Zha et al. "Knockdown of Midgut Genes by dsRNA-Transgenic Plant-Mediated RNA Interference in the Hemipteran Insect Nilaparvata lugens", PLOS ONE, May 31, 2011, 6(5):e20504.

* cited by examiner

Figure 6

**Part of the mRNA sequence encoding *Acyrthosiphon pisum* SHP (SEQ ID NO.1)**

```
GATATAATGATTTCCATTTTAAGACTATGATATTTAGTTTTAAACCTGTTTTTAGGAATTGGAGAGTTAGATAAAACAAAAAT
CGGATTATTCAATACTGAGTAGATCATTAAATAATAGAATTCGTGAAAATAGCCAGTCCATACAATGGATAGTAGCCTAATTA
TTACTCTTTACTGTAGTATCTATACTCTGTTCAAAATGAGATCATTACTGCGCGGCGACCAGTTTTCGTCGGGCGGCGGTCAG
ACGCCGTCCCCACTACGGCGACGCGTTGGGCACTGCCACGGAACAAAGCCACGCCCATGCGCACAACTAGGCCGCCGAAATCA
ACTTTCAGTTCGTCTTGTTGGGAACCGGTCAAAGGCAACTAACAGGATGAGGTCTGTACTGATTCTTTGCGTTATTATTGCTG
CTGCTGTGGCATGCCCAGTATCAAAAACAAAAGATTGCTCTTGCGGTCTGCCTAAAATATGTCCTTCAACGTGGAAAATTAAG
ACATTTGATTCCCAATGCGAAACATTAGCATTCCAAGGAACATGGTTTTTACAAATGGCAACACCAACATACATTGACCAGCA
AAACCCATTAAAAACCGGGCTGTTCTGTAACAGTTATCCTTGTACCAACAATCAACTGATATTTAAGGATACCACACCATGTG
ATGATACCGATTACAACACTGAATACGAAGTGATTGATTCGTCATACAATATCTATACCCAATGTACAGAAACCCAAATAGCA
TTATTATGCCCAGCGTATGGCAGTTCCAGCAAATATGCAATCTTTAATGTCGGTTCAGAAAAATATTATACAAACCCAATTGC
CGAAAAATATCCATTTGTTGACAAGGATTTATTCAGACATAAGATCGGCCAGGGTAGCTGTGAGAGAGAATACACAGTCGCTG
TAATCGGTGCTGATGACTGTTGGAAAGAGTATATGGTGTTAGTCGTTATTAACCAGTATGACAACTTCTTTGGCGGAGATGAG
TATATTACTTGGGTATTGACAAGAGATGTTAACCCTGATTGGAGTACTTATGATAAAGCATACAATGATATTAAGGGAAGTGG
TCTCTGCCCTAACTATTTGGTAAGTGTTGATCATTCGTTTGAATCAATGACAGGACCTTCAATGGCAGTACCTTCAATGGCAC
CAAGTGTGGCAGTACCTTCAATGGCACCAACTATGCCTGGTGATGTCGATAGTATGGTACAAAAAACGTCTGTCTCTACAACA
TCAGCAACAAAATCAATTAGTACCGACTGTGGTAGTACTGTAACTTCATCATCCACTTCAACAACTACGACATCGACTGTGAT
AATTGATAAAAGCTCAGATTTCTCTAGTATTTATGACATCGGACCGTGTGATTTATACAGTCCATACGAGGGTCTCCAAATCT
ACAAAAACCTGGATAAAGAAACAATTAGACGTGCCTTTTCTGGAAATTATTACATGACCCAAGCTACACCTTGTTCGTTTTAC
GATACCCCCAAATCAAAAGTAGGATTATTAAATACGTGTTTCCCTGCATGCGGTATGCAACTCTGTTTTGATGATGCATCAAT
TGACGATTGGGATTGCAATACTCCTCGTATGGTTATGGATCGTGGTTACAATATGAGGACCGGTGAAGTGCATATGACGAGAA
GCTATATTTCTTCAGCCTATTCTGACGACCATCCATTTGGTACTGTCACGTATGCATTCCATTCTGAGGGATATTATGATGTA
CCAATTGATGAAACAGATTGCCTACCATTAGATGGATTGATTTGCAAACCACCCTCAGATATATACAAGAACCAAATCATAGC
AAATATTATTGGATACAAAGACAATGATTACTTAATGTTTTGCATTGCAAACCGATACAAGAACCCGCTCTTTCCAAAAAAGC
AAGTACCTCTAGTCTATTGTTATACCAGAGAAAGAATACCAAGTCAGGATACTATGAATAGTATCACACAAGAAATGTTGCGT
TGTGGACTTAACCCAAATTACTTGATGAAAATTGATCAGTCGAAAACAATTGAGGAAGTATTTACGTTTGATAAAACTTATTA
TGAATCAACAGTGACCAGTACATCTACGACCAAAAGTGTGGTTTCCACACGTGGACTCAGCATTGGAAGCTCTCCCCTTCAAG
GATTACCTTCAATATGTCCACCAGACTGGAACGTTAAAACTTTTGACAATCAATACGCTACCATTGCATTCCAAGGAATATGG
AATGTACAAATGACTACACCAACATATATAAATGGAAACAACCCATTAAAAACCGGGCTATTCTGTAACAGTTATCCTTGTAC
CAACAATCAACTGATATTTAAGGATACCACACCATGTGATGATACCGATTACAACACTGAATATGAAATGACTGATTCATCAT
ACAATCTCTATACCCAGTGCACAGAAACCCAAAAAGCATTATTATGCCCAGCGTATGGCAGTTGCAGCCAATATGCAATCTTT
AACGTCGGTTCAGAAAAATATTATAATACTGCGATCATCGAAAAATATCCATTTATTGACAAGGATTTATTCAGGCATAAGAT
TGTCCAGGGTACCTGTGAGAGAGAATACACAGTCGCTGTAATCGGTGCTGATGACTGTTGGGAAGAGTATATGGTGTTAGCTG
TTATCAACCAGTATGATAACGTATTTGGCGGAAATAAGTATATTATTTGGGTAGTGACGAGAGATGCTAACCCTAAATGGAGT
ACTTATAAGAAAGCATACGAAGACATTGAGAGAAGTGGTCTCTGCCCTAACTATTTGGTAAGTGTTGATCATTCGTTGGAATC
AATGACAGGACCTTCAATGGCACCAAGTGTGGCAGTACCTTCAATTGCACCAACTATGCCTGGTGATGTTGATAGCATGGTAC
AAAAAACATCTGTCTCTACAACATCAGCAACAAAATCAATTAGTACCGACTGCGGTAGTACTGTAACTTCGTCATCCACTTCA
ACAACTACGACATCGACTGTGATAATTGATAAAAGCTCAGATTTCTCTAGCCTGTATGAGCTCGGACAGTGTGATTTATACAA
AGATATCCAAATCTACAAAAACCTGGATAAAGAAACAATTAGACGTGCCTTGTCTGGAAAATATTACATGACCCAAGCTACAC
CTTGTTCGTATTACAATAGCCCAAATTCGAGAGTCGGTATTTTAAATACGTGTTTCCCTGCATGCGGTATGCAACTCTGTTTT
GATGATACGTCAATTGATGATTGGGATTGCAATACTCCTCGTATGGTTATGGATCGTGGTTACGATATGAGGACCGGTGAAGT
GCAATTGACGAGAAGTTATATTTCTTCAGTCTATTCTGACGACCATCCATTTGGTACTGTCACGTATGCATTCCATTCTGAAG
GATATTATGAGGGACCAATTGATGAAATGGATTGTCTACCATTAGATGGAATGATTTGCAAACCACCCTCAGATATATACAAG
AACCAAATCATAGCAAGTATTATTGGATACAAAGACAATGATTACTTAATATTTTGCATTGCAAACAAATACAAGAACCCGCT
CTTTAGTTCGACACCAGTAAACCAAGTCATTGCTTATACAAGGGAGAGAGTTCCAAGCAAGGAAACTATAAAATCTATGACTC
AAGAATTATTGCAATGTGGTTATAATCCAAATTATTTGATCAAAATAGATCAGACTATGTATATGGATGATGATTACGTATTT
GAAAGTTCATATTATGAATCACAAACTTCATGTTGGAGTAGTAGTAGCAGTAGTTGTAGTAGCAGCACGAGTAGTTCAACTAC
TATTTCATCTTCGTCGAGTTCGTCTGTTAGCATTTCGTGTGATTAATTCATTTAAAACAATATAATATAATATGTCATTACAG
TCAGTTTAATAAATAAATAAAAATATCATGCATTATTATTTTGTGTTATATTTTTATTGTCTATCCGTGGCCAGCTTTCTTTA
AGTGAATAGGTTTTACAATGACACAAAAATCATTACGATATTTAATACTAAAAGTGGTTACTTACTTGTAGATAAATTGATAG
AAACTTGAAACATTACCCTATTATGACTCTTTCATTGAACAATAAATGTATTGGTTTATAACG

Figure 7

**Ribonucleic acid sequence of a dsRNA (SEQ ID NO.2) derived from SEQ ID NO. 1 for *Acyrhtosiphon pisum* pest control *in vitro* and *in planta***

```
GCGTTATTATTGCTGCTGCTGTGGCATGCCCAGTATCAAAAACAAAAGATT

PEST CONTROL METHODS

CROSS-REFERENCE TO RELATED APPLICATIONS

This application is a U.S. National stage of PCT/EP2014/061084 filed on May 28, 2014, which claims priority from U.S. Provisional Application Ser. No. 61/830,381 filed on Jun. 3, 2013 and EP Application Serial No. 13170258.1 filed on Jun. 3, 2013, each of which is incorporated herein by reference in its entirety.

REFERENCE TO SEQUENCE LISTING SUBMITTED ELECTRONICALLY

The official copy of the sequence listing is submitted electronically via EFS-Web as an ASCII formatted sequence listing with file "PCT_EP2014_061084_SEQID" created on 27 Nov. 2015 and having a size of 39 Kilobytes. The sequence listing contained in this ASCII formatted document forms part of the specification and is herein incorporated by reference in its entirety.

FIELD OF THE DISCLOSURE

The technology provided herein relates to methods of multi-species insect pest control by incorporating an inhibitor against the structural sheath protein (SHP) into the body of an agricultural target pest, and to pest control agents to be used in the method and to transgenic crop, greenhouse and ornamental plants.

BACKGROUND

The environment in which humans live is replete with pest infestation. Pests including insects, arachnids, crustaceans, fungi, bacteria, viruses, nematodes, flatworms, roundworms, pinworms, hookworms, tapeworms, trypanosomes, schistosomes, botflies, fleas, ticks, mites, and lice and the like are pervasive in the human environment. For example, insects of the order Hemiptera including aphids are significant pests of crops and garden plants as well as ornamentals.

In whole Europe, direct damage only by aphids is responsible for mean annual losses of 700,000 t of wheat, 850,000 t of potatoes and 2,000,000 t of sugar beet (Wellings P W et al., 1989). In the USA, annual direct yield losses in wheat and barley production, through reduced yields and pesticide treatment, peaked at $274 million in 1988 and dropped to less than $10 million by 1993 (Dedryver C-A et al., 2010). In the UK direct yield losses from aphids is 8-16% in pea, 10-13% in wheat and 5% in potato (Tatchell G M, 1989). In this context, virus transmission, e.g. the barley yellow dwarf virus or potato leaf roll virus; represents an important factor.

For aphid control, chemical agents as e.g. Imidacloprid and Dimethoat are used in conventional plant production while for biological plant production Azadirachtin from the Neem tree is applied (http://www.profiflor.de/index.htm). A further approach in aphid control is the use of beneficial insects (hoverfly, ladybeetle, brown lacewing) but this approach is only suitable for greenhouse cultures and can lead to the manifestation of invasive species. However, the use of insecticides is the most important control mechanism for aphids but the number of accredited insecticides was reduced during the last years due to potentially negative influences on the environment. An additional problem with insecticides is the fact that beside a variety of other insect species, aphids were shown to develop resistances. While the melon and cotton aphid *Aphis gossypii* actually shows resistances to 41 active compounds the green peach aphid *Myzus persicae* already developed resistances against 74 compounds (http://www.pesticideresistance.com/). Insecticide resistances can already occur after one generation and were reported in different aphid species and populations all over the world.

To prevent negative environmental effects of insecticides and to decrease the risk of resistance development, the strategy of integrated pest management (IPS) was developed to minimize the amount of applied pesticides (insecticides and herbicides). IPS is for example obligate for agriculture in Germany in accordance to the "Gute fachliche Praxis" and charges the use of biological, biotechnical and plant breeding approaches as well as agricultural culture methods. IPS is declared by the United Nations as general principle for plant protection.

To reduce the amount of insecticides, new biotechnical approaches are developed in accordance with IPS to control pests in agriculture. One of these approaches is the use of RNA interference. With regard to aphids, RNAi-mediated gene silencing was achieved in a number of publications by injection of dsRNA or siRNAs into the hemolymph (Mutti N S et al., 2006; Jaubert-Possamai S et al., 2007) or artificial feeding of dsRNA (Shakesby A J et al., 2009; Whyard S et al., 2009).

The very first proof of concept for transgenic plants that deliver highly specific dsRNA to their aphid hosts was conducted by Pitino M et al. (2011). The authors selected rack1 (gut located) and c002 (salivary gland located) as two different gene targets for the green peach aphid *Myzus persicae*. Two different plants, *Nicotiana benthamiana* and *Arabidopsis thaliana*, were transformed for each target and a silencing effect in aphids of up to 60% was observed on respective GM plant species. As a consequence of gene silencing the authors described for both genes a reduced fecundity. Surprisingly, silencing of C002 did not influence survival as previously observed for in vitro experiments with the pea aphid *Acyrthosiphon pisum* (Mutti N S et al., 2006). The authors suggest that this discrepancy is related to the different species.

Because most plants are infested by more than one pest species an approach is needed whose efficiency does not differ between different species.

Therefore, the availability of improved pest control methods for numerousness pest species would be highly advantageous.

SUMMARY OF THE DISCLOSURE

The present disclosure pertains to multi-species pest control methods comprising incorporating an inhibitor against the structural sheath protein (SHP) into the body of an agricultural target pest expressing SHP, a protein, which is present in a wide range of Hemiptera species.

The present disclosure pertains in particular two methods of RNAi mediated silencing of the sheath protein SHP for control of plant sucking insects of the order Hemiptera, in particular of the groups Sternorryhncha and Fulgoromorpha in agriculture.

In a first aspect, embodiments of the disclosure provide novel pest control methods comprising incorporating an inhibitor against the structural sheath protein (SHP) into the body of an agricultural target pest.

In a second aspect, embodiments of this disclosure relate to isolated polynucleotides selected from the group consisting of:

a) a polynucleotide comprising a nucleic acid sequence selected from the group consisting of SEQ ID NO:1, SEQ ID NO:5 and SEQ ID NO:7;
b) a polynucleotide that hybridizes to a nucleic acid sequence selected from the group consisting of SEQ ID NO:1, SEQ ID NO:5 and SEQ ID NO:7 under stringent conditions;
c) a polynucleotide of at least 70, at least 80, at least 85, at least 90 percent sequence identity, to a nucleic acid sequence selected from the group consisting of SEQ ID NO:1, SEQ ID NO:5 and SEQ ID NO:7;
d) a fragment of at least 16 contiguous nucleotides of a nucleic acid sequence selected from the group consisting of SEQ ID NO:1, SEQ ID NO:5 and SEQ ID NO:7; and
e) a complement of the sequence of (a), (b), (c) or (d), wherein ingestion by a Hemiptera crop, greenhouse and/or ornamental plant pest of a double stranded ribonucleotide sequence comprising at least one strand that is complementary to said polynucleotide or said fragment reduce feeding of said pest.

In a third aspect, embodiments of this disclosure relate to double stranded ribonucleotide sequences produced from the expression of a polynucleotide according to the present disclosure, wherein ingestion of said ribonucleotide sequences by a Hemiptera crop plant pest reduces feeding of said pest.

In a fourth aspect, embodiments of this disclosure provide vectors or expression systems comprising a nucleic acid molecule according to the second aspect and to cells transformed, transduced or transfected with said vector.

In a fifth aspect, some embodiments of this disclosure relate to plants transformed with a polynucleotide according to the present disclosure, or a seed thereof comprising said polynucleotide.

Further, some embodiments pertain to commodity products produced from a plant according to the fifth aspect, wherein said commodity product comprises a detectable amount of a polynucleotide according to the second aspect or a ribonucleotide expressed therefrom.

In a sixth aspect, some embodiments provide methods for controlling Hemiptera pest infestation comprising providing in the diet of a Hemiptera pest an agent comprising a first polynucleotide sequence that functions upon ingestion by the pest to inhibit a biological function within said pest, wherein said polynucleotide sequence exhibits from about 95 to about 100 percent nucleotide sequence identity along at least from about 16 to about 25 contiguous nucleotides to a SHP coding sequence derived from said pest and is hybridized to a second polynucleotide sequence that is complementary to said first polynucleotide sequence, and wherein said coding sequence derived from said pest comprise a sequence selected from the group consisting of SEQ ID NO:1, SEQ ID NO:5 and SEQ ID NO:7 or a complement thereof.

Further, in a seventh aspect, embodiments of the present disclosure pertains to methods for controlling a Hemiptera pest a plant cell expressing a polynucleotide sequence according to the present disclosure, wherein the polynucleotide is expressed to produce a double stranded ribonucleic acid, wherein said double stranded ribonucleotide acid and/or a RNAi inducing compound derived from said double stranded ribonucleotide acid functions upon ingestion by the pest to inhibit the expression of a SHP encoding target sequence within said pest and results in decreased feeding on said diet relative to a diet lacking the plant cell.

Further, in an eight aspect, embodiments of the present disclosure pertains to method for improving the yield of a crop produced from a crop plant subjected to insect pest infestation, said method comprising the steps of,
a) introducing a polynucleotide according to the present disclosure into said crop plant,
b) cultivating the crop plant to allow the expression of said polynucleotide, wherein expression of the polynucleotide inhibits feeding by insects pests and loss of yield due to pest infestation.

In a further aspect, the present disclosure relates to transgenic plant comprising a gene coding an inhibitor against SHP of a target pest.

Before the disclosure is described in detail, it is to be understood that this disclosure is not limited to the particular component parts of the process steps of the methods described. It is also to be understood that the terminology used herein is for purposes of describing particular embodiments only, and is not intended to be limiting. It must be noted that, as used in the specification and the appended claims, the singular forms "a," "an" and "the" include singular and/or plural referents unless the context clearly dictates otherwise. It is moreover to be understood that, in case parameter ranges are given which are delimited by numeric values, the ranges are deemed to include these limitation values.

BRIEF DESCRIPTION OF THE DRAWINGS

FIG. 6 is a nucleic acid sequence showing a part of the mRNA sequence coding for the *A. pisum* SHP (SEQ ID NO. 1).

FIG. 7 displays a ribonucleic acid sequence of a dsRNA (SEQ ID NO. 2) derived from SEQ ID NO. 1 exemplarily used for *Acyrhtosiphon pisum* pest control in vitro and in planta

Figure 1:
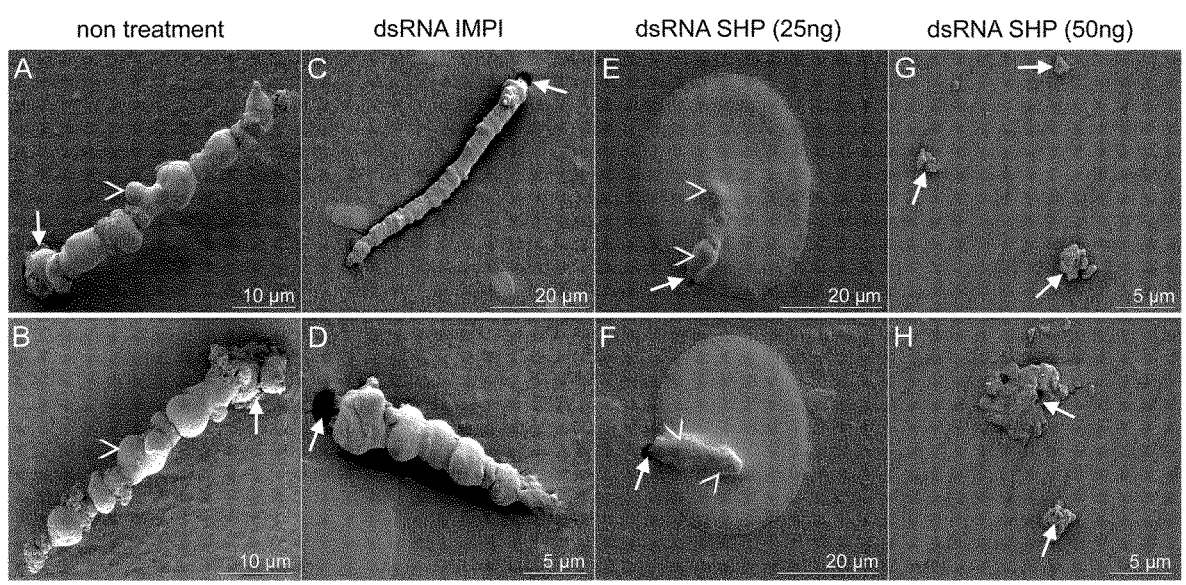
FIG. 1 represents electron microscopy pictures showing the Influence of SHP silencing on sheath formation.

controls for two weeks and on artificial diet for two days show a typical necklace structure (compare FIG. 1). (c) Formation of salivary sheaths from aphids feeding for two weeks on shp-dsRNA plant line L26 is disrupted in artificial diet.

Figure 11:
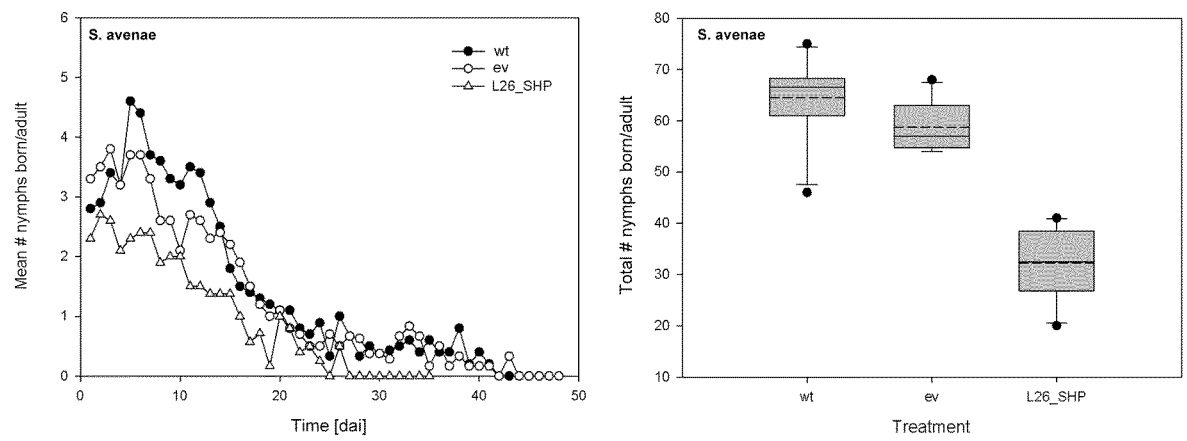

FIG. 11 are diagrams showing the reproduction of aphids from the species Sitobion avenae feeding during infestation on control (wt—wild type; ev—empty vector) and shp-dsRNA expressing plants respectively. Each group contained 15 aphids. (Left) The SHP RNAi aphids show a lower reproduction rate and a shorter overall duration of reproduction than aphids feeding on control plant lines. (Right) The total reproduction of the SHP RNAi aphids is significantly lower than that of the control groups.

Figure 12:
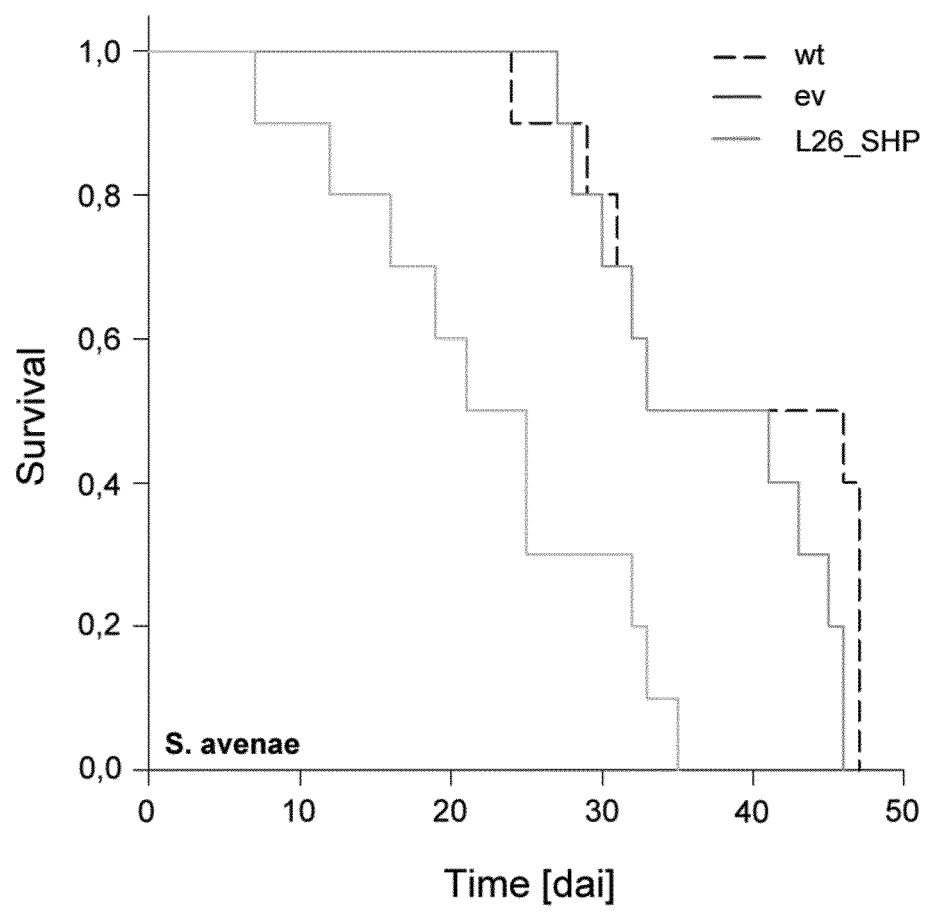

FIG. 12 is a diagram showing the survival of aphids (given as dai—days after infestation) from the species Sitobion avenae feeding on control (wt—wild type; ev—empty vector) and shp-dsRNA expressing plants. Survival analysis was done by Kaplan Meier Log-Rank. Each group contained 15 aphids. Aphids feeding on shp-dsRNA expressing plants did not show reduced survival when compared with controls.

DETAILED DESCRIPTION OF THE DISCLOSURE

Disclosed herein do novel pest control methods comprise the incorporation of an inhibitor against the structural sheath protein (SHP) into the body of an agricultural target pest, in particular against insect pests belonging to the order Hemiptera like aphids, and to pest control agents to be used in the method and to transgenic crop, greenhouse and ornamental plants.

Furthermore, the present disclosure provides methods and compositions for genetic control of pest infestations. For example, the present disclosure provides recombinant DNA technologies to post-transcriptionally repress or inhibit expression of a target structural sheath protein (SHP) coding sequence in the cell of a pest to provide a pest-protective effect by feeding to the pest one or more double stranded RNA (dsRNA) and/or small interfering ribonucleic acid (siRNA) molecules transcribed from all or a portion of a target coding sequence, thereby controlling the infestation. Therefore, the present disclosure relates to sequence-specific inhibition of expression of SHP coding sequences using double-stranded RNA (dsRNA), including small interfering RNA (siRNA), to achieve the intended levels of pest control.

Isolated and substantially purified nucleic acid molecules including but not limited to non-naturally occurring nucleotide sequences and recombinant DNA constructs for transcribing dsRNA molecules of the present disclosure are provided that suppress or inhibit the expression of target coding sequence for the structural sheath protein (SHP) in the pest when introduced thereto. Transgenic plants that (a) contain nucleotide sequences encoding the isolated and substantially purified nucleic acid molecules and the non-naturally occurring recombinant DNA constructs for transcribing the dsRNA molecules for controlling plant pest infestations, and (b) display resistance and/or enhanced tolerance to the insect infestations, are also provided. Compositions containing the dsRNA nucleotide sequences of the present disclosure for use in topical applications onto plants or onto animals or into the environment of an animal to achieve the elimination or reduction of pest infestation are also described.

Surprisingly, the inventors found that inhibiting SHP is a universally applicable form of pest control. For example, the generation of transgenic plants expressing dsRNA targeted at the SHP in specific insect pests is an efficient and environmentally sustainable approach to reduce the impact of insect pests on agriculture.

SHP is responsible for hardening of the salivary sheath, a protein structure that is formed out of gel saliva that is secreted during stylet movement through the plant tissue (Tjallingii and Hogen Esch, 1993). The inventors approach was based on their findings that salivary sheath were shown for a numerousness pest species, in particular for a wide range of species belonging to the order Hemiptera like aphids. For example, salivary sheath were shown for all aphid species studied so far and sequences with a close similarity are present in M. persicae EST database (EST accessions EC387934, EC388457 and EE572212 (http://www.ncbi.nlm.nih.gov/)). High sequence overlaps of mRNA (RefSeq XM_001943863 (http://www.ncbi.nlm.nih.gov/)) of 99% were reported for the species Sitobion avenae and Metopolophium dirhodum (Rao S A K (2011) "The identification and characterization of salivary proteins from the cereal aphids Sitobion avenae, Metopolophium dirhodum and Rhopalosiphum padi", PhD thesis, University College Dublin, Ireland).

Beside aphids, formation of a sheath-like structure could also be observed for other groups of insects belonging to the order Hemiptera including Sternorrhyncha such as whiteflies (Freeman et al., 2001) and for planthoppers (Fulgoromorpha) (Brentassi et al., 2007). The two sister groups Sternorryhncha and Fulgoromorpha show an overlap of protein sequence of the SHP protein that potentially originates from a common ancestor.

The inventor identified that that silencing of SHP in the insects, for example induced by injection of specific double stranded RNA, prevents sheath hardening. This leads to later and reduced feeding and a significantly reduced reproduction rate (−50%) in comparison to control groups. It can be assumed that reduced feeding will decrease negative influences on plant development due to reduced removal of nutrition by the insects, in particular by aphids. In addition reduced feeding will lower the risk of infection of aphid transmitted plant viruses like the barley yellow dwarf virus. Reduced reproduction will also lead to a slow population growth that makes for example single aphids easier to access to predators, e.g. ladybeetles.

The results according to the present disclosure indicate that a nucleotide sequence, either DNA or RNA coding for SHP can be used to construct plant cells resistant to infestation by the pest. The pest host, for example, can be transformed to contain one or more of SHP encoding nucleotide sequences. The nucleotide sequence transformed into the pest host or symbiont may encode one or more RNAs that form into a dsRNA sequence in the cells or biological fluids within the transformed host or symbiont, thus making the dsRNA available in the diet of the pest if/when the pest feeds upon the transgenic host or symbiont, resulting in the suppression of expression of SHP in the cells of the pest and ultimately the death, stunting, or other inhibition of the pest.

Post-transcriptional gene silencing may be used to downregulate the expression of the SHP coding gene. The gene silencing can be achieved e.g. by antisense molecules or molecules that mediate RNA interference.

Antisense polynucleotides are designed to specifically bind to RNA, resulting in the formation of RNA-DNA or RNA-RNA hybrids, with an arrest of reverse transcription or messenger RNA translation. Many forms of antisense have been developed and can be broadly categorized into enzyme-dependent antisense or steric blocking antisense.

Enzyme-dependent antisense includes forms dependent on RNase H activity to degrade target mRNA, including single-stranded DNA, RNA, and phosphorothioate antisense. Antisense polynucleotides are typically generated within the cell by expression from antisense constructs that contain the antisense strand as the transcribed strand. Antisense polynucleotides will bind and/or interfere with the translation of the corresponding mRNA. Antisense RNA or antisense oligodeoxynucleotides (antisense ODNs) can both be used and may also be prepared in vitro synthetically or by means of recombinant DNA techniques. In order to avoid their digestion by DNAse, ODNs and antisense RNAs may be chemically modified. Trans-cleaving catalytic RNAs (ribozymes) are RNA molecules possessing endoribonuclease activity. Ribozymes are specifically designed for a particular target, and the target message must contain a specific nucleotide sequence. They are engineered to cleave any RNA species site-specifically in the background of cellular RNA. The cleavage event renders the mRNA unstable and prevents protein expression.

In other advantageous embodiments the used methods for reducing SHP expression on a post-transcriptional level are based on RNA interference (RNAi). Methods for downregulating genes by RNAi are well known to the skilled person and thus, do not need any detailed description here. Examples of RNAi inducing compounds that can be used to knockdown the expression of the SHP encoding gene include but are not limited to short interfering nucleic acids (siNA), short interfering RNA (siRNA), microRNA (miRNA), short hairpin RNAs (shRNA) as well as precursors thereof which are processed in the cell to the actual RNAi inducing compound. According to one embodiment, a siRNA is used for silencing. The siRNA may be provided as double-stranded molecule having 3' overhangs on each strand. Blunt ended molecules may also be used. Said siRNA may comprise desoxy—as well as ribonucleotides and furthermore, may comprise modified nucleotides. Several embodiments and variations of siRNA compounds are known in the prior art and can be used to reduce expression of the SHP gene. In order to efficiently induce silencing, the siRNA used as RNAi inducing compound is substantially complementary to a portion of the target gene transcript for inhibiting the expression of said gene by RNA interference.

The present disclosure relates generally to genetic control of infestations in host organisms belonging to the order Hemiptera. More particularly, the present disclosure includes methods for delivery of pest control agents to an aphid pest. Such pest control agents cause, directly or indirectly, an impairment in the ability of the pest to maintain itself, grow or otherwise infest a target host or symbiont. The present disclosure provides methods for employing stabilized dsRNA molecules in the diet of the pest as a means for suppression of the targeted genes encoding SHP in the pest, thus achieving desired control of pest infestations in, or about the host or symbiont targeted by the pest.

In accomplishing the foregoing, the present disclosure provides methods of inhibiting expression of the SHP encoding target gene in an insect pest, in particular in an insect belonging to the order Hemiptera including insects belonging to the suborder Sternorrhyncha and/or to the infraorder Fulgoromorpha, in particular in aphids like *Acyrthosiphon pisum*, resulting in the cessation of feeding, growth, development, reproduction, infectivity, and eventually may result in the death of the pest.

The method comprises in one embodiment introducing partial or fully stabilized double-stranded RNA (dsRNA) nucleotide molecules into a nutritional composition that the pest relies on as a food source, and making the nutritional composition available to the pest for feeding. Ingestion of the nutritional composition containing the double stranded or siRNA molecules results in the uptake of the molecules by the cells of the pest, resulting in the inhibition of expression of at least one target gene in the cells of the pest. Inhibition of the target gene exerts a deleterious effect upon the pest.

In certain embodiments, dsRNA molecules provided by the disclosure comprise nucleotide sequences complementary to a nucleic acid sequence comprised in SEQ ID NO:1, the inhibition of which in a pest organism results in the reduction or removal of SHP. The nucleotide sequence selected may exhibit from about 80% to at least about 100% sequence identity to 16 to 25 contiguous nucleotides of SEQ ID NO:1, including the complement thereof. Such inhibition can be described as specific in that a nucleotide sequence from a portion of the SHP encoding target gene is chosen from which the inhibitory dsRNA or siRNA is transcribed. The method is effective in inhibiting the expression of the SHP target gene and can be used to inhibit many different types of pests. In a particular embodiment, the nucleotide sequence is SEQ ID NO:2.

In advantageous embodiments, the nucleic acid sequences identified as having a pest protective effect may be readily expressed as dsRNA molecules through the creation of appropriate expression constructs. For example, such sequences can be expressed as a hairpin and stem and loop structure by taking a first segment corresponding to SEQ ID NO:1 or a fragment thereof, linking this sequence to a second segment spacer region that is not homologous or complementary to the first segment, and linking this to a third segment that transcribes an RNA, wherein at least a portion of the third segment is substantially complementary to the first segment. Such a construct forms a stem and loop structure by hybridization of the first segment with the third segment and a loop structure forms comprising the second segment (WO94/01550, WO98/05770, US 2002/0048814Al, and US 2003/0018993 A1).

A. Definitions

As used in the present disclosure, "cell", "cell line", and "cell culture" can be used interchangeably and all such designations include progeny. Thus, the words "transformants" or "transformed cells" includes the primary subject cell and cultures derived therefrom without regard for the number of transfers. It is also understood that all progeny may not be precisely identical in DNA content, due to deliberate or inadvertent mutations. Mutant progeny that have the same functionality as screened for in the originally transformed cell are included.

As used herein, the phrase "coding sequence", "encoding sequence", "structural nucleotide sequence" or "structural nucleic acid molecule" refers to a nucleotide sequence that is translated into a polypeptide, usually via mRNA, when placed under the control of appropriate regulatory sequences. The boundaries of the coding sequence are determined by a translation start codon at the 5'-terminus and a translation stop codon at the 3'-terminus. A coding sequence can include, but is not limited to, genomic DNA5 cDNA, EST and recombinant nucleotide sequences.

The term "complementary" as used herein refers to a relationship between two nucleic acid sequences. One nucleic acid sequence is complementary to a second nucleic acid sequence if it is capable of forming a duplex with the second nucleic acid, wherein each residue of the duplex forms a guanosine-cytidine (G-C) or adenosine-thymidine (A-T) base pair or an equivalent base pair. Equivalent base pairs can include nucleoside or nucleotide analogues other than guanosine, cytidine, adenosine, or thymidine.

The term "derivative" as used herein, refers to a nucleic acid molecule that has similar binding characteristics to the SHP target nucleic acid sequence as a nucleic acid molecule according to one of the claimed sequences.

As used herein, the term "derived from" refers to a specified nucleotide sequence that may be obtained from a particular specified source or species, albeit not necessarily directly from that specified source or species.

The term "expression clone" refers to DNA sequences containing a desired coding sequence and control sequences in operable linkage, so that hosts transformed with these sequences are capable of producing the encoded proteins. The term "expression system" refers to a host transformed with an expression clone. To effect transformation, the expression clone may be included on a vector; however, the relevant DNA may also be integrated into the host chromosome.

The term "gene" refers to a DNA sequence that comprises control and coding sequences necessary for the production of a recoverable bioactive polypeptide or precursor.

The term "homologue of the nucleic acid molecule" refers to a nucleic acid molecule the sequence of which has one or more nucleotides added, deleted, substituted or otherwise chemically modified in comparison to a nucleic acid molecule according to one of the claimed sequences, provided always that the homologue retains substantially the same inhibitory effect on SHP.

The term "isolated" describes any molecule separated from its natural source.

As used herein, the term "nucleic acid" refers to a single or double-stranded polymer of deoxyribonucleotide or ribonucleotide bases read from the 5' to the 3' end. The "nucleic acid" may also optionally contain non-naturally occurring or altered nucleotide bases that permit correct read through by a polymerase and do not reduce expression of a polypeptide encoded by that nucleic acid. The term "nucleotide sequence" or "nucleic acid sequence" refers to both the sense and antisense strands of a nucleic acid as either individual single strands or in the duplex. The term "ribonucleic acid" (RNA) is inclusive of RNAi (inhibitory RNA), dsRNA (double stranded RNA), siRNA (small interfering RNA), mRNA (messenger RNA), miRNA (micro-RNA), tRNA (transfer RNA, whether charged or discharged with a corresponding acylated amino acid), and cRNA (complementary RNA) and the term "deoxyribonucleic acid" (DNA) is inclusive of cDNA and genomic DNA and DNA-RNA hybrids. The words "nucleic acid segment", "nucleotide sequence segment", or more generally "segment" will be understood by those in the art as a functional term that includes both genomic sequences, ribosomal RNA sequences, transfer RNA sequences, messenger RNA sequences, operon sequences and smaller engineered nucleotide sequences that express or may be adapted to express, proteins, polypeptides or peptides.

Provided according to the disclosure are nucleotide sequences, the expression of which results in an RNA sequence which is substantially homologous to an RNA molecule of a targeted gene encoding SHP in an insect that comprises an RNA sequence encoded by a nucleotide sequence within the genome of the insect. Thus, after ingestion of the stabilized RNA sequence down-regulation of the nucleotide sequence of the target gene in the cells of the insect may be obtained resulting in a deleterious effect on the maintenance, viability, proliferation, reproduction and infestation of the insect.

As used herein, the term "homologous" or "homologs", with reference to a nucleic acid sequence, includes a nucleotide sequence that hybridizes under stringent conditions to one of the coding sequences of SEQ ID NO:1, SEQ ID NO. 5 or SEQ ID NO. 7, or the complements thereof. Sequences that hybridize for example under stringent conditions to SEQ ID NO:1, or the complements thereof, are those that allow an antiparallel alignment to take place between the two sequences, and the two sequences are then able, under stringent conditions, to form hydrogen bonds with corresponding bases on the opposite strand to form a duplex molecule that is sufficiently stable under the stringent conditions to be detectable using methods well known in the art. Substantially homologous sequences have preferably from about 70% to about 80% sequence identity, or more preferably from about 80% to about 85% sequence identity, or most preferable from about 90% to about 95% sequence identity, to about 99% sequence identity, to the referent nucleotide sequences of SEQ ID NO:1, SEQ ID NO. 5 or SEQ ID NO. 7, or to the sequence of SEQ ID NO:2 as set forth in the sequence listing, or the complements thereof.

As used herein, the term "insect control agent", or "gene suppression agent" refers to a particular RNA molecule comprising a first RNA segment and a second RNA segment, wherein the complementarity between the first and the second RNA segments results in the ability of the two segments to hybridize in vivo and in vitro to form a double stranded molecule. It may generally be preferable to include a third RNA segment linking and stabilizing the first and second sequences such that the entire structure forms into a stem and loop structure, or even more tightly hybridizing structures may form into a stem-loop knotted structure. Alternatively, a symmetrical hairpin could be formed without a third segment in which there is no designed loop, but for steric reasons a hairpin would create its own loop when the stem is long enough to stabilize itself. The first and the second RNA segments will generally be within the length of the RNA molecule and are substantially inverted repeats of each other and linked together by the third RNA segment. The first and the second segments correspond invariably and not respectively to a sense and an antisense sequence with respect to the target RNA transcribed fern the target gene in the target insect pest that is suppressed by the ingestion of the dsRNA molecule. The insect control agent can also be a substantially purified (or isolated) nucleic acid molecule and more specifically nucleic acid molecules or nucleic acid fragment molecules thereof from a genomic DNA (gDNA) or cDNA library. Alternatively, the fragments may comprise smaller oligonucleotides having from about 15 to about 250 nucleotide residues, and more preferably, about 15 to about 30 nucleotide residues.

As used herein, the phrase "inhibition of gene expression" or "inhibiting expression of a target gene in the cell of an insect" refers to the absence (or observable decrease) in the level of protein and/or mRNA product from the target gene. Specificity refers to the ability to inhibit the target gene without manifest effects on other genes of the cell and without any effects on any gene within the cell that is producing the dsRNA molecule. The inhibition of gene expression of the target gene in the insect pest may result in novel phenotypic traits in the insect pest.

The term "microorganism" includes prokaryotic and eukaryotic microbial species such as bacteria, fungi and algae. Fungi include yeasts and filamentous fungi, among others. Illustrative prokaryotes, both Gram-negative and Gram-positive, include Enter obacteriaceae, such as *Escherichia, Erwinia, Shigella, Salmonella*, and *Proteus*; Bacillaceae; Rhizobiceae, such as *Rhizobium*; Spirillaceae, such as *photobacterium, Zymomonas, Serratia, Aeromonas, Vibrio, Desulfovibrio*, Spirillum', Lactobacillaceae; Pseudomoriadaceae, such as *Pseudomonas* and *Acetobacter*; Azotobacteraceae, Actinomycetales, and Nitrobacteraceae. Among eukaryotes are fungi, such as *Phycomycetes* and *Ascomycetes*, which includes yeast, such as *Saccharomyces* and *Schizosaccharomyces*; and Basidiomycetes, such as *Rhodotorula, Aureobasidium, Sporobolomyces*, and the like.

The term "operably linked", as used in reference to a regulatory sequence and a structural nucleotide sequence, means that the regulatory sequence causes regulated expression of the linked structural nucleotide sequence. "Regulatory sequences" or "control elements" refer to nucleotide sequences located upstream (5' noncoding sequences), within, or downstream (3' non-translated sequences) of a structural nucleotide sequence, and which influence the timing and level or amount of transcription, RNA processing or stability, or translation of the associated structural nucleotide sequence. Regulatory sequences may include promoters, translation leader sequences, introns, enhancers, stem-loop structures, repressor binding sequences, and polyadenylation recognition sequences and the like.

In the present description, "pest control" refers to the removal or the reduction of harm of pests. The concept of "pest control" include reducing feeding of the target pest, killing of pests (extermination), pest proliferation inhibition, pest growth inhibition, repelling of pests (repellence), and the removal or the reduction of harm of pests (for example, inhibition of ingestion capacity of agricultural pests.

The term "plant" includes the plant body, plant organs (for example, leaves, petals, stem, root, rhizome, and seeds), plant tissues (for example, epidermis, phloem, parenchyma, xylem, and vascular bundle), and plant cells. In addition, the term "plant cell" includes seed suspension cultures, embryos, meristematic tissue regions, callus tissues, cells derived from leaves and roots, and gametophytes (embryos and pollens) and their precursors. When plant culture cells are transformed, an organ or individual is regenerated from the transformed cells by a known tissue culture method. These operations are readily performed by those skilled in the art. An example is described below. Firstly, the transformed plant cells are cultured in a sterilized callus forming medium (containing a carbon source, saccharides, vitamins, inorganics, and phytohormones such as auxin and cytokinin), thereby forming a dedifferentiated calluse which indefinitely proliferates (callus induction). The formed callus is transferred to a new medium containing a plant growth regulator such as auxin, and further proliferated thereon (subcultivation). When the callus induction is carried out on a solid medium such as agar and subcultivation is carried out in a liquid medium, the respective cultures are efficiently achieved. Secondly, the callus proliferated by subcultivation was cultured under appropriate conditions, thereby inducing redifferentiation of the organ (inductive redifferentiation), and regenerating the plant body. The inductive redifferentiation is achieved by appropriately adjusting the type and amount of the various components of the medium, including plant growth regulators such as auxin and cytokinin, and the carbon source, and the light and temperature. The inductive redifferentiation forms adventitious embryos, adventitious roots, adventitious buds, adventitious foliage, and others, and they are grown into a complete plant body. The plant before being a complete plant body may be stored in the form of, for example, capsulated artificial seeds, dry embryos, lyophilized cells, or tissues.

The term "plasmid", "vector system", "vector" or "expression vector" means a construct capable of in vivo or in vitro expression. In the context of the present disclosure, these constructs may be used to introduce genes encoding enzymes into host cells.

The term "polynucleotide" corresponds to any genetic material of any length and any sequence, comprising single-stranded and double-stranded DNA and RNA molecules, including regulatory elements, structural genes, groups of genes, plasmids, whole genomes and fragments thereof.

The term "recombinant DNA" or "recombinant nucleotide sequence" refers to DNA that contains a genetically engineered modification through manipulation via mutagenesis, restriction enzymes, and the like.

The term "stringent conditions" relates to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M Na ion, typically about 0.01 to 1.0 M Na ion (or other salts) at pH 7.0 to 8.3 and the temperature is at least about 30° C. for short probes (e.g. 10 to 50 nucleotides) and at least about 60° C. for longer probes. Stringent conditions may also be achieved with the addition of destabilizing agents, such as formamide and the like.

As used herein, the term "sequence identity", "sequence similarity" or "homology" is used to describe sequence relationships between two or more nucleotide sequences. The percentage of "sequence identity" between two sequences is determined by comparing two optimally aligned sequences over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. A sequence that is identical at every position in comparison to a reference sequence is said to be identical to the reference sequence and vice-versa. A first nucleotide sequence when observed in the 5' to 3' direction is said to be a "complement" of, or complementary to, a second or reference nucleotide sequence observed in the 3' to 5' direction if the first nucleotide sequence exhibits complete complementarity with the second or reference sequence. As used herein, nucleic acid sequence molecules are said to exhibit "complete complementarity" when every nucleotide of one of the sequences read 5' to 3' is complementary to every nucleotide of the other sequence when read 3' to 5'. A nucleotide sequence that is complementary to a reference nucleotide sequence will exhibit a sequence identical to the reverse complement sequence of the reference nucleotide sequence. These terms and descriptions are well defined in the art and are easily understood by those of ordinary skill in the art.

By "synergistic" it is meant to include the synergistic effects of the combination on the pesticidal activity (or efficacy) of the combination of the transgenic event and the pesticide. However, it is not intended that such synergistic effects be limited to the pesticidal activity, but that they should also include such unexpected advantages as increased scope of activity, advantageous activity profile as related to type and amount of damage reduction, decreased cost of pesticide and application, decreased pesticide distribution in the environment, decreased pesticide exposure of personnel who produce, handle and plant corn seeds, and other advantages known to those skilled in the art.

The term "variant of the nucleic acid molecule" refers herein to a nucleic acid molecule which is substantially similar in structure and biological activity to a nucleic acid molecule according to one of the claimed sequences.

The "pest" refers to the pest subjected to pest control, or the pest controlled by the present disclosure. The pest may be two or more pests and are not particularly limited. In general, pests are broadly divided into agricultural pests, sanitary pests, and unpleasant pests. "Agricultural pests" refer to the pests that attack crops (including garden crops and crops during storage). "Sanitary pests" refer to the pests that attack the sanitary environment of human. In addition, "unpleasant pests" refer to the pests that attack the mood of human by their appearance or motion. The present disclosure is also applicable to the pests that attack the assets of human (for example, termite and bristletail) and livestock (for example, mosquito and parasite).

Therefore, as used herein, the term "target pest" refers to insects, arachnids, crustaceans, fungi, bacteria, viruses, nematodes, flatworms, roundworms, pinworms, hookworms, tapeworms, trypanosomes, schistosomes, botflies, fleas, ticks, mites, and lice and the like that are pervasive in the human environment and that may ingest or contact one or more cells, tissues, or fluids produced by a pest host or symbiont transformed to express or coated with a double stranded gene suppression agent or that may ingest plant material containing the gene suppression agent.

As used herein, a "pest resistance" trait is a characteristic of a transgenic plant, transgenic animal, transgenic host or transgenic symbiont that causes the plant, animal, host, or symbiont to be resistant to attack from a pest that typically is capable of inflicting damage or loss to the plant, animal, host or symbiont. Such pest resistance can arise from a natural mutation or more typically from incorporation of recombinant DNA that confers pest resistance. To impart insect resistance to a transgenic plant a recombinant DNA can, for example, be transcribed into a RNA molecule that forms a dsRNA molecule within the tissues or fluids of the recombinant plant. The dsRNA molecule is comprised in part of a segment of RNA that is identical to a corresponding RNA segment encoded from a DNA sequence within an insect pest that prefers to feed on the recombinant plant. Expression of the gene within the target insect pest is suppressed by the dsRNA, and the suppression of expression of the gene in the target insect pest results in the plant being insect resistant. Fire et al. (U.S. Pat. No. 6,506,599) generically described inhibition of pest infestation, providing specifics only about several nucleotide sequences that were effective for inhibition of gene function in the nematode species Caenorhabditis elegans. Similarly, Plaetinck et al. (US 2003/0061626) describe the use of dsRNA for inhibiting gene function in a variety of nematode pests. Mesa et al. (US 2003/0150017) describe using dsDNA sequences to transform host cells to express corresponding dsRNA sequences that are substantially identical to target sequences in specific pathogens, and particularly describe constructing recombinant plants expressing such dsRNA sequences for ingestion by various plant pests, facilitating down-regulation of a gene in the genome of the pest and improving the resistance of the plant to the pest infestation.

B. Target Pests

The present disclosure pertains to pest control methods comprising incorporating an inhibitor against the structural sheath protein (SHP) into the body of an agricultural target pest expressing SHP. In particular, the mRNA encoding the SHP comprises the sequence set forth in SEQ ID NO: 1, or homologs thereof, wherein said homologs may have a sequence identity of at least 80%, in particular of at least 85%, in particular of at least 90% to SEQ ID NO: 1. Examples for such homologs are shown in Rao S A K (2011). In an advantageous example said homologs are parts of sequences that encode a functional SHP in the target pest.

In advantageous embodiments of the present disclosure, the target pests are insect belonging to the insect order Hemiptera also known as the true bugs. Many Hemipteran insects are important agricultural pests because they cause direct feeding damage to their host plants and/or transmit plant disease agents including viruses and bacteria. Microscopic and behavioral studies on different Hemiptera species showed that their exuviae (molted skins) normally had either fully or partially extended stylets in a feeding-like position. In most cases these stylets were still partially embedded in their host plants after ecdysis, which indicated that plant-feeding hemipteran nymphs use their stylets to anchor themselves to host plants during molting.

As an example, aphids feed by sucking the sugary sap from the phloem sieve tubes of higher plants through specially adapted mouthparts known as stylets. Before feeding can take place, the stylet must penetrate the plant epidermis and propagate through the cortical layer. To facilitate this process, aphids secrete gel saliva that hardens to form a surface flange and a continuous tubular sheath encasing the full length of the stylet in the apoplast. Traces of gel saliva form in artificial diet a structure reminiscent of a pearl necklace, indicating that the salivary sheath is formed progressively from drops of saliva that harden rapidly. During stylet propagation, the continuous sheath around the stylet provides mechanical stability and protect against chemical defenses. The structural sheath protein (SHP) is responsible for hardening of the salivary sheath.

Other hemiptera including plant-sucking insects such as whiteflies and planthoppers also form with SHP a salivary sheath by secretion of gel saliva (Freeman et al., 2001 and Brentassi et al., 2007) and show feeding associated secretion of watery saliva.

Examples of the target pests belonging to Hemiptera include insects of the suborder Sternorrhyncha including aphids and the infraorder Fulgoromorpha. In particular, examples of the target pests belonging to Hemiptera include *Nilaparvata lugens, Sogatella furcifera, Laodelphax stratella, Nephotettix cincticeps, Recilia dorsalis, Stenotus rubrovittatus, Trigonotylus caelestialium, Leptocorisa chinensis, Nezara antennata, Nezara viridula, Lagynotomus elongatus, Scotinophara lurida, Eysarcoris annamita, Eysarcoris lewisi, Eysarcoris ventralis, Togo hemipterus Scott, Cletus punctiger, Piezodorus hybneri, Halyomorpha* halys, *Dolycoris baccarum, Neotoxoptera formosana, Rhopalosiphum padi, Rhopalosiphum maidis, Acyrthosiphon pisum* and *Aphis glycines*.

In advantageous embodiments, the target pests are belonging to the genera of aphids, in particular *Acyrthosiphon pisum*.

C. SHP Inhibitor

According to the pest control methods of the present disclosure, an inhibitor against SHP is incorporated into the body of the target pest. The term "SHP inhibitor" is used as the generic name of the substances inhibiting SHP. The SHP inhibitor may be of any type as long as it has inhibitory against the expression, the transcription and/or the translation of SHP and/or has inhibitory activity against SHP.

Examples of the SHP inhibitor include a nucleic acid that inhibits the expression of the SHP gene, and a substance that specifically binds to SHP (for example, an antibody or a low molecular weight compound). The former one is further described below. The substance that specifically binds to SHP may be obtained or prepared using binding assay targeted at SHP. An antibody that specifically binds to SHP may be prepared using, for example, an immunological method, a phage display method, or a ribosome display method.

According to one aspect of the present disclosure, a compound selected from the group consisting of the following (a) to (d) is used as the SHP inhibitor:

(a) a RNAi inducing compound targeted a nucleic acid coding SHP or parts thereof;

(b) a nucleic acid construct intracellularly producing a RNAi inducing compound targeted a nucleic acid coding SHP or parts thereof;

(c) an antisense nucleic acid targeted at the transcript product of a gene coding SHP of the target pest; and (d) a ribozyme targeted at the transcript product of a gene coding SHP of the target pest.

The (a) and (b) are the compounds used for the inhibition of expression by so-called RNAi (RNA interference). In other words, when the compound (a) or (b) is used, the expression of SHP is inhibited by RNAi, whereby pest control effect is achieved. In this manner, the use of RNAi allows specific control of the target pest, and facilitates rapid achievement of pest control effect. Furthermore, owing to its properties, the possibility of occurrence of resistant strains is likely extremely low. In addition, RNAi does not modify plant genes, and thus will not genetically influence them.

The "RNAi" refers to the inhibition of expression of the target gene by the introduction of an RNA composed of a sequence homologous to that of the target gene (specifically homologue to the mRNA corresponding to the target gene) into the target cell. For the inhibition of expression using the RNAi method in pests such as insects, generally, a dsRNA (double strand RNA) composed of a sequence corresponding a part of the target gene (the gene coding the IAP of the target pest). Two or more dsRNAs may be used for one target gene.

The RNAi targeted at the gene of a mammal cell uses a short dsRNA (siRNA) of about 16 to 25 nucleotides. When the RNAi is targeted at the gene of a pest such as an insect, a long dsRNA of more than several hundreds of nucleotides is preferred because owing to its effectiveness. The length of the dsRNA used for RNAi is, for example, 30 nucleotides or more, and preferably 200 nucleotides or more (for example, from 200 to 500 nucleotides). The use of a dsRNA is preferred for inducing effective inhibition of expression, but the use of a single strand RNA will also be contemplated. The dsRNA used herein is not necessarily composed of two molecules of sense and antisense strands, and, for example, may have a structure wherein the sense and antisense strands composing the dsRNA are connected via a hairpin loop. A dsRNA composed of a modified RNA may be used. Examples of the modification include phosphorothioation, and the use of a modified base (for example, fluorescence-labeled base). In advantageous embodiments, the RNAi inducing compound is a compound selected from the group consisting of short interfering nucleic acids, siNA, short interfering RNA (siRNA), microRNA (miRNA), short hairpin RNAs (shRNA) and precursors thereof which are processed in the cell to the actual RNAi inducing compound. In a preferred embodiment, the precursor is double-stranded RNA (dsRNA). An example of a dsRNA used in the pest control method according to the present disclosure is a dsRNA comprising the sequence set forth in SEQ ID NO: 2, or homologs thereof, wherein said homologs have a sequence identity of at least 80%, in particular of at least 85%, in particular of at least 90% to SEQ ID NO: 2.

An RNAi specific to the target gene can be also produced by intracellularly expression of a dsRNA targeted at the target gene. The nucleic acid construct (b) is used as such a means.

The dsRNA used in the RNAi method may be prepared by chemical synthesis, or in vitro or in vivo using an appropriate expression vector. The method using an expression vector is particularly effective for the preparation of a relatively long dsRNA. The design of dsRNA normally includes the sequence (continuous sequence) specific to the target nucleic acid. Programs and algorithms for selecting an appropriate target sequence have been developed.

As mentioned above, advantageous embodiments of the present disclosure pertain to the use of RNA interference to silence the expression of SHP to disrupt the sheath formation and therefore the insect feeding and reproduction were inhibited.

The above described (c) is a compound used for the inhibition of expression by an antisense method. The inhibition of expression using an antisense method is generally carried out using an antisense construct that produces a RNA complementary to the portion specific to the mRNA corresponding to the target gene upon transcription. The antisense construct (also referred to as antisense nucleic acid) is, for example, introduced into the target cell in the form of an expression plasmid. The antisense construct may be an oligonucleotide probe that hybridizes with the DNA sequence or corresponding mRNA sequence of the target gene (these sequences may be collectively referred to as "target nucleic acid") upon introduction into the target cell, and inhibits their expression. The oligonucleotide probe is preferably resistant to endogenous nucleases such as exonuclease and/or endonuclease. When a DNA molecule is used as an antisense nucleic acid, the DNA molecule is preferably an oligodeoxyribonucleotide derived from the region containing the translation initiation site of the mRNA corresponding to the target gene (for example, the region from −10 to +10).

The complementation between the antisense nucleic acid and target nucleic acid is preferably precise, but some mismatch may occur. The hybridization capacity of the antisense nucleic acid for the target nucleic acid generally depends on the degree of complementation between the nucleic acids and the length of the antisense nucleic acid. In principle, the longer the antisense nucleic acid, the more stable double strand (or triplex) is formed between the antisense and target nucleic acids, even if many mismatches occur. Those skilled in the art can examine the degree of acceptable mismatch using a standard method.

The antisense nucleic acid may be DNA, RNA, or a chimera mixture thereof, or a derivative or modified product thereof. The antisense nucleic acid may be single or double strand. The stability and hybridization capacity of the antisense nucleic acid are improved by the modification of the base, sugar, or phosphoric acid backbone. The antisense nucleic acid may be synthesized by an ordinary method using, for example, a commercially available automatic DNA synthesizing apparatus (for example, manufactured by Applied Biosystems). The preparation of the modified nucleic acid and derivatives may refer to, for example, Stein et al. (1988), Nucl. Acids Res. 16:3209 or Sarin et al., (1988), Proc. Natl. Acad. Sci. U.S.A. 85:7448-7451.

In order to improve the action of the antisense nucleic acid in the target cell, a promoter (for example, actin promoter or ie1 promoter) that strongly acts in the target cell may be used. More specifically, when a construct containing the antisense nucleic acid under control of the promoter is introduced into the target cell, a sufficient amount of antisense nucleic acid is transcribed.

According to one aspect of the present disclosure, the inhibition of expression by ribozyme is used (when the compound (d) is used). The mRNA corresponding to the target gene may be destroyed using a ribozyme that cleaves the mRNA at the site-specific recognition sequence, but preferably a hammerhead ribozyme is used. The method for constructing the hammerhead ribozyme may be referred to, for example, Haseloff and Gerlach, 1988, Nature, 334:585-591.

In the same manner as in the antisense method, for example, for the purpose of improving stability and target performance, the ribozyme construction may use a modified oligonucleotide. In order to produce an effective amount of ribozyme within the target cell, it is preferred that a nucleic acid construct including DNA coding the ribozyme be used under the control of a promoter which strongly acts in insect cells (for example, an actin promoter or an ie1 promoter).

SEQ ID NO. 1 shows a part of a mRNA sequence (NA 647-4776) encoding SHP in *Acyrthosiphon pisum* (SEQ ID NOs: 1).

SEQ ID NO: 2 is a dsRNA derived from SEQ ID NO.1.

SEQ ID NO: 3 is a plasmid nucleic acid sequence after cloning a dsRNA production vector.

SEQ ID NO: 4 is an amino acid sequence comprised in SHP from *Acyrthosiphon pisum*.

SEQ ID NO: 5 is a nucleic acid sequence comprised in a SHP mRNA from *Sitobion avenae* and SEQ ID NO: 6 is the corresponding amino acid sequence comprised in the encoded protein.

SEQ ID NO: 7 is a nucleic acid sequence comprised in a SHP mRNA from *Metopolophium dirhodum* and SEQ ID NO: 8 is the corresponding amino acid sequence comprised in the encoded protein.

D. Nucleic Acid Compositions and Constructs

The present disclosure provides recombinant DNA constructs for use in achieving stable transformation of particular host or symbiont pest targets. Transformed host or symbiont pest targets may express pesticidally effective levels of preferred dsRNA or siRNA molecules from the recombinant DNA constructs, and provide the molecules in the diet of the pest. Pairs of isolated and purified nucleotide sequences may be provided from cDNA library and/or genomic library information. The pairs of nucleotide sequences may be derived from any preferred coleopteran pest for use as thermal amplification primers to generate DNA templates for the preparation of dsRNA and siRNA molecules of the present disclosure.

Provided according to the present disclosure are nucleotide sequences, the expression of which results in an RNA sequence which is substantially homologous to an RNA molecule of a targeted gene in an insect that comprises an RNA sequence encoded by a nucleotide sequence within the genome of the insect. Thus, after ingestion of the stabilized RNA sequence down-regulation of the nucleotide sequence of the target gene in the cells of the insect may be obtained resulting in a deleterious effect on the maintenance, viability, proliferation, reproduction and infestation of the insect.

Examples of isolated polynucleotide suitable as a pest control agent against a target pest are the following (A) to (d):
a) a polynucleotide comprising a nucleic acid sequence of SEQ ID NO:1;
b) a polynucleotide that hybridizes to a nucleic acid sequence of SEQ ID NO:1 under stringent conditions;
c) a polynucleotide of at least 70, at least 80, at least 85, at least 90 percent sequence identity, to a nucleic acid sequence of SEQ ID NO:1;
d) a fragment of at least 16 contiguous nucleotides of a nucleic acid sequence of SEQ ID NO:1; and
e) a complement of the sequence of (a), (b), (c) or (d),
wherein ingestion by a Hemiptera crop plant pest of a double stranded ribonucleotide sequence comprising at least one strand that is complementary to said polynucleotide or said fragment reduce feeding of said pest.

Further provided by the disclosure is a fragment or concatemer of a nucleic acid sequence of SEQ ID NO:1. The fragment may be defined as causing the death, inhibition, stunting, or cessation of feeding of a pest when expressed as a dsRNA and provided to the pest. The fragment may, for example, comprise at least about 16, 17, 18 19, 21, 23, 25, 40, 60, 80, 100, 125 or more contiguous nucleotides of the sequence set force in SEQ ID NO:1, or a complement thereof. One beneficial DNA segment for use in the present disclosure is at least from about 19 to about 23, or about 23 to about 100 nucleotides up to about 2000 nucleotides or more in length. Particularly useful will be dsRNA sequences including about 23 to about 300 nucleotides homologous to a pest target sequence. The disclosure also provides a ribonucleic acid expressed from any of such sequences including a dsRNA. A sequence selected for use in expression of a gene suppression agent can be constructed from a single sequence derived from one or more target pests and intended for use in expression of an RNA that functions in the suppression of a single gene or gene family in the one or more target pests, or that the DNA sequence can be constructed as a chimera from a plurality of DNA sequences.

In further embodiments, the disclosure pertains to recombinant DNA constructs comprising a nucleic acid molecule encoding a dsRNA molecule described herein. The dsRNA may be formed by transcription of one strand of the dsRNA molecule from a nucleotide sequence which is at least from about 80% to about 100% identical to a nucleotide sequence comprising SEQ ID NO:1. Such recombinant DNA constructs may be defined as producing dsRNA molecules capable of inhibiting the expression of endogenous target gene(s) in a pest cell upon ingestion. The construct may comprise a nucleotide sequence of the plant operably linked to a promoter sequence that functions in the host cell. Such a promoter may be tissue-specific and may, for example, be specific to a tissue type which is the subject of pest attack. In the case of rootworms, for example, it may be desired to use a promoter providing root-preferred expression.

Nucleic acid constructs in accordance with the disclosure may comprise at least one non-naturally occurring nucleotide sequence that can be transcribed into a single stranded RNA capable of forming a dsRNA molecule in vivo through hybridization. Such dsRNA sequences self-assemble and can be provided in the diet of a coleopteran pest to achieve the desired inhibition.

A recombinant DNA construct may comprise two different non-naturally occurring sequences which, when expressed in vivo as dsRNA sequences and provided in the diet of a coleopteran pest, inhibit the expression of at least two different target genes in the cell of the coleopteran pest. In certain embodiments, at least 3, 4, 5, 6, 8 or 10 or more different dsRNAs are produced in a cell or plant comprising the cell that has a pest-inhibitory effect. The dsRNAs may expressed from multiple constructs introduced in different transformation events or could be introduced on a single nucleic acid molecule. The dsRNAs may be expressed using a single promoter or multiple promoters. Li one embodiments of the disclosure, single dsRNAs are produced that comprise nucleic acids homologous to multiple loci within a pest. hi still yet another aspect, the disclosure provides a recombinant host cell having in its genome at least one recombinant DNA sequence that is transcribed to produce at least one dsRNA molecule that functions when ingested by a coleopteran pest to inhibit the expression of a target gene in the pest. The dsRNA molecule may be encoded by any of the nucleic acids described herein and as set forth in the sequence listing. The present disclosure also provides a transformed plant cell having in its genome at least one recombinant DNA sequence described herein. Transgenic plants comprising such a transformed plant cell are also provided, including progeny plants of any generation, seeds, and plant products, each comprising the recombinant DNA.

The present disclosure provides DNA sequences capable of being expressed as a RNA in a cell or microorganism to inhibit target gene expression in a cell, tissue or organ of an insect. The sequences comprises a DNA molecule coding for one or more different nucleotide sequences, wherein each of the different nucleotide sequences comprises a sense nucleotide sequence and an antisense nucleotide sequence connected by a spacer sequence coding for a dsRNA molecule of the present disclosure. The spacer sequence constitutes part of the sense nucleotide sequence or the antisense nucleotide sequence and forms within the dsRNA molecule between the sense and antisense sequences. The sense nucleotide sequence or the antisense nucleotide sequence is substantially identical to the nucleotide sequence of the target gene or a derivative thereof or a complementary sequence thereto. The dsDNA molecule may be placed operably under the control of a promoter sequence that functions in the cell, tissue or organ of the host expressing the dsDNA to produce dsRNA molecules. In one embodiment, the DNA sequence may be derived from a nucleotide sequence of SEQ ID NO:1.

As mentioned above, the present disclosure also provides a DNA sequence for expression in a cell of a plant that, upon expression of the DNA to RNA and ingestion by a target pest achieves suppression of a target gene in a cell, tissue or organ of an insect pest. The dsRNA at least comprises one or multiple structural gene sequences, wherein each of the structural gene sequences comprises a sense nucleotide sequence and an antisense nucleotide sequence connected by a spacer sequence that forms a loop within the complementary and antisense sequences. The sense nucleotide sequence or the antisense nucleotide sequence is substantially identical to the nucleotide sequence of the target gene, derivative thereof, or sequence complementary thereto. The one or more structural gene sequences is placed operably under the control of one or more promoter sequences, at least one of which is operable in the cell, tissue or organ of a prokaryotic or eukaryotic organism, particularly a plant.

A gene sequence or fragment for pest control according to the present disclosure may be cloned between two tissue specific promoters, such as two root specific promoters which are operable in a transgenic plant cell and therein expressed to produce mRNA in the transgenic plant cell that form dsRNA molecules thereto. The dsRNA molecules contained in plant tissues are ingested by an insect so that the intended suppression of the target gene expression is achieved.

A nucleotide sequence provided by the present disclosure may comprise an inverted repeat separated by a "spacer sequence." The spacer sequence may be a region comprising any sequence of nucleotides that facilitates secondary structure formation between each repeat, where this is required. In one embodiment of the present disclosure, the spacer sequence is part of the sense or antisense coding sequence for mRNA. The spacer sequence may alternatively comprise any combination of nucleotides or homologues thereof that are capable of being linked covalently to a nucleic acid molecule. The spacer sequence may comprise a sequence of nucleotides of at least about 10-100 nucleotides in length, or alternatively at least about 100-200 nucleotides in length, at least 200-400 about nucleotides in length, or at least about 400-500 nucleotides in length.

The nucleic acid molecules or fragment of the nucleic acid molecules or other nucleic acid molecules in the sequence listing are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the complement of another nucleic acid molecule if they exhibit complete complementarity. Two molecules are said to be "minimally complementary" if they can hybridize to one another with sufficient stability to permit them to remain annealed to one another under at least conventional "low-stringency" conditions. Similarly, the molecules are said to be complementary if they can hybridize to one another with sufficient stability to permit them to remain annealed to one another under conventional "high-stringency" conditions. Conventional stringency conditions are described by Sambrook, et al. (1989), and by Haymes et al. (1985).

Departures from complete complementarity are therefore permissible, as long as such departures do not completely preclude the capacity of the molecules to form a double-stranded structure. Thus, in order for a nucleic acid molecule or a fragment of the nucleic acid molecule to serve as a primer or probe it needs only be sufficiently complementary in sequence to be able to form a stable double-stranded structure under the particular solvent and salt concentrations employed.

Appropriate stringency conditions which promote DNA hybridization are, for example, 6.0× sodium chloride/sodium citrate (SSC) at about 45° C., followed by a wash of 2.0×SSC at 50° C., are known to those skilled in the art or can be found in Current Protocols in Molecular Biology (1989). For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. A nucleic acid for use in the present disclosure may specifically hybridize to one or more of nucleic acid molecules from WCR or complements thereof under such conditions. Preferably, a nucleic acid for use in the present disclosure will exhibit at least from about 85%, or at least from about 90%, or at least from about 95%, or at least from about 98% or even about 100% sequence identity with a nucleic acid molecule of SEQ ID NO:1.

Nucleic acids of the present disclosure may also be synthesized, either completely or in part, especially where it is desirable to provide plant-preferred sequences, by methods known in the art. Thus, all or a portion of the nucleic acids of the present disclosure may be synthesized using codons preferred by a selected host. Species-preferred codons may be determined, for example, from the codons used most frequently in the proteins expressed in a particular host species. Other modifications of the nucleotide sequences may result in mutants having slightly altered activity. dsRNA or siRNA nucleotide sequences comprise double strands of polymerized ribonucleotide and may include modifications to either the phosphate-sugar backbone or the nucleoside. Modifications in RNA structure may be tailored to allow specific genetic inhibition. In one embodiment, the dsRNA molecules may be modified through an enzymatic process so that siRNA molecules may be generated. The siRNA can efficiently mediate the downregulation effect for some target genes in some insects. This enzymatic process may be accomplished by utilizing an RNAse III enzyme or a DICER enzyme, present in the cells of an insect, a vertebrate animal, a fungus or a plant in the eukaryotic RNAi pathway (Elbashir et al, 2002; Hamilton and Baulcombe, 1999). This process may also utilize a recombinant DICER or RNAse III introduced into the cells of a target insect through recombinant DNA techniques that are readily known to the skilled in the art. Both the DICER enzyme and RNAse III, being naturally occurring in an insect or being made through recombinant DNA techniques, cleave larger dsRNA strands into smaller oligonucleotides. The DICER enzymes specifically cut the dsRNA molecules into siRNA pieces each of which is about 19-25 nucleotides in length while the RNAse III enzymes normally cleave the dsRNA molecules into 12-15 base-pair siRNA. The siRNA molecules produced by the either of the enzymes have 2 to 3 nucleotide 3' overhangs, and 5' phosphate and 3' hydroxyl termini. The siRNA molecules generated by RNAse III enzyme are the same as those produced by Dicer enzymes in the eukaryotic RNAi pathway and are hence then targeted and degraded by an inherent cellular RNA-degrading mechanism after they are subsequently unwound, separated into single-stranded RNA and hybridize with the RNA sequences transcribed by the target gene. This process results in the effective degradation or removal of the RNA sequence encoded by the nucleotide sequence of the target gene in the insect. The outcome is the silencing of a particularly targeted nucleotide sequence within the insect. Detailed descriptions of enzymatic processes can be found in Harmon (2002).

In some embodiments, the present disclosure pertains to double stranded ribonucleotide sequences produced from the expression of a polynucleotide according to the present disclosure, wherein ingestion of said ribonucleotide sequence or fragments thereof as RNAi inducing compounds by a Hemiptera crop plant pest reduces feeding of said pest. In an advantageous embodiment, said double stranded ribonucleotide sequence comprises a nucleic acid sequence of SEQ ID NO:2, or homologs thereof, wherein said homologs have a sequence identity of at least 80%, in particular of at least 85%, in particular of at least 90%, in particular of at least 95% to SEQ ID NO: 2.

E. Incorporation of SHP Inhibitor

The manner for incorporation of the SHP inhibitor is not particularly limited, and may be selected according to the target pest. When the target pest is a pest that attacks a plant, for example, the agent (pesticide) containing the SHP inhibitor is in advance retained in the plant, which is to be attacked by the target pest, through application, spraying, or atomization. As a result of this, when the target pest ingests the plant, the SHP inhibitor is incorporated into the body of the target pest.

On the other hand, when a feed (feed agent) containing the SHP inhibitor is placed at the site of occurrence or in the route of entry of the target pest, the target pest ingests the feed, and thus the SHP inhibitor is incorporated into the body of the target pest. In addition, when the plant to be attacked is modified by the introduction of a gene coding the SHP inhibitor, the SHP inhibitor is incorporated into the body of the target pest when the pest ingests the transgenic plant. The transgenic plant used in this method may be a plant subjected to gene modification so as to express: (A) an siRNA targeted at a gene coding the SHP of the target pest; (B) an antisense nucleic acid targeted at the transcript product of a gene coding the SHP of the target pest; or (C) a ribozyme targeted at the transcript product of a gene coding the SHP of the target pest.

Therefore, in some embodiments, the pest control method according to the present disclosure comprise making a plant, which is to be attacked by the target pest, possess an agent containing the inhibitor by application, spraying, or atomization in advance, and incorporating the inhibitor into the body of the target pest by ingestion of the plant.

However, in some advantageous embodiments, the pest control method according to the present disclosure comprises incorporating the inhibitor into the body of the target pest by ingestion of a transgenic plant containing a gene encoding the inhibitor.

E. Vectors and Host Cell Transformation

As mentioned above, the present disclosure contemplates transformation of a nucleotide sequence of the present disclosure into a plant to achieve pest inhibitory levels of expression of one or more dsRNA molecules. A transformation vector can be readily prepared using methods available in the art. The transformation vector comprises one or more nucleotide sequences that is/are capable of being transcribed to an RNA molecule and that is/are substantially homologous and/or complementary to one or more nucleotide sequences encoded by the genome of the insect, such that upon uptake of the RNA there is down-regulation of expression of at least one of the respective nucleotide sequences of the genome of the insect.

The transformation vector may be termed a dsDNA construct and may also be defined as a recombinant molecule, an insect control agent, a genetic molecule or a chimeric genetic construct. A chimeric genetic construct of the present disclosure may comprise, for example, nucleotide sequences encoding one or more antisense transcripts, one or more sense transcripts, one or more of each of the aforementioned, wherein all or part of a transcript therefrom is homologous to all or part of an RNA molecule comprising an RNA sequence encoded by a nucleotide sequence within the genome of an insect.

In one embodiment the disclosure transformation vector comprises an isolated and purified DNA molecule comprising a promoter operatively linked to one or more nucleotide sequences of the present disclosure. The nucleotide sequence is for example SEQ ID NO:1 or SEQ ID NO:2 or parts thereof. The nucleotide sequence includes a segment coding all or part of a RNA present within a targeted pest RNA transcript and may comprise inverted repeats of all or a part of a targeted pest RNA. The DNA molecule comprising the expression vector may also contain a functional intron sequence positioned either upstream of the coding sequence or even within the coding sequence, and may also contain a five prime (5') untranslated leader sequence (i.e., a UTR or 5'-UTR) positioned between the promoter and the point of translation initiation.

A plant transformation vector may contain sequences from more than one gene, thus allowing production of more than one dsRNA for inhibiting expression of two or more genes in cells of a target pest. One skilled in the art will readily appreciate that segments of DNA whose sequence corresponds to that present in different genes can be combined into a single composite DNA segment for expression in a transgenic plant. Alternatively, a plasmid of the present disclosure already containing at least one DNA segment can be modified by the sequential insertion of additional DNA segments between the enhancer and promoter and terminator sequences. In the insect control agent of the present disclosure designed for the inhibition of multiple genes, the genes to be inhibited can be obtained from the same insect species in order to enhance the effectiveness of the insect control agent. In certain embodiments, the genes can be derived from different insects in order to broaden the range of insects against which the agent is effective. When multiple genes are targeted for suppression or a combination of expression and suppression, a polycistronic DNA element can be fabricated as illustrated and disclosed in Fillatti, Application Publication No. US 2004-0029283.

Promoters that function in different plant species are also well known in the art. Promoters useful for expression of polypeptides in plants include those that are inducible, viral, synthetic, or constitutive as described in Odell et al. (1985), and/or promoters that are temporally regulated, spatially regulated, and spatio-temporally regulated. Preferred promoters include the enhanced CaMV35S promoters, the SUC2 promoter and the FMV35S promoter. For the purpose of the present disclosure, e.g., for optimum control of species that feed from the phloem via their stylet, it may be preferable to achieve the highest levels of expression of these genes within the phloems of plants. Therefore, in an advantageous embodiment the promoter is active in the phloem of a crop plant like the CaMV 35S promoter (Yang and Christou, 1990) and the SUC2 promoter (Truermit and Sauer, 1995). dsRNA expression control by the CaMV 35S promoter was used by Pitino et al. (2011) that demonstrated host induced gene silencing (HIGS) in aphids.

The phloem located expression of target specific dsRNA or siRNA in genetically modified plants that targets SHP allows most likely the reduction of infestation of crop plants by aphids and other plant sucking insects of the groups Sternorryhncha and Fulgoromorpha under the critical economic threshold, which is declared aim of IPS. In this context varying length of dsRNA and siRNA are possible that cover different regions of SHP mRNA.

A recombinant DNA vector or construct of the present disclosure will typically comprise a selectable marker that confers a selectable phenotype on plant cells. Selectable markers may also be used to select for plants or plant cells that contain the exogenous nucleic acids encoding polypeptides or proteins of the present disclosure. The marker may encode biocide resistance, antibiotic resistance (e.g., kanamycin, G418 bleomycin, hygromycin, etc.), or herbicide resistance (e.g., glyphosate, etc.).

Examples of selectable markers include, but are not limited to, a neo gene which codes for kanamycin resistance and can be selected for using kanamycin, G418, etc., a bar gene which codes for bialaphos resistance; a mutant EPSP synthase gene which encodes glyphosate resistance; a nitrilase gene which confers resistance to bromoxynil; a mutant acetolactate synthase gene (ALS) which confers imidazolinone or sulfonylurea resistance; and a methotrexate resistant DHFR gene. Examples of such selectable markers are illustrated in U.S. Pat. Nos. 5,550,318; 5,633,435; 5,780,708 and 6,118,047.

A recombinant vector or construct of the present disclosure may also include a screenable marker. Screenable markers may be used to monitor expression. Exemplary screenable markers include a [beta]-glucuronidase or uidA gene (GUS) which encodes an enzyme for which various chromogenic substrates are known (Jefferson, 1987; Jefferson et al, 1987); an R-locus gene, which encodes a product that regulates the production of anthocyanin pigments (red color) in plant tissues (Dellaporta et al, 1988); a [beta]-lactamase gene (Sutcliffe et al, 1978), a gene which encodes an enzyme for which various chromogenic substrates are known (e.g., PADAC, a chromogenic cephalosporin); a luciferase gene (Ow et al, 1986) a xylE gene (Zukowsky et al, 1983) which encodes a catechol dioxygenase that can convert chromogenic catechols; an [alpha]-amylase gene (Bcatu et al, 1990); a tyrosinase gene (Katz et al, 1983) which encodes an enzyme capable of oxidizing tyrosine to DOPA and dopaquinone which in turn condenses to melanin; an α-galactosidase, which catalyzes a chromogenic a-galactose substrate.

In some advantageous embodiments, the isolated polynucleotides according to the present disclosure are operably linked to a heterologous promoter and/or are defined as comprised on a plant transformation vector.

Preferred plant transformation vectors include those derived from a Ti plasmid of *Agrobacterium tumefaciens* (e.g. U.S. Pat. Nos. 4,536,475, 4,693,977, 4,886,937, 5,501,967 and EP 0 122 791). *Agrobacterium rhizogenes* plasmids (or "Ri") are also useful and known in the art. Other preferred plant transformation vectors include those disclosed, e.g., by Herrera-Estrella (1983); Bevan (1983), Klee (1985) and EP 0 120 516. In an advantageous embodiment, the vector is a binary vector.

In general it is preferred to introduce a functional recombinant DNA at a non-specific location in a plant genome. In special cases it may be useful to insert a recombinant DNA construct by site-specific integration. Several site-specific recombination systems exist which are known to function implants include cre-lox as disclosed in U.S. Pat. No. 4,959,317 and FLP-FRT as disclosed in U.S. Pat. No. 5,527,695.

Suitable methods for transformation of host cells for use with the current plant are believed to include virtually any method by which DNA can be introduced into a cell, such as by direct delivery of DNA such as by PEG-mediated transformation of protoplasts (Omirulleh et al, 1993), by desiccation/inhibition-mediated DNA uptake (Potrykus et al, 1985), by electroporation (U.S. Pat. No. 5,384,253), by agitation with silicon carbide fibers (Kaeppler et al, 1990; U.S. Pat. Nos. 5,302,523; and 5,464,765), by *Agrobacterium*-mediated transformation (U.S. Pat. Nos. 5,591,616 and 5,563,055) and by acceleration of DNA coated particles (U.S. Pat. Nos. 5,550,318; 5,538,877; and 5,538,880), etc. Through the application of techniques such as these, the cells of virtually any species may be stably transformed. In the case of multicellular species, the transgenic cells may be regenerated into transgenic organisms. Methods for the creation of transgenic plants and expression of heterologous nucleic acids in plants in particular are known and may be used with the nucleic acids provided herein to prepare transgenic plants that exhibit reduced susceptibility to feeding by a target pest organism such as corn rootworms. Plant transformation vectors can be prepared, for example, by inserting the dsRNA producing nucleic acids disclosed herein into plant transformation vectors and introducing these into plants. One known vector system has been derived by modifying the natural gene transfer system of *Agrobacterium tumefaciens*. The natural system comprises large Ti (tumor-inducing)-plasmids containing a large segment, known as T-DNA, which is transferred to transformed plants. Another segment of the Ti plasmid, the vir region, is responsible for T-DNA transfer. The T-DNA region is bordered by terminal repeats, hi the modified binary vectors the tumor-inducing genes have been deleted and the functions of the vir region are utilized to transfer foreign DNA bordered by the T-DNA border sequences. The T-region may also contain a selectable marker for efficient recovery of transgenic plants and cells, and a multiple cloning site for inserting sequences for transfer such as a dsRNA encoding nucleic acid.

A transgenic plant formed using *Agrobacterium* transformation methods typically contains a single simple recombinant DNA sequence inserted into one chromosome and is referred to as a transgenic event. Such transgenic plants can be referred to as being heterozygous for the inserted exogenous sequence. A homozygous transgenic plant can be obtained by sexually mating (selfmg) an independent segregant transgenic plant to produce F1 seed. One fourth of the F1 seed produced will be homozygous with respect to the transgene. Germinating F1 seed results in plants that can be tested for heterozygosity or homozygosity, typically using a SNP assay or a thermal amplification assay that allows for the distinction between heterozygotes and homozygotes (i.e., a zygosity assay).

The methods and compositions of the present disclosure may be applied to any monocot and dicot plant, depending on the coleopteran pest control desired. Specifically, the plants are intended to include, without limitation, alfalfa, aneth, apple, apricot, artichoke, arugula, asparagus, avocado, banana, barley, beans, beet, blackberry, blueberry, broccoli, brussel sprouts, cabbage, canola, cantaloupe, carrot, cassava, cauliflower, celery, cherry, cilantro, citrus, Clementine, coffee, corn, cotton, cucumber, Douglas fir, eggplant, endive, escarole, eucalyptus, fennel, figs, gourd, grape, grapefruit, honey dew, jicama, kiwifruit, lettuce, leeks, lemon, lime, Loblolly pine, mango, melon, mushroom, nut, oat, okra, onion, orange, an ornamental plant, papaya, parsley, pea, peach, peanut, pear, pepper, persimmon, pine, pineapple, plantain, plum, pomegranate, poplar, potato, pumpkin, quince, radiata pine, radicchio, radish, raspberry, rice, rye, sorghum, Southern pine, soybean, spinach, squash, strawberry, sugarbeet, sugarcane, sunflower, sweet potato, sweetgum, tangerine, tea, tobacco, tomato, turf, a vine, watermelon, wheat, yams, and zucchini plants. Thus, a plant transformed with a recombinant DNA sequence of SEQ ID NO:1, or concatemer, fragment, or complement thereof, that is transcribed to produce at least one dsRNA molecule that functions when ingested by a coleopteran pest to inhibit the expression of a target gene in the pest is also provided by the plant. In particular embodiments, the recombinant DNA sequence is SEQ ID NO:2, or fragments, complements, or concatemers thereof.

However, the polynucleotide according to the present disclosure may be transformed, transduced or transfected via a recombinant DNA vector also in a prokaryotic cell or eukaryotic cell, for example for production of an agent (pesticide) containing the SHP inhibitor.

A recombinant DNA vector may, for example, be a linear or a closed circular plasmid. The vector system may be a single vector or plasmid or two or more vectors or plasmids that together contain the total DNA to be introduced into the genome of the bacterial host. In addition, a bacterial vector may be an expression vector. The nucleic acid molecules according to the present disclosure can, for example, be suitably inserted into a vector under the control of a suitable promoter that functions in one or more microbial hosts to drive expression of a linked coding sequence or other DNA sequence. Many vectors are available for this purpose, and selection of the appropriate vector will depend mainly on the size of the nucleic acid to be inserted into the vector and the particular host cell to be transformed with the vector. Each vector contains various components depending on its function (amplification of DNA or expression of DNA) and the particular host cell with which it is compatible. The vector components for bacterial transformation generally include, but are not limited to, one or more of the following: a signal sequence, an origin of replication, one or more selectable marker genes, and an inducible promoter allowing the expression of exogenous DNA.

F. Target Gene Suppression

The present disclosure provides, as an example, a transformed host or symbiont pest target organism, transformed plant cells and transformed plants and their progeny. The transformed plant cells and transformed plants may be engineered to express one or more of the dsRNA or siRNA sequences described herein to provide a pest-protective effect. These sequences may be used for SHP gene suppression in a SHP expressing pest organism, thereby reducing the predation by the pest on a protected transformed host or symbiont organism. As used herein the words "gene suppression" are intended to refer to any of the well-known methods for reducing the levels of gene transcription to mRNA and/or subsequent translation of the mRNA.

Gene suppression is also intended to mean the reduction of protein expression from a gene or a coding sequence including posttranscriptional gene suppression and transcriptional suppression. Posttranscriptional gene suppression is mediated by the homology between of all or a part of a mRNA transcribed from a gene or coding sequence targeted for suppression and the corresponding double stranded RNA used for suppression, and refers to the substantial and measurable reduction of the amount of available mRNA available in the cell for binding by ribosomes. The transcribed RNA can be in the sense orientation to effect what is called co-suppression, in the anti-sense orientation to effect what is called anti-sense suppression, or in both orientations producing a dsRNA to effect what is called RNA interference (RNAi).

Transcriptional suppression is mediated by the presence in the cell of a dsRNA gene suppression agent exhibiting substantial sequence identity to a promoter DNA sequence or the complement thereof to effect what is referred to as promoter trans suppression. Gene suppression may be effective against a native plant gene associated with a trait, e.g., to provide plants with reduced levels of a protein encoded by the native gene or with enhanced or reduced levels of an affected metabolite. Gene suppression can also be effective against target genes in plant pests that may ingest or contact plant material containing gene suppression agents, specifically designed to inhibit or suppress the expression of one or more homologous or complementary sequences in the cells of the pest. Post-transcriptional gene suppression by antisense or sense oriented RNA to regulate gene expression in plant cells is disclosed in U.S. Pat. Nos. 5,107,065, 5,759, 829, 5,283,184, and 5,231,020. The use of dsRNA to suppress genes in plants is disclosed in WO 99/53050, WO 99/49029, U.S. Patent Application Publication No. 2003/0175965, and 2003/0061626, U.S. patent application Ser. No. 10/465,800, and U.S. Pat. Nos. 6,506,559, and 6,326, 193.

A beneficial method of post transcriptional gene suppression in plants employs both sense-oriented and anti-sense-oriented, transcribed RNA which is stabilized, e.g., as a hairpin and stem and loop structure. A preferred DNA construct for effecting post transcriptional gene suppression is one in which a first segment encodes an RNA exhibiting an anti-sense orientation exhibiting substantial identity to a segment of a gene targeted for suppression, which is linked to a second segment in sense orientation encoding an RNA exhibiting substantial complementarity to the first segment. Such a construct forms a stem and loop structure by hybridization of the first segment with the second segment and a loop structure from the nucleotide sequences linking the two segments (see WO94/01550, WO98/05770, US 2002/0048814, and US 2003/0018993).

According to one embodiment of the present disclosure, there is provided a nucleotide sequence, for which in vitro expression results in transcription of a stabilized RNA sequence that is substantially homologous to an RNA molecule of a targeted gene in an insect that comprises an RNA sequence encoded by a nucleotide sequence within the genome of the insect. Thus, after the insect ingests the stabilized RNA sequence incorporated in a diet or sprayed on a plant surface, a down-regulation of the nucleotide sequence corresponding to the target gene in the cells of a target insect is affected.

Inhibition of the SHP target gene using the stabilized dsRNA technology of the present disclosure is sequence-specific in that nucleotide sequences corresponding to the duplex region of the RNA are targeted for genetic inhibition. RNA containing a nucleotide sequences identical to a portion of the target gene is preferred for inhibition. RNA sequences with insertions, deletions, and single point mutations relative to the target sequence have also been found to be effective for inhibition. In performance of the present disclosure, it is preferred that the inhibitory dsRNA and the portion of the target gene share at least from about 80% sequence identity, or from about 90% sequence identity, or from about 95% sequence identity, or from about 99% sequence identity, or even about 100% sequence identity. Alternatively, the duplex region of the RNA may be defined functionally as a nucleotide sequence that is capable of hybridizing with a portion of the target gene transcript. A less than MI length sequence exhibiting a greater homology compensates for a longer less homologous sequence. The length of the identical nucleotide sequences may be at least about 25, 50, 100, 200, 300, 400, 500 or at least about 1000 bases. Normally, a sequence of greater than 20-100 nucleotides should be used, though a sequence of greater than about 200-300 nucleotides would be preferred, and a sequence of greater than about 500-1000 nucleotides would be especially preferred depending on the size of the target gene. The plant has the advantage of being able to tolerate sequence variations that might be expected due to genetic mutation, strain polymorphism, or evolutionary divergence. The introduced nucleic acid molecule may not need to be absolute homology, may not need to be full length, relative to either the primary transcription product or fully processed mRNA of the target gene. Therefore, those skilled in the art need to realize that, as disclosed herein, 100% sequence identity between the RNA and the target gene is not required to practice the present disclosure. Inhibition of target gene expression may be quantified by measuring either the endogenous target RNA or the protein produced by translation of the target RNA and the consequences of inhibition can be confirmed by examination of the outward properties of the cell or organism. Techniques for quantifying RNA and proteins are well known to one of ordinary skill in the art. Multiple selectable markers are available that confer resistance to ampicillin, bleomycin, chloramphenicol, gentamycin, hygromycin, kanamycin, lincomycin, methotrexate, phosphinothricin, puromycin, spectinomycin, rifampicin, and tetracyclin, and the like.

In certain embodiments gene expression is inhibited by at least 10%, preferably by at least 33%, more preferably by at least 50%, and yet more preferably by at least 80%. In particularly preferred embodiments of the plant gene expression is inhibited by at least 80%, more preferably by at least 90%, more preferably by at least 95%, or by at least 99% within cells in the insect so a significant inhibition takes place. Significant inhibition is intended to refer to sufficient inhibition that results in a detectable phenotype (e.g., cessation of larval growth, paralysis or mortality, etc.) or a detectable decrease in RNA and/or protein corresponding to the target gene being inhibited. Although in certain embodiments of the disclosure inhibition occurs in substantially all cells of the insect, in other preferred embodiments inhibition occurs in only a subset of cells expressing the gene. For example, if the gene to be inhibited plays an essential role in cells in the insect alimentary tract, inhibition of the gene within these cells is sufficient to exert a deleterious effect on the insect. dsRNA molecules may be synthesized either in vivo or in vitro. The dsRNA may be formed by a single self-complementary RNA strand or from two complementary RNA strands. Endogenous RNA polymerase of the cell may mediate transcription in vivo, or cloned RNA polymerase can be used for transcription in vivo or in vitro. Inhibition may be targeted by specific transcription in an organ, tissue, or cell type; stimulation of an environmental condition (e.g., infection, stress, temperature, chemical inducers); and/or engineering transcription at a developmental stage or age. The RNA strands may or may not be polyadenylated; the RNA strands may or may not be capable of being translated into a polypeptide by a cell's translational apparatus.

A RNA, dsRNA, siRNA, or miRNA of the present disclosure may be produced chemically or enzymatically by one skilled in the art through manual or automated reactions or in vivo in another organism. RNA may also be produced by partial or total organic synthesis; any modified ribonucleotide can be introduced by in vitro enzymatic or organic synthesis. The RNA may be synthesized by a cellular RNA polymerase or a bacteriophage RNA polymerase (e.g., T3, T7, SP6). The use and production of an expression construct are known in the art (see, for example, WO 97/32016; U.S. Pat. Nos. 5,593,874, 5,698,425, 5,712,135, 5,789,214, and 5,804,693). If synthesized chemically or by in vitro enzymatic synthesis, the RNA may be purified prior to introduction into the cell. For example, RNA can be purified from a mixture by extraction with a solvent or resin, precipitation, electrophoresis, chromatography, or a combination thereof. Alternatively, the RNA may be used with no or a minimum of purification to avoid losses due to sample processing. The RNA may be dried for storage or dissolved in an aqueous solution. The solution may contain buffers or salts to promote annealing, and/or stabilization of the duplex strands.

For transcription from a transgene in vivo or an expression construct, a regulatory region (e.g., promoter, enhancer, silencer, and polyadenylation) may be used to transcribe the RNA strand (or strands). Therefore, in one embodiment, the nucleotide sequences for use in producing RNA molecules may be operably linked to one or more promoter sequences functional in a microorganism, a fungus or a plant host cell. Ideally, the nucleotide sequences are placed under the control of an endogenous promoter, normally resident in the host genome. The nucleotide sequence of the present disclosure, under the control of an operably linked promoter sequence, may further be flanked by additional sequences that advantageously affect its transcription and/or the stability of a resulting transcript. Such sequences are generally located upstream of the operably linked promoter and/or downstream of the 3' end of the expression construct and may occur both upstream of the promoter and downstream of the 3' end of the expression construct, although such an upstream sequence only is also contemplated.

The present disclosure provides for inhibiting gene expression of one or multiple target genes in a target pest using stabilized dsRNA methods. The plant is particularly useful in the modulation of eukaryotic gene expression, in particular the modulation of expression of genes present in pests that exhibit a digestive system pH level that is from about 4.5 to about 9.5, more preferably from about 5.0 to about 8.0, and even more preferably from about 6.5 to about 7.5. For plant pests with a digestive system that exhibits pH levels outside of these ranges, delivery methods may be desired for uses that do not require ingestion of dsRNA molecules.

The modulatory effect of dsRNA is applicable to a variety of genes expressed in the pests including, for example, endogenous genes responsible for cellular metabolism or cellular transformation, including house-keeping genes, transcription factors and other genes which encode polypeptides involved in cellular metabolism.

The present disclosure provides in part a delivery system for the delivery of the insect control agents to insects through their exposure to a diet containing the insect control agents of the present disclosure. In accordance with one of the embodiments, the stabilized dsRNA or siRNA molecules may be incorporated in the insect diet or may be overlaid on the top of the diet for consumption by an insect. The present disclosure also provides in part a delivery system for the delivery of the insect control agents to insects through their exposure to a microorganism or host such as a plant containing the insect control agents of the present disclosure by ingestion of the microorganism or the host cells or the contents of the cells. In accordance with another embodiment, the present disclosure involves generating a transgenic plant cell or a plant that contains a recombinant DNA construct transcribing the stabilized dsRNA molecules of the present disclosure. As used herein, the phrase "generating a transgenic plant cell or a plant" refers to the methods of employing the recombinant DNA technologies readily available in the art (e.g., by Sambrook, et al, 1989) to construct a plant transformation vector transcribing the stabilized dsRNA molecules of the present disclosure, to transform the plant cell or the plant and to generate the transgenic plant cell or the transgenic plant that contain the transcribed, stabilized dsRNA molecules.

In still another embodiment, non-pathogenic, attenuated strains of microorganisms may be used as a carrier for the insect control agents and, in this perspective, the microorganisms carrying such agents are also referred to as insect control agents. The microorganisms may be engineered to express a nucleotide sequence of a target gene to produce RNA molecules comprising RNA sequences homologous or complementary to RNA sequences typically found within the cells of an insect. Exposure of the insects to the microorganisms result in ingestion of the microorganisms and down-regulation of expression of target genes mediated directly or indirectly by the RNA molecules or fragments or derivatives thereof.

The present disclosure alternatively provides exposure of an insect to the insect control agents of the present disclosure incorporated in a spray mixer and applied to the surface of a host, such as a host disclosure, hi an exemplary embodiment, ingestion of the insect control agents by an insect delivers the insect control agents to the gut of the insect and subsequently to the cells within the body of the insect. In another embodiment, infection of the insect by the insect control agents through other means such as by injection or other physical methods also permits delivery of the insect control agents. In yet another embodiment, the RNA molecules themselves are encapsulated in a synthetic matrix such as a polymer and applied to the surface of a host such as a plant. Ingestion of the host cells by an insect permits delivery of the insect control agents to the insect and results in down-regulation of a target gene in the host.

It is envisioned that the compositions of the present disclosure can be incorporated within the seeds of a plant species either as a product of expression from a recombinant gene incorporated into a genome of the plant cells, or incorporated into a coating or seed treatment that is applied to the seed before planting. The plant cell containing a recombinant gene is considered herein to be a transgenic event. It is believed that a pesticidal seed treatment can provide significant advantages when combined with a transgenic event that provides protection from coleopteran pest infestation that is within the preferred effectiveness range against a target pest. In addition, it is believed that there are situations that are well known to those having skill in the art, where it is advantageous to have such transgenic events within the preferred range of effectiveness.

The present disclosure provides in part a delivery system for the delivery of insect control agents to insects. The stabilized dsRNA or siRNA molecules of the present disclosure may be directly introduced into the cells of an insect, or introduced into an extracellular cavity, interstitial space, lymph system, digestive system, into the circulation of the insect through oral ingestion or other means that one skilled in the art may employ. Methods for oral introduction may include direct mixing of RNA with food of the insect, as well as engineered approaches in which a species that is used as food is engineered to express the dsRNA or siRNA, then fed to the insect to be affected. In one embodiment, for example, the dsRNA or siRNA molecules may be incorporated into, or overlaid on the top of, the insect's diet. In another embodiment, the RNA may be sprayed onto a plant surface. In still another embodiment, the dsRNA or siRNA may be expressed by microorganisms and the microorganisms may be applied onto a plant surface or introduced into a root, stem by a physical means such as an injection. In still another embodiment, a plant may be genetically engineered to express the dsRNA or siRNA in an amount sufficient to kill the insects known to infect the plant.

Specifically, in practicing the present disclosure in WCR, the stabilized dsRNA or siRNA may be introduced in the midgut inside the insect and achieve the desired inhibition of the targeted genes. The dsRNA or siRNA molecules may be incorporated into a diet or be overlaid on the diet as discussed above and may be ingested by the insects. In any event, the dsRNA's of the present disclosure are provided in the diet of the target pest. The target pest of the present disclosure will exhibit a digestive tract pH from about 4.5 to about 9.5, or from about 5 to about 8.5, or from about 6 to about 8, or from about 6.5 to about 7.7, or about 7.0. The digestive tract of a target pest is defined herein as the location within the pest that food that is ingested by the target pest is exposed to an environment that is favorable for the uptake of the dsRNA molecules of the present disclosure without suffering a pH so extreme that the hydrogen bonding between the double-strands of the dsRNA are caused to dissociate and form single stranded molecules.

It is also anticipated that dsRNA's produced by chemical or enzymatic synthesis may be formulated in a manner consistent with common agricultural practices and used as spray-on products for controlling insect infestations. The formulations may include the appropriate stickers and wetters required for efficient foliar coverage as well as UV protectants to protect dsRNAs from UV damage. Such additives are commonly used in the bio-insecticide industry and are well known to those skilled in the art. Such applications could be combined with other spray-on insecticide applications, biologically based or not, to enhance plant protection from insect feeding damage.

The present inventors contemplate that bacterial strain producing insecticidal proteins may be used to produce dsRNAs for insect control purposes. These strains may exhibit improved insect control properties. A variety of different bacterial hosts may be used to produce insect control dsRNAs. Exemplary bacteria may include *E. coli*, *B. thuringiensis*, *Pseudomonas* sp., *Photorhabdus* sp., *Xenorhabdus* sp., *Serratia entomophila* and related *Serratia* sp., *B. sphaericus*, *B. cereus*, *B. laterosporus*, *B. popilliae*, *Clostridium bifermentans* and other *Clostridium* species, or other spore-forming gram-positive bacteria. In certain embodiments, bacteria may be engineered for control of pests such as mosquitoes.

The present plant also relates to recombinant DNA constructs for expression in a microorganism. Exogenous nucleic acids from which a RNA of interest is transcribed can be introduced into a microbial host cell, such as a bacterial cell or a fungal cell, using methods known in the art.

The nucleotide sequences of the present disclosure may be introduced into a wide variety of prokaryotic and eukaryotic microorganism hosts to produce the stabilized dsRNA or siRNA molecules.

F. Transgenic Plants

Another aspect of the present disclosure relates to a transgenic plant and seeds. A gene coding an inhibitor against the SHP of the target pest has been introduced into the transgenic plant of the present disclosure. Typically, the transgenic plant of the present disclosure has been subjected to gene modification so as to express: (A) a dsRNA molecule, wherein the dsRNA may be modified in the plant through an enzymatic process so that siRNA molecules may be generated targeting a transcript product of a gene coding the SHP of the target pest; (B) an antisense nucleic acid targeted at the transcript product of a gene coding the SHP of the target pest; or (C) a ribozyme targeted at the transcript product of a gene coding the SHP of the target pest.

As mentioned above, the present disclosure provides seeds and plants having one or more transgenic event. Combinations of events are referred to as "stacked" transgenic events. These stacked transgenic events can be events that are directed at the same target pest, or they can be directed at different target pests. In one embodiment, a seed having the ability to express a nucleic acid provided herein also has the ability to express at least one other insecticidal agent, including, but not limited to, an RNA molecule the sequence of which is derived from the sequence of an RNA expressed in a target pest and that forms a double stranded RNA structure upon expressing in the seed or cells of a plant grown from the seed, wherein the ingestion of one or more cells or the cell content of the plant by the target pest results in the suppression of expression of the RNA in the cells of the target pest. In further embodiments, a seed having the ability to express a dsRNA the sequence of which is derived from a target pest also has a transgenic event that provides herbicide tolerance. One beneficial example of a herbicide tolerance gene provides resistance to glyphosate, N-(phosphonomethyl) glycine, including the isopropylamine salt form of such herbicide.

In the present method, combination of expression of an insecticidal amount of a dsRNA within the cells of a transgenic seed or plant grown from the seed coupled with treatment of the seed or plant with certain chemical or protein pesticides may be used to provide unexpected synergistic advantages, including unexpectedly superior efficacy for protection against damage to the resulting transgenic plant by the target pest. In particular embodiments, treatment of a transgenic seed that is capable of expressing certain constructs that form dsRNA molecules, the sequence of which are derived from one or more sequences expressed in a corn rootworm, with from about 100 gm to about 400 gm of pesticide per 100 kg of seed provides unexpectedly superior protection against corn rootworm. In addition, it is believed that such combinations are also effective to protect the emergent plants against predation by other pests. The seeds of the present disclosure may also be used to decrease the cost of pesticide use, because less pesticide can be used to obtain a required amount of protection than when such methods are not used. Moreover, because less pesticide is used and because it is applied prior to planting and without a separate field application, it is believed that the subject method is therefore safer to the operator and to the environment, and is potentially less expensive than conventional methods.

Pesticides and insecticides that are useful in compositions in combination with the methods and compositions of the present disclosure, including as seed treatments and coatings as well as methods for using such compositions can be found, for example, in U.S. Pat. No. 6,551,962, the entirety of which is incorporated herein by reference.

It is anticipated that the combination of certain stabilized dsRNA constructs with one or more insect control protein genes will result in synergies that enhance the insect control phenotype of a transgenic plant. Insect bioassays employing artificial diet- or whole plant tissue can be used to define dose-responses for larval mortality or growth inhibition using both dsRNAs and insect control proteins. One skilled in the art can test mixtures of dsRNA molecules and insect control proteins in bioassay to identify combinations of actives that are synergistic and desirable for deployment in insect-protected plants (Tabashnik, 1992). Synergy in killing insect pests has been reported between different insect control proteins (for review, see Schnepf et al., 1998). It is anticipated that synergies will exist between certain dsRNAs and between certain dsRNAs and certain insect control proteins.

The disclosure also relates to commodity products containing one or more of the sequences of the present disclosure, and produced from a recombinant plant or seed containing one or more of the nucleotide sequences of the present disclosure are specifically contemplated as embodiments of the present disclosure. A commodity product containing one or more of the sequences of the present disclosure is intended to include, but not be limited to, meals, oils, crushed or whole grains or seeds of a plant, or any food product comprising any meal, oil, or crushed or whole grain of a recombinant plant or seed containing one or more of the sequences of the present disclosure. The detection of one or more of the sequences of the present disclosure in one or more commodity or commodity products contemplated herein is defacto evidence that the commodity or commodity product is composed of a transgenic plant designed to express one or more of the nucleotide.

H. Obtaining Nucleic Acids

Some embodiments pertain to isolated and purified nucleotide sequences as SHP inhibitors that may be used as the insect control agents.

Therefore, the present disclosure provides a method for obtaining a nucleic acid comprising a nucleotide sequence for producing a dsRNA or siRNA. In one embodiment, such a method for obtaining a nucleic acid fragment comprises a nucleotide sequence for producing a substantial portion of a dsRNA or siRNA comprises: (a) synthesizing first and a second oligonucleotide primers corresponding to a portion of one of the nucleotide sequences from a targeted insect; and (b) amplifying a cDNA or gDNA template in a cloning vector using the first and second oligonucleotide primers of step (a) wherein the amplified nucleic acid molecule transcribes a substantial portion of a dsRNA or siRNA of the present invention. The preferred target genes of the present disclosure are genes encoding SHP.

In one embodiment, a gene is selected that is expressed in the insect gut. Targeting genes expressed in the gut avoids the requirement for the dsRNA to spread within the insect. Target genes for use in the present invention may include, for example, those that share substantial homologies to the nucleotide sequences of known gut-expressed genes that encode protein components of the vacuolar and plasma membrane proton V-ATPase (Dow et al., 1997; Dow, 1999). This protein complex is the sole energizer of epithelial ion transport and is responsible for alkalinization of the midgut lumen. The V-ATPase is also expressed in the Malpighian tubule, an outgrowth of the insect hindgut that functions in fluid balance and detoxification of foreign compounds in a manner analogous to a kidney organ of a mammal. In another embodiment, the V-ATPase may be Vha68-2, or a homolog or ortholog thereof (e.g. as found in SEQ ID NO:821).

For the purpose of the present invention, the dsRNA or siRNA molecules may be obtained from a SHP encoding DNA or RNA by polymerase chain (PCR) amplification of a target SHP gene sequences.

Nucleic acid molecules and fragments thereof from amphids, or other Hemiptera pest species may be employed to obtain other nucleic acid molecules from other species for use in the present disclosure to produce desired dsRNA and siRNA molecules. Such nucleic acid molecules include the nucleic acid molecules that encode the complete coding sequence of a protein and promoters and flanking sequences of such molecules. In addition, such nucleic acid molecules include nucleic acid molecules that encode for gene family members. Such molecules can be readily obtained by using the above-described nucleic acid molecules or fragments thereof to screen, for instance, cDNA or gDNA libraries. Methods for forming such libraries are well known in the art.

In order to obtain a DNA segment from the corresponding SHP gene in an insect species, PCR primers may be designed based on the sequence as found in the insects from which the SHP gene has been cloned. The primers are designed to amplify a DNA segment of sufficient length for use in the present disclosure. DNA (either genomic DNA or cDNA) is prepared from the insect species, and the PCR primers are used to amplify the DNA segment. Amplification conditions are selected so that amplification will occur even if the primers do not exactly match the target sequence. Alternately, the gene (or a portion thereof) may be cloned from a gDNA or cDNA library prepared from the insect pest species, using the SHP gene or another known insect gene as a probe. Techniques for performing PCR and cloning from libraries are known. Further details of the process by which DNA segments from target insect pest species may be isolated based on the sequence of the SHP genes previously cloned from *Acyrtosiphon pisum* or other insect species are provided in the Examples. One of ordinary skill in the art will recognize that a variety of techniques may be used to isolate gene segments from insect pest species that correspond to genes previously isolated from other species.

The described agro-biotechnological approach of HIGS of SHP in crops (e.g. wheat, cotton, beans, potatoe and tomato), where plant sucking insects of the groups Sternorryhncha and Fulgoromorpha are relevant pests on, can be used to control these in the field as well as in the greenhouse. The development of resistances by pests, observed many times by varies insects (mentioned above), can be excluded on the current state of knowledge. Off-target effects on other insects can actually be excluded because no hits were detected by BLAST search in mRNA sequences of available organisms (Carolan J C et al., 2009).

I. Figures

FIG. 1 shows the Influence of SHP silencing on sheath formation of *Acyrthosiphon pisum*. Salivary sheaths from untreated aphids reared on an artificial diet (a, b) show a typical necklace structure and the sheaths are wider at the stylet penetration site (white arrow) than at the tip. Each bead represents one gel saliva secretion event (white arrowheads). Aphids injected with IMPI dsRNA form similar sheaths (c, d). The hole caused by stylet penetration through the Parafilm sheet is visible (white arrows). SHP silencing disrupts sheath formation (e-h). In aphids injected with 25 ng dsRNA (e, f) the first two beads are clear and the next 4-5 appear less distinct. Additional gel saliva material appears to be distributed over the surrounding Parafilm sheet surface. In aphids injected with 50 ng dsRNA there are no visible beads (g, h) and only a small amount of gel saliva material covering the hole in the sheet (white arrow).

Figure 2:
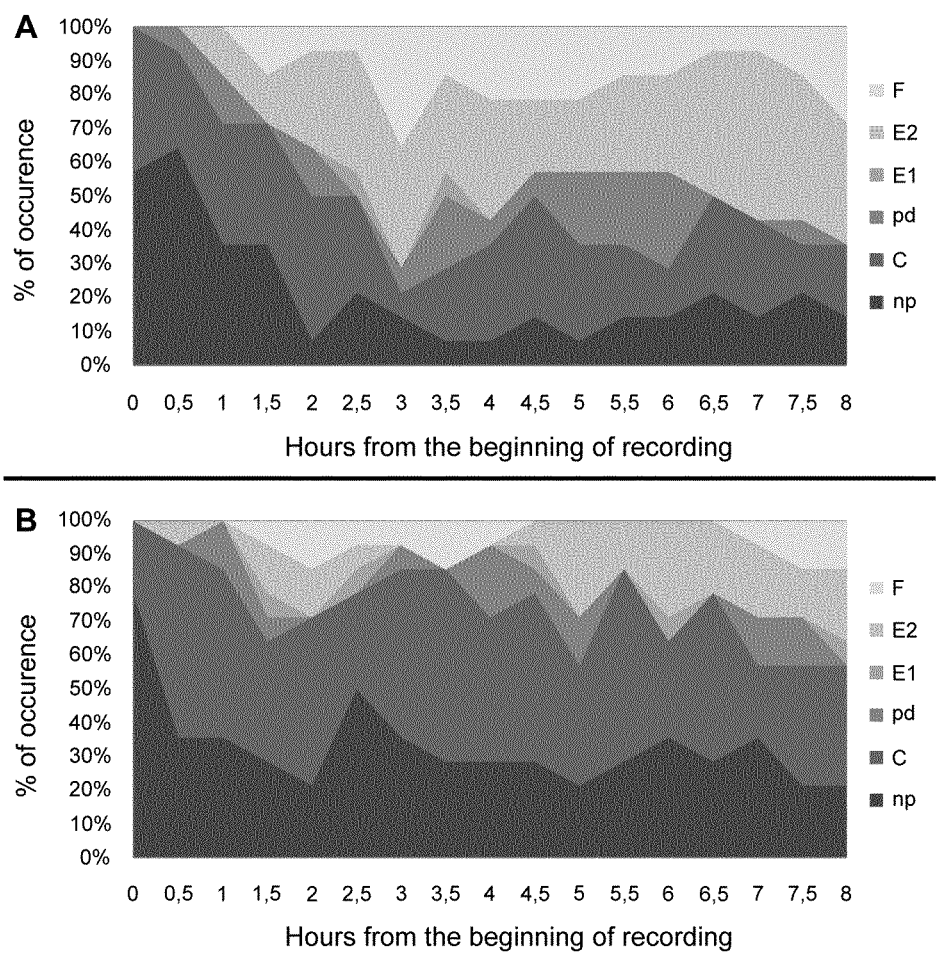
FIG. 2 are two diagrams showing the temporal evolution of behavior (EPG wavepatterns) SHP RNAi (B) aphids and (A) controls.

FIG. 2 shows the temporal evolution of behavior (waveforms) of SHP RNAi aphids and controls of the aphid species *Acyrthosiphon pisum*. The percentage of individuals in the control group (a) and the SHP RNAi group (b) is shown demonstrating specific behaviors at 30 min intervals over a total recording time of 8 hours. Behavior of 14-16 aphids was observed for each treatment.

Figure 3:
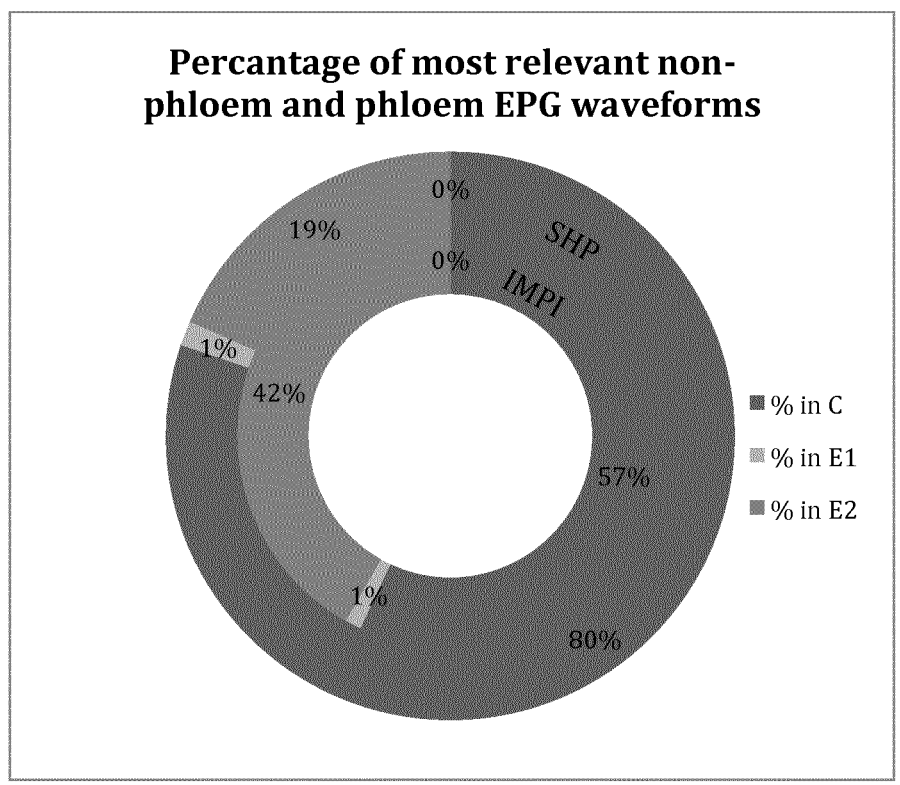
FIG. 3 is a diagram showing percentage of important non-phloematic and phloematic EPG wavepatterns.

FIG. 3 shows a comparison of most relevant aphid behavior of *Acyrthosiphon pisum*. In comparison with control injected aphids (IMPI), SHP silenced aphids show a higher percentage of stylet movement (C) and reduced ingestion (E2). Secretion of watery saliva (E1) does not differ.

Figure 4:
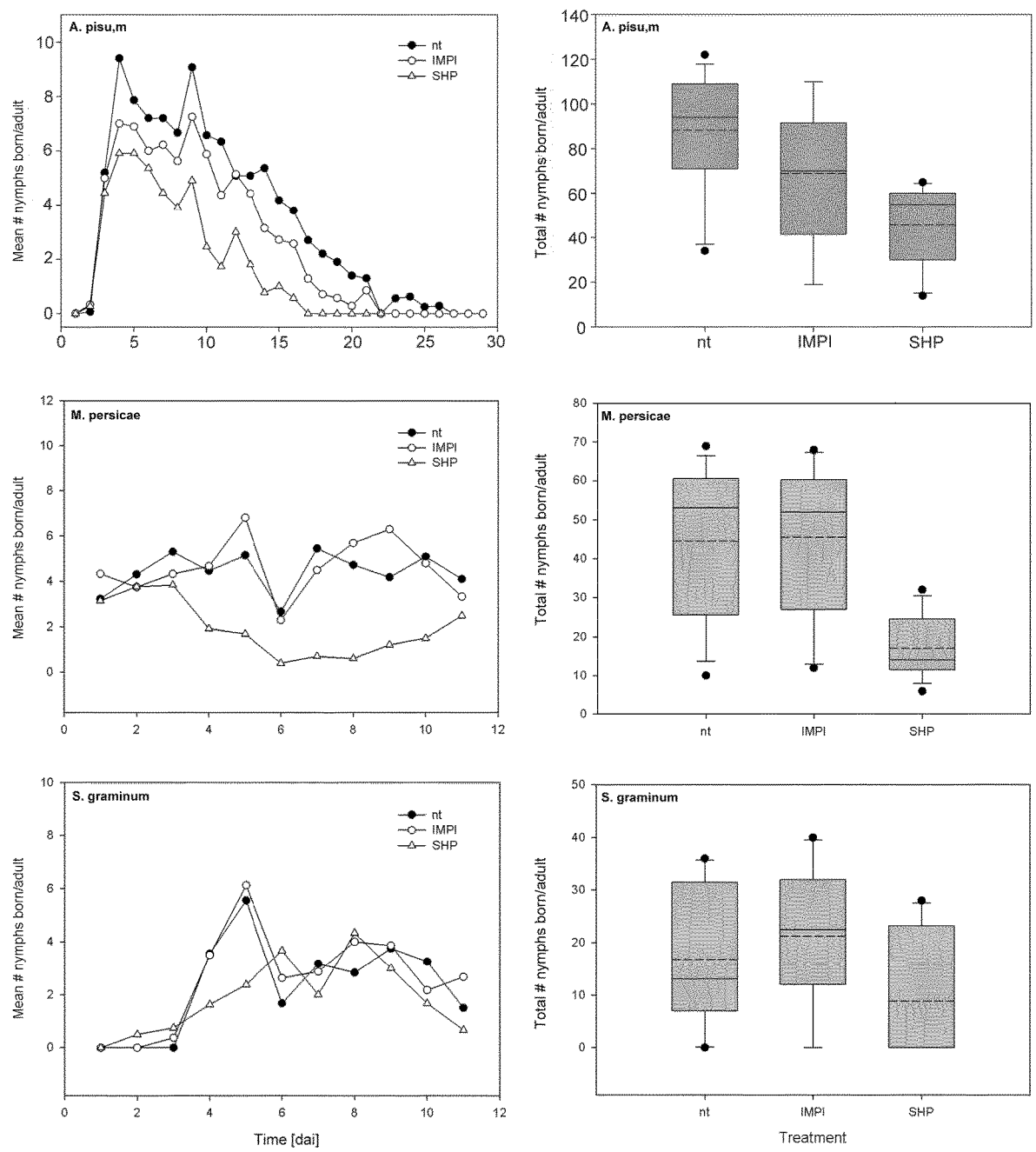
FIG. 4 is are two diagrams showing the reproduction SHP RNAi aphids and controls.

FIG. 4 shows the reproduction of SHP RNAi aphids (dsRNA applied by injection) and controls of the aphid species *Acyrthosiphon pisum*, *Myzus persicae* and *Schizaphis graminum*. Each group contained 10-15 aphids and the experiment was repeated three times. (Left) The SHP RNAi aphids show a lower reproduction rate 4 days after dsRNA injection (dai). Aphids of the species *Acyrthosiphon pisum* that were observed over their whole lifetime show a shorter overall duration of reproduction than untreated and IMPI RNAi controls. (Right) The total reproduction of the SHP RNAi aphids is significantly lower than that of the control groups.

Figure 5:
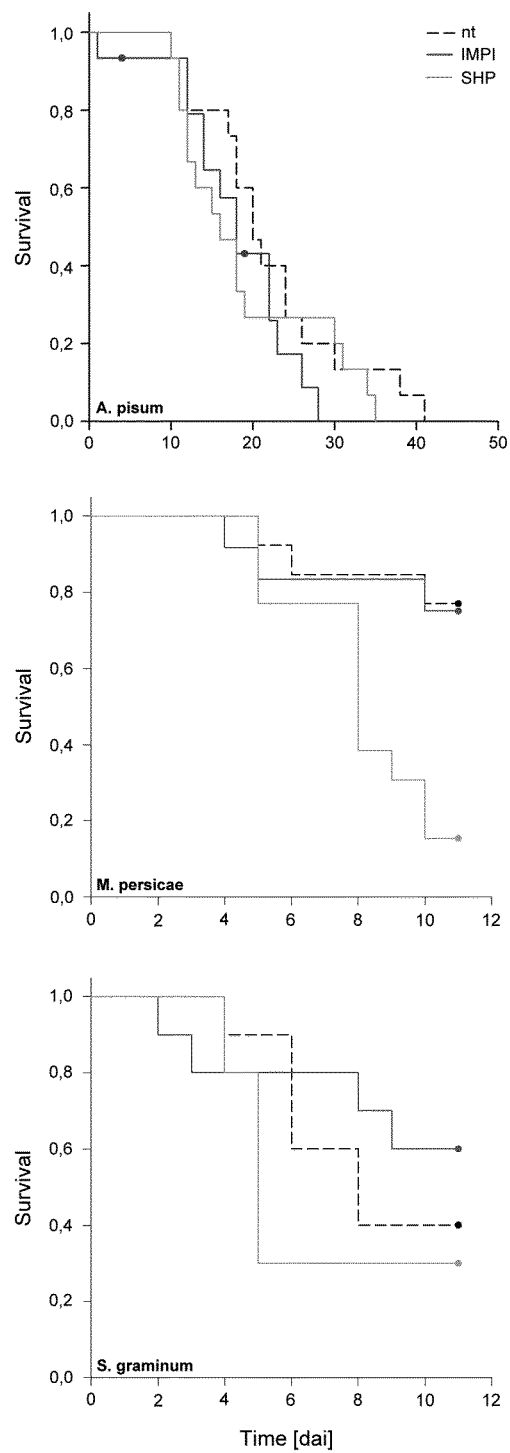
FIG. 5 is a diagram showing the survival analysis of SHP RNAi aphids and controls by Kaplan Meier Log-Rank.

FIG. 5 shows the survival of SHP RNAi aphids and controls (given as dai—days after injection) of the aphid species *Acyrthosiphon pisum* (N=3), *Myzus persicae* (N=1) and *Schizaphis graminum* (N=1) by Kaplan Meier Log-Rank. Aphids that were alive at the end of the observation time or died for unrelated reasons are censored (black circles). Each group contained 10-15 aphids. While aphids of the species *Acyrthosiphon pisum* do not show differences between SHP RNAi aphids and controls, *Myzus persicae* and *Schizaphis graminum* showed reduced survival for SHP RNAi aphids.

FIG. 6 displays a part of the mRNA sequence encoding *Acyrthosiphon pisum* SHP

Figure 8:
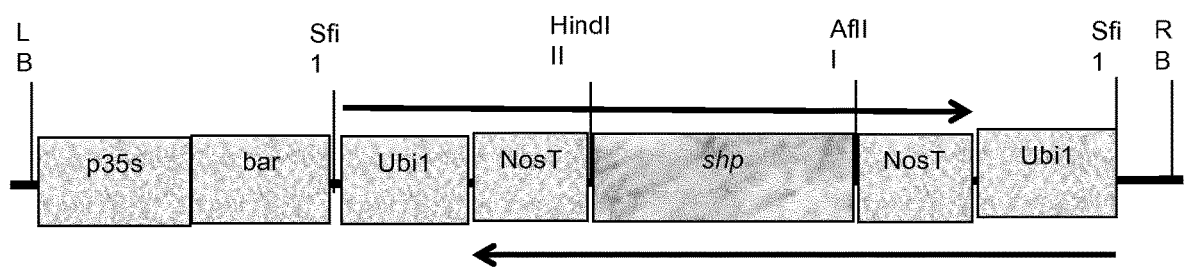
FIG. 8 shows a partial plasmid vector map where the GUS from p71-Ubi-RNAi vector was replaced by shp template (FIG. 7) resulting in p7i Ubi-shp-RNAi.

FIG. 7 displays a ribonucleic acid sequence of a dsRNA (SEQ ID NO.2) derived from SEQ ID NO. 1 exemplarily used for *Acyrhtosiphon pisum* pest control in vitro and in planta FIG. 8 shows a partial plasmid vector map where the GUS from p71-Ubi-RNAi vector was replaced by shp template (FIG. 7) resulting in p7i Ubi-shp-RNAi.

Figure 9:
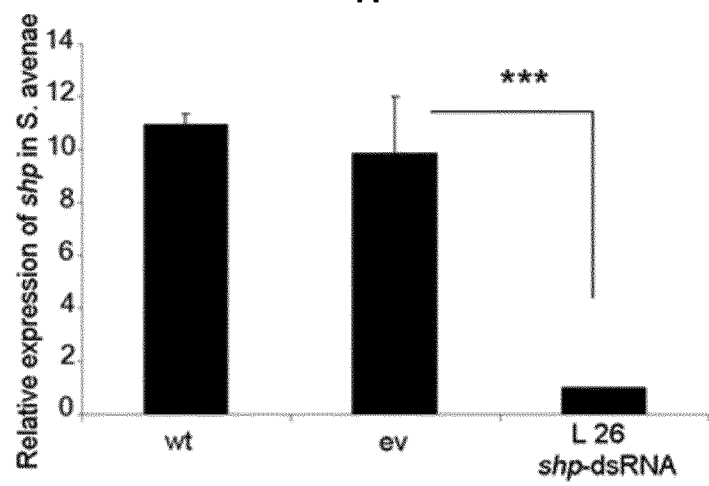
FIG. 9 are diagrams showing the quantification of shp transcripts in the aphid species *Sitobion avenae* by qRT-PCR feeding on control plants (wt—wild type; ev—empty vector) and shp-dsRNA expressing plants. (a) Relative quantification of shp transcripts after 2 weeks feeding on L26, ev, and wt lines. The reduction in shp expression in aphids that were feeding on shp-dsRNA plant line L26 compared to the wt and ev controls is statistically significant. (b) Multitude of shp transcripts after feeding for 2 weeks on shp-dsRNA lines and subsequently feeding on wt for 1 or 2 weeks. The reduction in shp expression in the aphid fed on L26 compared to controls is statistically significant. Bars indicate mean values±standard deviation of three independent sample collections.
Figure 9:
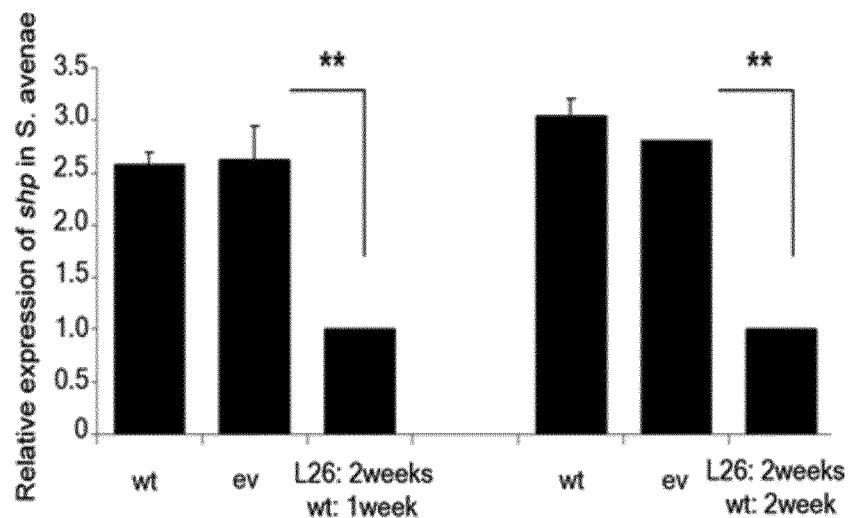

FIG. 9 shows quantification of shp transcripts in the aphid species *Sitobion avenae* by qRT-PCR feeding on control plants (wt—wild type; ev—empty vector) and shp-dsRNA expressing plants. (a) Relative quantification of shp transcripts after 2 weeks feeding on L26, ev, and wt lines. The reduction in shp expression in aphids that were feeding on shp-dsRNA plant line L26 compared to the wt and ev controls is statistically significant. (b) Multitude of shp transcripts after feeding for 2 weeks on shp-dsRNA lines and subsequently feeding on wt for 1 or 2 weeks. The reduction in shp expression in the aphid fed on L26 compared to controls is statistically significant. Bars indicate mean values±standard deviation of three independent sample collections.

Figure 10:
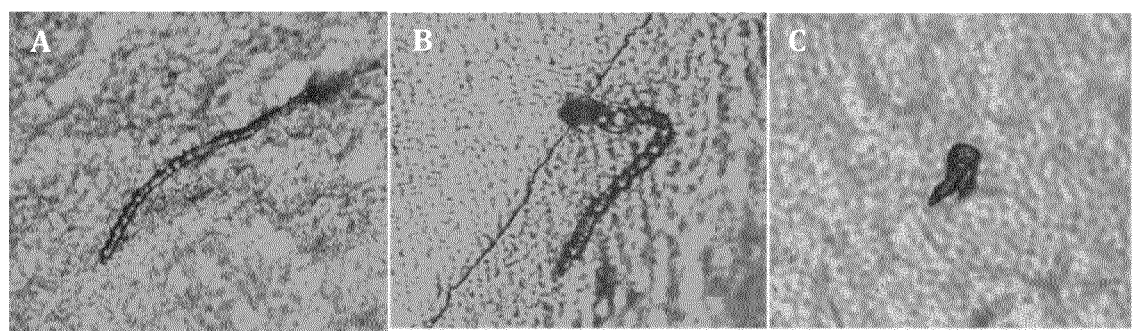
FIG. 10 shows the influence of shp silencing on salivary sheath formation of *Sitobion avenae*. Salivary sheaths from aphids feeding from wild type (a) and empty vector (b)

FIG. 10 shows the influence of shp silencing on salivary sheath formation of *Sitobion avenae*. Salivary sheaths from aphids feeding from wild type (a) and empty vector (b) controls for two weeks and on artificial diet for two days show a typical necklace structure (compare FIG. 1). (c) Formation of salivary sheaths from aphids feeding for two weeks on shp-dsRNA plant line L26 is disrupted in artificial diet.

FIG. 11 shows the reproduction of aphids from the species *Sitobion avenae* during infestation on control (wt—wild type; ev—empty vector) and shp-dsRNA expressing plants respectively. Each group contained 15 aphids. (Left) The SHP RNAi aphids show a lower reproduction rate and a shorter overall duration of reproduction than aphids feeding on control plant lines. (Right) The total reproduction of the SHP RNAi aphids is significantly lower than that of the control groups.

FIG. 12 shows the survival of aphids (given as dai—days after infestation) from the species *Sitobion avenae* feeding on control (wt—wild type; ev—empty vector) and shp-dsRNA expressing plants. Survival analysis was done by Kaplan Meier Log-Rank. Each group contained 15 aphids. Aphids feeding on shp-dsRNA expressing plants did not show reduced survival when compared with controls.

The following methods and examples are offered for illustrative purposes only, and are not intended to limit the scope of the present disclosure in any way.

METHODS AND EXAMPLES

In the following examples, materials and methods of the present disclosure are provided including the determination of the effect of SHP silencing on pest reproduction. It should be understood that these examples are for illustrative purpose only and are not to be construed as limiting this disclosure in any manner. All publications, patents, and patent applications cited herein are hereby incorporated by reference in their entirety for all purposes.

Example 1

Aphid and Plant Rearing

The *Acyrtosiphon pisum* clone LL01 was reared on 2-3-week-old bean plants (*Vicia faba* var. minor) in a climate cabinet (KBWF 720, Binder GmbH, Tuttlingen, Germany) with a 16-h photoperiod and a day/night temperature of 24/18° C. Plants for experiments and aphid rearing were cultivated in a greenhouse with an average temperature of 20° C. and natural light plus additional illumination (SONT Agro 400W, Phillips, Eindhoven, Netherlands) to maintain a 14-h photoperiod. The aphid species *Schizaphis graminum* and *Sitobion evenae* were reared on 2 week old *Hordeum vulgare* plants and *Myzus persicae* was reared on 2-3 week old *Vicia faba* plants. Environmental conditions were equal to those selected for *A. pisum*.

Example 2 dsRNA Production and Injection

A 491-bp template for the production of dsRNA representing the *A. pisum* SHP sequence (ACYPI009881) was generated by PCR from plasmid DNA using gene-specific primers containing a 5' T7 polymerase promoter sequence (AP-SHP-for 5'-TAA TAC GAC TCA CTA TAG GGA GAC GTT ATT ATT GCT GCT GCT GTG-3' and AP-SHP-back 5'-TAA TAC GAC TCA CTA TAG GGA GAA CAG CTA CCC TGG CCG ATC TT-3'). The sequence was ensured that it did not have overlaps exceeding 19 bp with any other gene, to avoid off-target effects. The template was purified using the QIAquick PCR Purification Kit (Qiagen, Hilden, Germany) and dsRNA was prepared using the Ambion MEGAscript RNAi kit (Applied Biosystems, Austin, Tex.). The primers were designed with Primer3 (Rozen S, Skaletsky 2000) and were purchased from Sigma-Aldrich (Taufkirchen, Germany). dsRNA was used representing the *Galleria mellonella* insect metalloproteinase inhibitor gene (AY330624) as a control (Wedde M, et al., 2007).

15 nl of dsRNA solution was injected under a stereomicroscope by using a Nanoliter 2000 injector together with a Sys-Micro4 controller (World Precision Instruments, Berlin, Germany). Glass microcapillaries for injection were pulled with a PN-30 puller (Narishige International Limited, London, UK). Prior to injection, aphids were immobilized with their dorsal thorax on a vacuum holder (van Helden M, Tjallingii W F, 2000). The dsRNA was injected at a rate of 5 nl/s between the mesothorax and methathorax, as previously described (Mutti N S, Park Y, Reese J C, Reeck G R, 2006). dsRNA with the same sequence was injected in all aphid species.

Example 3

Rearing Aphids During Experimental Treatments

Aphids (*A. pisum* and *M. persicae*) were reared on detached, mature *V. faba* leaves cut from intact plants with a razor blade. Petiole section of 1-5 mm in length was cut again under water and the leaf was transferred to a Petri dish, filled to a height of 7 mm with 1.5% tap water agar (Carl-Roth GmbH, Karlsruhe, Germany) containing 0.03% methyl-4-hydroxybenzoate (Sigma-Aldrich). Leafs were inserted into the cooled agar upside down and the Petri dishes were maintained in a climate cabinet as described above. Senescent leafs were replaced. *S. graminum* was reared on intact *H. vulgare* plants in leaf clip cages.

Example 4

Preparation of Aphid Salivary Sheaths and Observation by Scanning Electron Microscopy, Bright Filed Microscopy and Fluorescence Microscopy Aphids were reared on an artificial diet that mimics the cell-wall milieu (20 mM KCl, 1 mM CaCl2, 10 mM MES, adjusted to pH 5.5 (Will T, et al., 2012; Cosgrove D J, Cleland R E, 1983) to enforce secretion of gel saliva. The food was sterile-filtered before use (pore size 0.45 µm) and 150 µl was placed between two Parafilm sheets (sachet), previously sterilized with 30% H2O2 for at least 30 min. Five days after dsRNA injection 15 aphids of each treatment were placed in groups of five per sheet. The sachet was located on one side of a plastic ring. Opposite to the diet sachet, the ring was closed with a single Parafilm sheet after the ring volume was filled with water. The diet sachet was then placed downwards on a small aphid cage and aphids were allowed to feed for 24 h. Sheets containing aphids were then placed downwards in a Petri dish and were searched for salivary sheaths with an inverse microscope (Olympus IMT-2). Regions of interest were labeled, SEM sample holders were placed on these regions and Parafilm was cut around the sample holders with a scalpel. The samples were dried for a minimum of 3 days in a desiccator with silica gel under vacuum, then gold-sputtered and observed with a Zeiss DSM982 Gemini SEM. Two replicas were prepared for each treatment and 20 randomly-chosen salivary sheaths were observed for each replica.

As a result, the formation of the aphid salivary sheath was disrupted by SHP silencing. The Aphids (*A. pisum*) were injected with 25 ng of double-stranded RNA (dsRNA) corresponding to the major salivary sheath protein (SHP) and compared to non-treated controls and non-relevant dsRNA controls (injected with 25 ng of dsRNA corresponding to the insect metalloprotease inhibitor IMPI from the greater wax moth *Galleria mellonella* (Clermont A, et al., 2004) which is absent from aphids) when fed on artificial diets through Parafilm. After 5 days, salivary sheaths were prepared for scanning electron microscopy (SEM). This revealed that salivary sheaths secreted by the control aphids adopted the typical necklace-like structure that forms on this substrate (FIG. 1A-D, white arrows), whereas those secreted by the SHP RNAi aphids showed the remnants of a bead-like structure but were predominantly amorphous (FIGS. 1E and F). The injection of 50 ng of dsRNA almost completely abolished any bead-like structures, with minimal gel saliva deposits observed at the stylet penetration sites (FIGS. 1G and H, white arrows). The silencing of shp mRNA was confirmed by quantitative real time PCR (data not shown). Due to its stronger effect in *A. pisum* the injection amount of dsRNA was set to 50 ng for *M. persicae* and *S. graminum*.

Sample collection and preparation for *S. avenae* was done as described above without specific preparation for SEM. Instead of a SEM a bright field microscope (Leica DMLB, Leica Microsystems, Mannheim, Germany) was used to simplify the observation of salivary sheaths. Aphids feeding from wild type (FIG. 10A) and empty vector (FIG. 10B) controls for two weeks produce the typical sheath structure in artificial diet, while feeding for two weeks on shp-dsRNA plant line L26 disrupted sheath formation in artificial diet (FIG. 10C). Three replicates were prepared for each treatment and ten randomly chosen salivary sheaths were observed for each replica.

Example 5

EPG Analysis of Aphid Feeding Behavior

Aphids of the species *A. pisum* injected with 50 ng of dsRNA were selected for further structural and behavioral analysis. Aphid feeding behavior was monitored using the electrical penetration graph (EPG) technique (Tjallingii W F, 1988). A gold wire electrode (1 cm×20 µm) was attached to the dorsal abdomen of randomly selected apterous aphids 5 days after injection, using electrically conductive silver glue (Electrolube, Swadlincote, Derbyshire, UK) and a vacuum device for immobilization (van Helden M, Tjallingii W F, 2000). The aphid electrode was connected to a DC EPG Giga-8 (Tjallingii W F, 1988, Tjallingii W F, 1978) and the EPG output was recorded with Stylet+(hardware and software from EPG Systems, Wageningen, Netherlands). A second electrode (plant electrode) was inserted into the soil of potted plants. The experimental setup was placed in a Farraday cage to shield it from electromagnetic interference. Aphids were placed on the lower side of the petiole of a mature leaf on a 10-day-old plant, and EPG recordings were started immediately, running for 8 h. 14 biological replicates were carried out for each treatment. EPG waveforms were analyzed by pattern and autopower spectra (Prado E, Tjallingii W F, 1994) using the Stylet+ analysis module. Further analysis was performed with the workbook for automatic parameter calculation of EPG data version 4.4 (Sarria E, et al., 2009).

The possibility that SHP silencing could affect interactions with the epidermis, mesophyll and phloem was considered and we therefore analyzed 37 of the 132 calculated parameters listed in the workbook for automatic parameter calculation, electrical penetration graph (EPG) data version 4.4 (Table S1). As a result the SHP silencing increases aphid probing activity but delays and inhibits feeding.

TABLE S1

Behavioral analysis using 8-h EPG recordings in SHP RNAi aphids and controls.

| Tissue specificity | | Parameters | N | IMPI Mean [s] | SE [s] | N | SHP Mean [s] | SE [s] | P value |
|---|---|---|---|---|---|---|---|---|---|
| Plant acceptability | Epidermis | Time to 1st probe from start of EPG | 8 | 65.94 | 33.35 | 11 | 126.44 | 30.95 | 0.069** |
| | Epidermis and Mesophyll | Number of probes to the 1st E1 | 13 | 23.69 | 3.90 | 11 | 23.36 | 6.58 | 0.984* |
| | | Number of F | 14 | 1.36 | 0.27 | 14 | 0.71 | 0.19 | 0.064* |
| | | Total duration of F | 11 | 5082.76 | 939.58 | 8 | 2688.34 | 1073.73 | 0.113* |
| | | Mean duration of F | 11 | 3452.07 | 780.43 | 8 | 1772.87 | 537.15 | 0.137** |
| | | Average number of pd per probe | 14 | 14.5 | 6.15 | 13 | 10.39 | 1.85 | 0.544** |
| | | Time from start of EPG to 1st E | 14 | 11020.36 | 1853.27 | 14 | 13327.35 | 2756.92 | 0.783** |
| | | Time from 1st probe to 1st E | 14 | 10982.69 | 1854.87 | 14 | 13228.01 | 2765 | 0.854** |
| | Phloem | Number of E1 | 14 | 2.64 | 0.52 | 14 | 3.14 | 0.66 | 0.558* |
| | | Number of single E1 | 14 | 0.07 | 0.07 | 14 | 0.64 | 0.27 | 0.012* |
| | | Number of E2 | 14 | 2.5 | 0.48 | 14 | 2.29 | 0.55 | 0.64** |
| | | Number of sustained E2 (longer than 10 minutes) | 14 | 2.14 | 0.33 | 14 | 1.43 | 0.34 | 0.145* |
| | | Contribution of E1 to phloem phase (%) | 13 | 2.98 | 0.48 | 11 | 13.81 | 8.61 | 0.339** |
| | | Total duration of E | 13 | 9320.18 | 1167.81 | 11 | 5882.98 | 919.45 | 0.035* |
| | | Total duration of E1 | 13 | 249.02 | 43.04 | 11 | 426.13 | 173.98 | 0.885** |
| | | Total duration of E2 | 13 | 9071.16 | 1164.11 | 11 | 5456.85 | 990.77 | 0.03* |
| | | Mean duration of E1 | 13 | 108.68 | 26.39 | 11 | 88.1 | 29.53 | 0.06** |
| | | Mean duration of E2 | 13 | 4905.67 | 1221.21 | 11 | 2281.98 | 583.28 | 0.06** |
| | All tissues | Number of probes | 14 | 34.71 | 4.74 | 14 | 37.86 | 4.24 | 0.625* |
| | | Number of short probes (C < 3 minutes) | 14 | 25.64 | 4.08 | 14 | 22.79 | 3.23 | 0.587* |
| | | Total duration of C | 14 | 10585.98 | 962.67 | 14 | 14854.8 | 1516.52 | 0.025* |
| | | Total duration of no phloematic phase | 13 | 19169.54 | 1124.83 | 11 | 20606.39 | 1697.33 | 0.251** |
| | | Total duration of np | 14 | 5564.7 | 1137.94 | 14 | 8734.3 | 2014.78 | 0.408* |
| | | Total duration of pd | 14 | 10073.34 | 1563.08 | 13 | 7744.89 | 1966.94 | 0.193* |
| | | Total probing time | 14 | 24893.48 | 1952.43 | 14 | 24611.54 | 4025.88 | 0.646** |
| | | Mean duration of np | 14 | 152.68 | 15.38 | 14 | 1674.9 | 1440.95 | 0.818** |
| | | Time from start of EPG to 1st sustained E2 (10 minutes) | 14 | 11269.14 | 1896.99 | 14 | 16681.34 | 2873.88 | 0.408** |
| | | Time from 1st probe to 1st sustained E2 (10 minutes) | 14 | 11231.46 | 1898.74 | 14 | 16282.83 | 2815.42 | 0.491** |
| | | Time from start of EPG to 1st E2 | 14 | 11254.16 | 1899.55 | 14 | 13542.19 | 2866.63 | 0.748** |
| | | Time from 1st probe to 1st E2 | 14 | 11216.48 | 1901.29 | 14 | 14897.81 | 2821.31 | 0.818** |
| Phloem acceptability | Phloem | Duration of the longest E2 | 13 | 6264.13 | 1233.51 | 11 | 3550.96 | 888.01 | 0.068** |
| | | Duration of np just after the probe of the first sustained E2 | 10 | 88.68 | 29.75 | 8 | 258.03 | 65.38 | 0.022* |
| | | % E2 > 10 min | 13 | 92.86 | 4.85 | 11 | 66.84 | 10.75 | 0.032** |

In Table 1, data from selected parameters of Table S1 were sorted as events in classes representing 2 h intervals and analyzed using the non-parametric Wald-Wolfowitz-test.

TABLE 1

Non-parametric analysis of phloem localizing-parameters in SHP RNAi aphids and controls.

| Time | Start of EPG to 1st sustained E2 | | 1st probe to 1st sustained E2 | |
|---|---|---|---|---|
| | IMPI | SHP | IMPI | SHP |
| 0-2 h | 4 | 5 | 4 | 5 |
| 2-4 h | 8 | 1 | 8 | 1 |
| 4-6 h | 0 | 4 | 0 | 4 |
| 6-8 h | 2 | 1 | 2 | 1 |
| no detection | 0 | 3 | 0 | 3 |

TABLE 1-continued

Non-parametric analysis of phloem localizing-parameters in SHP RNAi aphids and controls.

| Time | Start of EPG to 1st sustained E2 | | 1st probe to 1st sustained E2 | |
|---|---|---|---|---|
| | IMPI | SHP | IMPI | SHP |
| Z (corr.) | 2.1184 | | 2.1184 | |
| P | 0.0208 | | 0.0341 | |

Results indicate clearly that sustained E2 (successful long-term access to a sieve tube (nutrition source) is significantly delayed as a consequence of shp silencing. In addition, interrupted sheath formation results in a higher percentage of non-phloem behavior over the complete observation time of 8 hours (FIG. 2).

The results in Table 2 indicate that SHP silenced aphids show a higher percentage of stylet movement in the plant (C) and a reduced ingestion (E2). The secretion of watery saliva after sieve tube penetration (E1) is not influenced. Data of grey filled cells (Table 2) are displayed in FIG. 3. The percentage of sustained ingestion events is reduced for SHP silenced aphids.

TABLE 2

Influence of the injection of dsRNA IMPI and dsRNA SHP on the percentage of non-phloematic and phloematic behavior of aphids. Statistical analysis was performed with ANOVA or ANOVA on ranks(*).

| Tissue specificity | Parameters | IMPI | | | SHP | | | |
|---|---|---|---|---|---|---|---|---|
| | | N | Mean [s] | SE [s] | N | Mean [s] | SE [s] | P value |
| Plant acceptability (Summary) | All tissues | % of probing spent in C | 14 | 45, 90 | 5, 91 | 14 | 70, 97 | 6, 74 | 0, 010 |
| | Phloem | % of probing spent in E1 | 14 | 0, 97 | 0, 21 | 14 | 1, 23 | 0, 55 | 0, 488* |
| | | % of probing spent in E2 | 14 | 33, 69 | 4, 91 | 14 | 16, 30 | 3, 82 | 0, 010 |
| | | & E2 >10 min | 13 | 92, 86 | 4, 85 | 11 | 66, 84 | 10, 75 | 0, 032* |

Example 6

Survival and Reproduction Assay

Survival assays (n=3) and reproduction assays (n=1) were conducted separately using 10-15 aphids per group in each test. Aphids of the species *A. pisum, M. persicae* and *S. graminum* were maintained on a single leaf in an agar plate or in a leaf clip cage as described above. Parameters were checked once every day from the first day after injection until the final aphid died. Plates and plants with clip cages respectively were placed in a climate cabinet using the conditions described above. Aphids of the species *S. avenae* that were used for testing shp-dsRNA expressing plant line L26 were kept in leaf clip cages and parameters were checked as described.

*A. pisum*: As a result it could be shown that SHP silencing inhibits aphid reproduction. The reproduction of aphids was monitored in SHP RNAi group and control groups for the lifespan of selected aphids. In all groups, the reproduction rate increased rapidly at the beginning of the observation period and reached a maximum after 4 days (FIG. 4). The maximum reproduction rate in the control groups was approximately eight nymphs per day, whereas in the SHP RNAi group it was six nymphs per day. Furthermore, reproduction in the control groups was maintained for 27 days (non-treated control) or 22 days (IMPI RNAi control) whereas the reproduction rate dropped off after 4 days in the SHP RNAi group and ceased after 17 days. There was a highly significant difference (p<0.001) in total mean reproduction (FIG. 4) between the SHP RNAi group (45.6 nymphs per adult) and untreated controls (88.2 nymphs per adult), and a slight significant difference (p=0.052) between the SHP RNAi group and IMPI RNAi group (68.9 nymphs per adult). There was no significant difference between the two control groups.

In view to survival, no differences were observed between the three different groups, non-treated, dsRNA IMPI injected and shp silenced (FIG. 5).

*M. persicae:*
Since injection of SHP dsRNA induced significant effects in *A. pisum* during the first days after injection, total observation time was reduced to 11 days for *M. persicae*. Control groups show a mean reproduction rate of approximately 4 nymphs per day during the observation period. SHP dsRNA injected aphids start at a comparable reproduction level that rapidly decreases to a reproduction rate of approximately 0.2 nymphs per day 6 days after treatment. Reproduction rate increases slightly during the remaining observation period. There was a significant difference (p<0.001) in total mean reproduction (FIG. 4) between the SHP RNAi group (~17 nymphs per adult) and untreated and IMPI controls (~45 nymphs per adult). There was no significant difference between the two control groups.

In view to survival, a significant difference was observed between the SHP RNAi group and the control groups (p<0.01; FIG. 5).

*S. graminum:*
Since injection of SHP dsRNA induced significant effects in *A. pisum* during the first days after injection, total observation time was reduced to 11 days for *S. graminum*. Although, a tendency is indicated for a reduced reproduction of aphids of the SHP RNAi group in comparison to the control groups no statistically significant difference was detected for total mean reproduction.

In view to survival, a difference between the SHP RNAi group and the control groups can be suggested but is not detected by statistical analysis (FIG. 5).

*S. avenae:*
In the control groups, the reproduction rate increased rapidly at the beginning of the observation period and reached a maximum after 3-4 days (FIG. 11). The maximum reproduction rate in the control groups was approximately 4-5 nymphs per day, whereas in the SHP RNAi group it was three nymphs per day. Furthermore, reproduction in the control groups was maintained for 42 days (non-treated control) or 44 days (empty vector). There was a highly significant difference (p<0.001) in total mean reproduction (FIG. 11) between the SHP RNAi group (28 nymphs per adult) and controls (58-63 nymphs per adult). There was no significant difference between the two control groups.

In view to survival, a difference between the SHP RNAi group and the control groups can be suggested but is not detected by statistical analysis (FIG. 12).

Example 7

Construction of shp Templates and Generation of Transgenic Barley Plants

For constitutive overexpression of shp-dsRNA in barley, a 491 nt cDNA template fragment (FIG. 7) from mRNA sequence encoding *A. pisum* SHP was amplified using specific primers and subsequently cloned into the binary RNAi vector p7i-Ubi-RNAi (DNA Cloning Service, Hamburg, Germany) by replacing its GUS template (FIG. 8). The plasmid p7i-Ubi-shp-RNAi, which contains shp fragment under control of inverted plant ubiquitin (Ubi) promoters, was transferred by electroporation into *Agrobacterium tumefaciens* strain AGL1 (Lazo et al., 1991) that was subsequently used for barley transformation. Transformation of immature barley embryos was done as described (Imani et al., 2011). PCR analysis was done to confirm integration of the transferred DNA and to select empty vector lines (ev) that contained p7i-Ubi-RNAi by using specific primers (Data not shown).

Example 8

Quantitative Real Time PCR

RNA was isolated from aphids 5 days after injection of dsRNA IMPI and dsRNA SHP respectively, 3×10 aphids for each treatment, as previously described by using TriReagent (Sigma-Aldrich) and was immediately stored at −80° C. mRNA was converted to cDNA (First Strand cDNA Synthesis Kit; Fermentas, St. Leon-Rot, Germany) after a cleanup (RNeasy MiniElute Cleanup Kit; Quiagen, Hilden, Germany) and subsequent qPCR was performed with the Applied Biosystems 7500 FAST real-time PCR system using SYBER green JumpStart Taq ReadyMix (Sigma-Aldrich, Germany). Appropriate primers were designed using Primer3 (Rozen S, Skaletsky H J, 2000) (AP-SHP-qPCR-for 5'-AAA TGT TGC GTT GTG GAC TT-3' and AP-SHP-qPCR-back 5'-GGT AAT CCT TGA AGG GGA GA-3') and were purchased from Sigma-Aldrich. The amplified sequence was different to the one used for dsRNA production. Ct values were determined with the 7500 Fast software. Transcript levels of shp-dsRNA were determined via the 2-ΔΔCt method by normalizing the amount of target transcript to the amount of 18s ribosomal RNA (GenBank ID: APU27819).

Analysis of shp expression in *S. avenae* by qRT-PCR indicates that shp is significantly silenced (p<0.001) due to feeding on shp-dsRNA expressing plant line L26 for two weeks (FIG. 9A). SHP expression analysis of aphids that were transferred on wild type plants after a feeding period of two weeks on shp-dsRNA expressing plant line L26 demonstrates that silencing of shp has a persistent character (FIG. 9B).

Example 9

Observing Effects of SHP Silencing on Offspring

The observation that SHP silencing reduces reproduction indicates that aphids of the SHP RNAi group take up less nutrition than control groups. This suggests consequences on the offspring. For this reason wing formation as well as maturation time was observed. Aphids that were used for nymph production were fed for two weeks on control plant lines and shp-dsRNA expressing plants respectively and were subsequently transferred to wt plants for 24 h for production of offspring. For each treatment 50 nymphs were observed until they reached maturity. Production of winged adults is significantly higher between shp-dsRNA expressing plant lines and controls (p<0.01; Table 3). An increased production of winged offspring in aphids is e.g. induced by a low nutrition supply to the mother to give the offspring the opportunity to reach new host plants. Furthermore, this would lead to a rapid decrease in aphid population on the original host plant. Regarding the fact that shp silencing is persistent for up to two weeks (FIG. 9B), colonization of new host plants will be deranged.

TABLE 3

Effect of shp silencing on the percentage of winged offspring.

| Plant line | Percentage of winged adults |
|---|---|
| GP (Wild type) | 3.5 ± .5/50 (7%) |

TABLE 3-continued

Effect of shp silencing on the percentage of winged offspring.

| Plant line | Percentage of winged adults |
|---|---|
| Empty vector | 5 ± m/50 (10%) |
| L26_SHP | 40 ± 0/50** (80%) |

Observing the effect of shp silencing on the maturation time of offspring was prepared as for wing formation. Maturation time is significantly longer on shp-dsRNA expressing plant lines (p<0.01; Table 4). An increased maturation time negatively affects total reproduction due to a delayed beginning of reproduction. In addition, an increased maturation time increases the risk for nymphs to become prey to predators, because this risk is higher for small nymphs than for adults.

TABLE 4

Effect of shp silencing on the maturation time of offspring.

| Plant line | Mean maturation time [days] |
|---|---|
| GP (Wild type) | 8.5 ± .5( |
| Empty vector | 8.5 ± .5 t |
| L26_SHP | 15.5 ± 5.5** |

Example 10

Statistical Analysis

Descriptive statistical analysis of aphid behavior was performed with Origin 8.1G (OriginLab Corporation, Northampton, Mass., USA) while comparison of treatments was performed with ANOVA and ANOVA on ranks using SigmaPlot 11 (Systat Software Inc., London, UK). The Wald-Wolfowitz test (SigmaPlot 11) was used to analyze non-parametric class-arranged behavior data. Because of the small sample size for non-parametric data analysis, Z and p values were corrected (Siegel S, 1956). Survival analysis was performed with Kaplan-Meier Survival Analysis Log-Rank (SigmaPlot 11), and ANOVA was used to compare the median and maximum survival rates. Reproduction data were analyzed by ANOVA. Data for qRT-PCR, the analysis of the percentage of winged aphids as well as data for determination of differences for maturation time were analyzed by Student's t-test. The level for significance for the statistical tests was set to p=0.05, whereas p-values between 0.05 and 0.075 indicated a trend with marginal significance.

REFERENCES

Brentassi M E, Rennes Lenicov A M M de (2007) Feeding behavior of the vector *Delphacodes kuscheli* (Hemiptera: Fulgoromorpha: Delphacidae) on maize and oat. Ann Soc Entomol Fr 43: 205-212.

Carolan J C, Fitzroy C I J, Ashton P D, Douglas A E, Wilkinson T L (2009) The secreted salivary proteome of the pea aphid *Acyrthosiphon pisum* characterised by mass spectrometry. Proteomics 9: 2457-2467.

Clermont A, Wedde M, Seitz V, Podsiadlowski L, Hummel M, Vilcinskas A (2004) Cloning and expression of an inhibitor against microbial metalloproteinases from insects (IMPI) contributing to innate immunity. Biochem J 382: 315-322.

Cosgrove D J, Cleland R E (1983) Solutes in the free space of growing stem tissues. Plant Physiol 72: 326-331.

Dedryver C-A, Ralec A L, Fabre F (2010) The conflicting relationships between aphids and men: A review of aphid damage and control strategies. Comptes Rendus Biologies 333: 539-553.

Freeman T P, Buckner J S, Nelson D R, Chu Chang C C, Henneberry T J (2001) Stylet penetration by *Bemisia argentifolii* (Homoptera: Aleyrodidae) into host leaf tissue. Ann Entomol Soc Am 94: 761-768.

Imani J, Li L, Schäfer P, Kogel K H (2011) STARTS—a stable root transformation system for rapid functional analyses of proteins of the monocot model plant barley. Plant J 67: 726-735.

Jauber-Possamai S, Le Trionnaire G, Bonhomme J, Christophides G K, Rispe C, Tagu D (2007) Gene knockdown by RNAi in the pea aphid *Acyrthosiphon pisum*. BMC Biotechnology 7: 63.

Lazo G R, Stein P A, Ludwig R A (1991) A DNA transformation-competent *Arabidopsis* genomic library in *Agrobacterium*. Biotechnology (N Y). 9: 963-967.

Mutti N S, Louis J, Pappan L K, Pappan K, Begum K et al. (2008) A protein from the salivary glands of the pea aphid, *Acyrthosiphon pisum*, is essential in feeding on a host plant. Proc Natl Acad Sci USA 105: 9965-9969.

Mutti N S, Park Y, Reese J C, Reek G R (2006) RNAi knockdown of a salivary transcript leading to lethality in the pea aphid, *Acyrtosiphon pisum*. J Insect Sci 6:38.

Pitino M, Coleman A D, Maffei M E, Ridout C J, Hogenhout S A (2011) Silencing of Aphid Genes by dsRNA Feeding from Plants. PLoS ONE 6: e25709. doi:10.1371/journal.pone.0025709

Prado E, Tjallingii W F (1994) Aphid activities during sieve element punctures. Ent Exp App 72: 157-165.

Rao S A K (2011) The identification and characterization of salivary proteins from the cereal aphids *Sitobion avenae*, *Metopolophium dirhodum* and *Rhopalosiphum padi*. Thesis, University College Dublin, Ireland.

Rozen S, Skaletsky H J (2000) Primer3 on the WWW for general users and for biologist programmers. In: Krawetz S, Misener S, editors. Bioinformatics Methods and Protocols: Methods in Molecular Biology. Totowa: Humana Press. pp. 365-386.

Sarria E, Cid M, Garzo E, Fereres A (2009) Workbook for automatic parameter calculation of EPG data. Comput Electron Agric 67: 35-42.

Shakesby A J, Wallace L S, Isaacs H V, Pritchard J, Roberts D M, Douglas A E (2009) A water-specific aquaporin involved in aphid osmoregulation. Insect Biochem Mol Biol 39: 1-10.

Siegel S (1956) Nonparametric statistics for the behavioral sciences. New York: McGraw-Hill.

Tatchell G M (1989) An estimate of the potential economic losses to some crops due to aphids in Britain. Crop Protection 8: 25-29.

Tjallingii W F (1978) Electronic recording of penetration behaviour by aphids. Ent Exp App 24: 721-730.

Tjallingii W F (1988) Electrical recording of stylet penetration activities. In: Minks A K, Harrewijn P, editors. Aphids: Their Biology, Natural Enemies and Control Vol 2B. Amsterdam: Elsevier. pp. 95-108.

Tjallingii W F, Hogen Esch T H (1993) Fine structure of aphid stylet routes in plant tissues in correlation with EPG signals. Physiol Entomol 18: 317-328.

Tjallingii W F, Hogen Esch Th (1993) Fine structure of aphid stylet routes in plant tissues in correlation with EPG signals. Physiol Ent 18: 317-328.

Truermit E, Sauer N (1995) The promoter of the *Arabidopsis thaliana* SUC2 sucrose-H+ symporter gene directs expression of β-glucuronidase to the phloem: Evidence for phloem loading and unloading by SUC2. Planta 196: 564-570.

van Helden M, Tjallingii W F (2000). Experimental design and analysis in EPG experiments with emphasis on plant resistance research. In Walker G P, Backus E A, editors. Principles and Applications of Electronic Monitoring and Other Techniques in the Study of Homopteran Feeding Behavior. Lanham: Thomas Say Publications in Entomology, Entomological Society of America. pp. 144-171.

Wedde M, Weise C, Nuck C, Altincicek B, Vilcinskas A (2007) The insect metalloproteinase inhibitor gene of the lepidopteran *Galleria mellonella* encodes two distinct inhibitors. Biol Chem 388: 119-127.

Wellings P W, Ward S A, Dixon A F G, Rabbinge R (1989) Crop loss assessment, in: A. K. Minks, P. Harrewijn (Eds.) Aphids, their biology, natural enemies and control, 2C, Elsevier, N L, pp. 49-69.

Whyard S, Singh A D, Wong S (2009) Ingested double-stranded RNAs can act as species-specific insecticides. Insect Biochem Mol Biol 39: 824-832.

Will T, Steckbauer K, Hardt M, van Bel A J E (2012) Aphid gel saliva: sheath structure, protein composition and secretory dependence on stylet-tip milieu. PLoS ONE 7(10): e46903. doi:10.1371/journal.pone.0046903.

Yang N-S, Christou P (1990) Cell type specific expression of a CaMV 35S-Gus gene in transgenic soybean plants. Development and Genetics 11: 289-293.

What is claimed is:

1. A pest control method comprising incorporating an inhibitor against a structural sheath protein (SHP) into a body of an agricultural target pest expressing the SHP, wherein the inhibitor is a compound selected from the group consisting of the following (a) or (b):
   (a) an RNAi inducing compound targeted at a nucleic acid coding SHP or parts thereof; or
   (b) a nucleic acid construct intracellularly producing an RNAi inducing compound targeted at a nucleic acid coding SHP or parts thereof;
   wherein the RNAi inducing compound is a compound selected from the group consisting of short interfering RNA (siRNA), microRNA (miRNA), short hairpin RNAs (shRNA), double stranded RNA (dsRNA) and a precursor thereof; and
   wherein the target pest belongs to *Acyrthosiphon pisum* and ingestion by the target pest of the inhibitor reduces reproduction of the target pest.

2. The pest control method according to claim 1, wherein the SHP is encoded by the nucleic acid sequence of SEQ ID NO:1, or a homolog thereof, wherein the homolog has a sequence identity of at least 90% to SEQ ID NO: 1 and encodes a functional SHP in the target pest.

3. The pest control method according to claim 1, wherein the inhibitor against SHP is incorporated into the pest by applying an agent containing the inhibitor to the plant prior to attack of the target pest.

4. The pest control method according to claim 1, comprising incorporating the inhibitor into the body of the target pest by ingesting a transgenic plant containing a gene encoding the inhibitor.

5. The method of claim 1, wherein the SHP is encoded by the nucleic acid sequence of SEQ ID NO:1.

6. The method of claim 1, wherein the reproduction is reduced by about 50%.

7. The method of claim 1, wherein ingestion by the target pest of the inhibitor results in eventual death of the target pest.

* * * * *

SEQUENCE LISTING

```
<160> NUMBER OF SEQ ID NOS: 8

<210> SEQ ID NO 1
<211> LENGTH: 4130
<212> TYPE: DNA
<213> ORGANISM: Acyrthosiphon pisum

<400> SEQUENCE: 1
gatataatga tttccatttt aagactatga tatttagttt taaacctgtt tttaggaatt      60
ggagagttag ataaaacaaa aatcggatta ttcaatactg agtagatcat taaataatag     120
aattcgtgaa aatagccagt ccatacaatg gatagtagcc taattattac tctttactgt     180
```

-continued

```
agtatctata ctctgttcaa aatgagatca ttactgcgcg gcgaccagtt ttcgtcgggc    240
ggcggtcaga cgccgtcccc actacggcga cgcgttgggc actgccacgg aacaaagcca    300
cgcccatgcg cacaactagg ccgccgaaat caactttcag ttcgtcttgt tgggaaccgg    360
tcaaaggcaa ctaacaggat gaggtctgta ctgattcttt gcgttattat tgctgctgct    420
gtggcatgcc cagtatcaaa acaaaagat tgctcttgcg gtctgcctaa aatatgtcct     480
tcaacgtgga aaattaagac atttgattcc caatgcgaaa cattagcatt ccaaggaaca    540
tggtttttac aaatggcaac accaacatac attgaccagc aaaacccatt aaaaaccggg    600
ctgttctgta acagttatcc ttgtaccaac aatcaactga tatttaagga taccacacca    660
tgtgatgata ccgattacaa cactgaatac gaagtgattg attcgtcata caatatctat    720
acccaatgta cagaaaccca aatagcatta ttatgcccag cgtatggcag ttccagcaaa    780
tatgcaatct ttaatgtcgg ttcagaaaaa tattatacaa acccaattgc cgaaaaatat    840
ccatttgttg acaaggattt attcagacat aagatcggcc agggtagctg tgagagagaa    900
tacacagtcg ctgtaatcgg tgctgatgac tgttggaaag agtatatggt gttagtcgtt    960
attaaccagt atgacaactt ctttggcgga gatgagtata ttacttgggt attgacaaga   1020
gatgttaacc ctgattggag tacttatgat aaagcataca atgatattaa gggaagtggt   1080
ctctgcccta actatttggt aagtgttgat cattcgtttg aatcaatgac aggaccttca   1140
atggcagtac cttcaatggc accaagtgtg gcagtacctt caatggcacc aactatgcct   1200
ggtgatgtcg atagtatggt acaaaaaacg tctgtctcta caacatcagc aacaaaatca   1260
attagtaccg actgtggtag tactgtaact tcatcatcca cttcaacaac tacgacatcg   1320
actgtgataa ttgataaaag ctcagatttc tctagtattt atgacatcgg accgtgtgat   1380
ttatacagtc catacgaggg tctccaaatc tacaaaaacc tggataaaga aacaattaga   1440
cgtgcctttt ctggaaaatta ttacatgacc caagctacac cttgttcgtt ttacgatacc   1500
cccaaatcaa aagtaggatt attaaatacg tgtttccctg catgcggtat gcaactctgt   1560
tttgatgatg catcaattga cgattgggat tgcaatactc ctcgtatggt tatggatcgt   1620
ggttacaata tgaggaccgg tgaagtgcat atgacgagaa gctatatttc ttcagcctat   1680
tctgacgacc atccatttgg tactgtcacg tatgcattcc attctgaggg atattatgat   1740
gtaccaattg atgaaacaga ttgcctacca ttagatggat tgatttgcaa accaccctca   1800
gatatataca agaaccaaat catagcaaat attattggat acaaagacaa tgattactta   1860
atgttttgca ttgcaaaccg atacaagaac ccgctctttc caaaaaagca agtacctcta   1920
gtctattgtt ataccagaga aagaatacca agtcaggata ctatgaatag tatcacacaa   1980
gaaatgttgc gttgtggact taacccaaat tacttgatga aaattgatca gtcgaaaaca   2040
attgaggaag tatttacgtt tgataaaact tattatgaat caacagtgac cagtacatct   2100
acgaccaaaa gtgtggtttc cacacgtgga ctcagcattg gaagctctcc ccttcaagga   2160
ttaccttcaa tatgtccacc agactggaac gttaaaactt ttgacaatca atacgctacc   2220
attgcattcc aaggaatatg gaatgtacaa atgactacac caacatatat aaatggaaac   2280
aacccattaa aaaccgggct attctgtaac agttatcctt gtaccaacaa tcaactgata   2340
tttaaggata ccacaccatg tgatgatacc gattacaaca ctgaatatga aatgactgat   2400
tcatcataca atctctatac ccagtgcaca gaaacccaaa aagcattatt atgcccagcg   2460 tatgcagtt gcagccaata tgcaatcttt aacgtcggtt cagaaaaata ttataatact   2520
gcgatcatcg aaaaatatcc atttattgac aaggatttat tcaggcataa gattgtccag   2580
```

```
ggtacctgtg agagagaata cacagtcgct gtaatcggtg ctgatgactg ttgggaagag    2640
tatatggtgt tagctgttat caaccagtat gataacgtat ttggcggaaa taagtatatt    2700
atttgggtag tgacgagaga tgctaaccct aaatggagta cttataagaa agcatacgaa    2760
gacattgaga gaagtggtct ctgccctaac tatttggtaa gtgttgatca ttcgttggaa    2820
tcaatgacag gaccttcaat ggcaccaagt gtggcagtac cttcaattgc accaactatg    2880
cctggtgatg ttgatagcat ggtacaaaaa acatctgtct ctacaacatc agcaacaaaa    2940
tcaattagta ccgactgcgg tagtactgta acttcgtcat ccacttcaac aactacgaca    3000
tcgactgtga taattgataa agctcagat ttctctagcc tgtatgagct cggacagtgt    3060
gatttataca aagatatcca atctacaaa aacctggata agaaacaat tagacgtgcc    3120 ttgtctggaa atattacat gacccaagct acaccttgtt cgtattacaa tagcccaaat    3180
tcgagagtcg gtattttaaa tacgtgtttc cctgcatgcg gtatgcaact ctgttttgat    3240
gatacgtcaa ttgatgattg ggattgcaat actcctcgta tggttatgga tcgtggttac    3300
gatatgagga ccggtgaagt gcaattgacg agaagttata tttcttcagt ctattctgac    3360
gaccatccat ttggtactgt cacgtatgca ttccattctg aaggatatta tgagggacca    3420
attgatgaaa tggattgtct accattagat ggaatgattt gcaaaccacc ctcagatata    3480
tacaagaacc aaatcatagc aagtattatt ggatacaaag acaatgatta cttaatattt    3540
tgcattgcaa acaaatacaa gaacccgctc tttagttcga caccagtaaa ccaagtcatt    3600
gcttatacaa gggagagagt tccaagcaag gaaactataa aatctatgac tcaagaatta    3660
ttgcaatgtg gttataatcc aaattatttg atcaaaatag atcagactat gtatatggat    3720
gatgattacg tatttgaaag ttcatattat gaatcacaaa cttcatgttg gagtagtagt    3780
agcagtagtt gtagtagcag cacgagtagt tcaactacta tttcatcttc gtcgagttcg    3840
tctgttagca tttcgtgtga ttaattcatt taaaacaata taatataata tgtcattaca    3900
gtcagtttaa taaataaata aaaatatcat gcattattat tttgtgttat atttttattg    3960
tctatccgtg gccagctttc tttaagtgaa taggttttac aatgacacaa aaatcattac    4020
gatatttaat actaaaagtg gttacttact tgtagataaa ttgatagaaa cttgaaacat    4080
taccctatta tgactctttc attgaacaat aaatgtattg gtttataacg                4130
```

<210> SEQ ID NO 2
<211> LENGTH: 491
<212> TYPE: DNA
<213> ORGANISM: ARTIFICIAL SEQUENCE
<220> FEATURE:
<223> OTHER INFORMATION: synthetic construct

<400> SEQUENCE: 2

```
gcgttattat tgctgctgct gtggcatgcc cagtatcaaa acaaaagat tgctcttgcg       60 gtctgcctaa aatatgtcct tcaacgtgga aaattaagac atttgattcc caatgcgaaa     120
cattagcatt ccaaggaaca tggtttttac aaatggcaac accaacatac attgaccagc     180
aaaacccatt aaaaaccggg ctgttctgta acagttatcc ttgtaccaac aatcaactga     240
tatttaagga taccacacca tgtgatgata ccgattacaa cactgaatac gaagtgattg     300
attcgtcata caatatctat acccaatgta cagaaaccca aatagcatta ttatgcccag     360
cgtatggcag ttccagcaaa tatgcaatct ttaatgtcgg ttcagaaaaa tattatacaa     420
acccaattgc cgaaaaatat ccatttgttg acaaggattt attcagacat aagatcggcc     480
```
agggtagctg t    491

<210> SEQ ID NO 3
<211> LENGTH: 1277
<212> TYPE: DNA
<213> ORGANISM: Artificial sequence
<220> FEATURE:
<223> OTHER INFORMATION: Plasmid-sequence after cloning (StarSEQ)-
      pGEM-T Vector

<400> SEQUENCE: 3

```
aaaagcatca cgcgttggga gctctcccat atggtcgacc tgcaggcggc cgcgaattca     60
ctagtgattt aatacgactc actataggga gaacagctac cctggccgat cttatgtctg    120
aataaatcct tgtcaacaaa tggatatttt tcggcaattg ggtttgtata atatttttct    180
gaaccgacat taaagattgc atatttgctg gaactgccat acgctgggca taacaatgct    240
atttgggttt ctgtacattg ggtatagata ttgtatgacg aatcaatcac ttcgtattca    300
gtgttgtaat cggtatcatc acatggtgtg gtatccttaa atatcagttg attgttggta    360
caaggataac tgttacagaa cagcccggtt tttaatgggt tttgctgatc aatgtatgtt    420
ggtgttgcca tttgtaaaaa ccatgttcct tggaatgcta atgtttcgca ttgggaatca    480
aatgtcttaa ttttccacgt tgaaggacat attttaggca gaccgcaaga gcaatctttt    540
gttttttgata ctgggcatgc cacagcagca gcaataataa cgtctcccta tagtgagtcg    600
tattaaatcg aattcccgcg gccgccatgg cggccgggag catgcgacgt cgggcccaat    660
tcgccctata gtgagtcgta ttacaattca ctggccgtcg ttttacaacg tcgtgactgg    720
gaaaaccctg gcgttaccca acttaatcgc cttgcagcac atccccctttt cgccagctgg    780
cgtaatagcg aagaggcccg caccgatcgc ccttcccaac agttgcgcag cctgaatggc    840
gaatggacgc gccctgtagc ggcgcattaa gcgcggcggg tgtggtggtt acgcgcagcg    900
tgaccgctac acttgccagc gccctagcgc ccgctccttt cgctttcttc ccttcctttc    960
tcgccacgtt cgccggcttt ccccgtcaag ctctaaatcg ggggctccct ttagggttcc   1020
gatttagtgc tttacggcac tcgaccccaa aaacttgatt agggtgatgg ttcacgtagt   1080
gggccatcgc ctgatgacgg ttttcgccct tgacgtggag tcacgttctt tatagtgact   1140
cttgttcaac tggacacact cacctattct cggtctattc tttgattata agaatttgcg   1200
attcgctatg gtaaaatgac tgattacaaa actacgcgat taacaaatat cgctacagtc   1260
tgaatgcggt atttcgc                                                  1277
```

<210> SEQ ID NO 4
<211> LENGTH: 1161
<212> TYPE: PRT
<213> ORGANISM: Acyrthosiphon pisum

<400> SEQUENCE: 4

```
Met Arg Ser Val Leu Ile Leu Cys Val Ile Ile Ala Ala Ala Val Ala
1               5                   10                  15

Cys Pro Val Ser Lys Thr Lys Asp Cys Ser Cys Gly Leu Pro Lys Ile
                20                  25                  30

Cys Pro Ser Thr Trp Lys Ile Lys Thr Phe Asp Ser Gln Cys Glu Thr
            35                  40                  45

Leu Ala Phe Gln Gly Thr Trp Phe Leu Gln Met Ala Thr Pro Thr Tyr
        50                  55                  60

Ile Asp Gln Gln Asn Pro Leu Lys Thr Gly Leu Phe Cys Asn Ser Tyr
65                  70                  75                  80
```

-continued

```
Pro Cys Thr Asn Asn Gln Leu Ile Phe Lys Asp Thr Pro Cys Asp
                85                  90                  95

Asp Thr Asp Tyr Asn Thr Glu Tyr Glu Val Ile Asp Ser Ser Tyr Asn
            100                 105                 110

Ile Tyr Thr Gln Cys Thr Glu Thr Gln Ile Ala Leu Leu Cys Pro Ala
        115                 120                 125

Tyr Gly Ser Ser Ser Lys Tyr Ala Ile Phe Asn Val Gly Ser Glu Lys
    130                 135                 140

Tyr Tyr Thr Asn Pro Ile Ala Glu Lys Tyr Pro Phe Val Asp Lys Asp
145                 150                 155                 160

Leu Phe Arg His Lys Ile Gly Gln Gly Ser Cys Glu Arg Glu Tyr Thr
                165                 170                 175

Val Ala Val Ile Gly Ala Asp Asp Cys Trp Lys Glu Tyr Met Val Leu
            180                 185                 190

Val Val Ile Asn Gln Tyr Asp Asn Phe Phe Gly Gly Asp Glu Tyr Ile
        195                 200                 205

Thr Trp Val Leu Thr Arg Asp Val Asn Pro Asp Trp Ser Thr Tyr Asp
    210                 215                 220

Lys Ala Tyr Asn Asp Ile Lys Gly Ser Gly Leu Cys Pro Asn Tyr Leu
225                 230                 235                 240

Val Ser Val Asp His Ser Phe Glu Ser Met Thr Gly Pro Ser Met Ala
                245                 250                 255

Val Pro Ser Met Ala Pro Ser Val Ala Val Pro Ser Met Ala Pro Thr
            260                 265                 270

Met Pro Gly Asp Val Asp Ser Met Val Gln Lys Thr Ser Val Ser Thr
        275                 280                 285

Thr Ser Ala Thr Lys Ser Ile Ser Thr Asp Cys Gly Ser Thr Val Thr
    290                 295                 300

Ser Ser Ser Thr Ser Thr Thr Thr Ser Thr Val Ile Ile Asp Lys
305                 310                 315                 320

Ser Ser Asp Phe Ser Ser Ile Tyr Asp Ile Gly Pro Cys Asp Leu Tyr
                325                 330                 335

Ser Pro Tyr Glu Gly Leu Gln Ile Tyr Lys Asn Leu Asp Lys Glu Thr
            340                 345                 350

Ile Arg Arg Ala Phe Ser Gly Asn Tyr Tyr Met Thr Gln Ala Thr Pro
        355                 360                 365

Cys Ser Phe Tyr Asp Thr Pro Lys Ser Lys Val Gly Leu Leu Asn Thr
    370                 375                 380

Cys Phe Pro Ala Cys Gly Met Gln Leu Cys Phe Asp Asp Ala Ser Ile
385                 390                 395                 400

Asp Asp Trp Asp Cys Asn Thr Pro Arg Met Val Met Asp Arg Gly Tyr
                405                 410                 415

Asn Met Arg Thr Gly Glu Val His Met Thr Arg Ser Tyr Ile Ser Ser
            420                 425                 430

Ala Tyr Ser Asp Asp His Pro Phe Gly Thr Val Thr Tyr Ala Phe His
        435                 440                 445

Ser Glu Gly Tyr Tyr Asp Val Pro Ile Asp Glu Thr Asp Cys Leu Pro
    450                 455                 460

Leu Asp Gly Leu Ile Cys Lys Pro Pro Ser Asp Ile Tyr Lys Asn Gln
465                 470                 475                 480

Ile Ile Ala Asn Ile Ile Gly Tyr Lys Asp Asn Asp Tyr Leu Met Phe
                485                 490                 495
```

-continued

```
Cys Ile Ala Asn Arg Tyr Lys Asn Pro Leu Phe Pro Lys Lys Gln Val
                500                 505                 510
Pro Leu Val Tyr Cys Tyr Thr Arg Glu Arg Ile Pro Ser Gln Asp Thr
            515                 520                 525
Met Asn Ser Ile Thr Gln Glu Met Leu Arg Cys Gly Leu Asn Pro Asn
        530                 535                 540
Tyr Leu Met Lys Ile Asp Gln Ser Lys Thr Ile Glu Glu Val Phe Thr
545                 550                 555                 560
Phe Asp Lys Thr Tyr Tyr Glu Ser Thr Val Thr Ser Thr Ser Thr Thr
                565                 570                 575
Lys Ser Val Val Ser Thr Arg Gly Leu Ser Ile Gly Ser Ser Pro Leu
            580                 585                 590
Gln Gly Leu Pro Ser Ile Cys Pro Pro Asp Trp Asn Val Lys Thr Phe
        595                 600                 605
Asp Asn Gln Tyr Ala Thr Ile Ala Phe Gln Gly Ile Trp Asn Val Gln
610                 615                 620
Met Thr Thr Pro Thr Tyr Ile Asn Gly Asn Asn Pro Leu Lys Thr Gly
625                 630                 635                 640
Leu Phe Cys Asn Ser Tyr Pro Cys Thr Asn Asn Gln Leu Ile Phe Lys
                645                 650                 655
Asp Thr Thr Pro Cys Asp Asp Thr Asp Tyr Asn Thr Glu Tyr Glu Met
            660                 665                 670
Thr Asp Ser Ser Tyr Asn Leu Tyr Thr Gln Cys Thr Glu Thr Gln Lys
        675                 680                 685
Ala Leu Leu Cys Pro Ala Tyr Gly Ser Cys Ser Gln Tyr Ala Ile Phe
690                 695                 700
Asn Val Gly Ser Glu Lys Tyr Tyr Asn Thr Ala Ile Ile Glu Lys Tyr
705                 710                 715                 720
Pro Phe Ile Asp Lys Asp Leu Phe Arg His Lys Ile Val Gln Gly Thr
                725                 730                 735
Cys Glu Arg Glu Tyr Thr Val Ala Val Ile Gly Ala Asp Asp Cys Trp
            740                 745                 750
Glu Glu Tyr Met Val Leu Ala Val Ile Asn Gln Tyr Asp Asn Val Phe
        755                 760                 765
Gly Gly Asn Lys Tyr Ile Ile Trp Val Val Thr Arg Asp Ala Asn Pro
770                 775                 780
Lys Trp Ser Thr Tyr Lys Lys Ala Tyr Glu Asp Ile Glu Arg Ser Gly
785                 790                 795                 800
Leu Cys Pro Asn Tyr Leu Val Ser Val Asp His Ser Leu Glu Ser Met
                805                 810                 815
Thr Gly Pro Ser Met Ala Pro Ser Val Ala Val Pro Ser Ile Ala Pro
            820                 825                 830
Thr Met Pro Gly Asp Val Asp Ser Met Val Gln Lys Thr Ser Val Ser
        835                 840                 845
Thr Thr Ser Ala Thr Lys Ser Ile Ser Thr Asp Cys Gly Ser Thr Val
850                 855                 860
Thr Ser Ser Ser Thr Ser Thr Thr Thr Ser Thr Val Ile Ile Asp
865                 870                 875                 880
Lys Ser Ser Asp Phe Ser Ser Leu Tyr Glu Leu Gly Gln Cys Asp Leu
                885                 890                 895
Tyr Lys Asp Ile Gln Ile Tyr Lys Asn Leu Asp Lys Glu Thr Ile Arg
            900                 905                 910
Arg Ala Leu Ser Gly Lys Tyr Tyr Met Thr Gln Ala Thr Pro Cys Ser
```

|     | 915 |     |     | 920 |     |     | 925 |     |     |     |     |
|-----|-----|-----|-----|-----|-----|-----|-----|-----|-----|-----|-----|

Tyr Tyr Asn Ser Pro Asn Ser Arg Val Gly Ile Leu Asn Thr Cys Phe
    930                 935                 940

Pro Ala Cys Gly Met Gln Leu Cys Phe Asp Asp Thr Ser Ile Asp Asp
945               950               955              960

Trp Asp Cys Asn Thr Pro Arg Met Val Met Asp Arg Gly Tyr Asp Met
               965               970              975

Arg Thr Gly Glu Val Gln Leu Thr Arg Ser Tyr Ile Ser Ser Val Tyr
        980               985              990

Ser Asp Asp His Pro Phe Gly Thr Val Thr Tyr Ala Phe His Ser Glu
            995            1000          1005

Gly Tyr Tyr Glu Gly Pro Ile Asp Glu Met Asp Cys Leu Pro Leu
    1010              1015              1020

Asp Gly Met Ile Cys Lys Pro Pro Ser Asp Ile Tyr Lys Asn Gln
1025               1030              1035

Ile Ile Ala Ser Ile Ile Gly Tyr Lys Asp Asn Asp Tyr Leu Ile
    1040              1045              1050

Phe Cys Ile Ala Asn Lys Tyr Lys Asn Pro Leu Phe Ser Ser Thr
1055               1060              1065

Pro Val Asn Gln Val Ile Ala Tyr Thr Arg Glu Arg Val Pro Ser
    1070              1075              1080

Lys Glu Thr Ile Lys Ser Met Thr Gln Glu Leu Leu Gln Cys Gly
1085               1090              1095

Tyr Asn Pro Asn Tyr Leu Ile Lys Ile Asp Gln Thr Met Tyr Met
    1100              1105              1110

Asp Asp Asp Tyr Val Phe Glu Ser Ser Tyr Tyr Glu Ser Gln Thr
1115               1120              1125

Ser Cys Trp Ser Ser Ser Ser Ser Cys Ser Ser Ser Thr Ser
    1130              1135              1140

Ser Ser Thr Thr Ile Ser Ser Ser Ser Ser Ser Val Ser Ile
    1145              1150              1155

Ser Cys Asp
    1160

```
<210> SEQ ID NO 5
<211> LENGTH: 2415
<212> TYPE: DNA
<213> ORGANISM: Sitobion avenae

<400> SEQUENCE: 5
ggtggttatt attggctggc tgctgtggc atgcccatta tcatcaaaat taaagggtt      60 gttcttgcaa atttgcctaa atatgtcct ccatcgtgga aaattaagac atttgattcc     120
caatacgcaa cattagcatt ccaaggaaaa tggtatctac aattgacaac accaacatac    180
attgaccagc aaagcccatt aaaaaccggg ctgttctgta acagttatcc ttctaccaaa    240
aatgaactgt tatttaagga taccacaccg tgtgatgata ccgattacaa cactgaatac    300
gaagtgattg attcatcata taatatttat tcccaatgta cagaaaccca taaagcatta    360
ctatccccag cgtatggcaa ggatagccca tgcaatctt taacctcgg ttcagaaaaa      420 tattatacaa tcccaattat cgaaaaaaat ccatttgttg acctggattt aatcaggcat    480
aagatagtca agggtaccta tgagagaaa tacacagtcg ctgtaatcgg tgctgatgac    540
tgttggaaag agtatatggt gttagctgtt atcaacaagt atgacaactt ctttggtgga    600
aatgaccata ttatttgggt agtgacgaga gatgttaacc gtaattggtc tacttatgat    660
```

-continued

```
aaagcataca acgatattaa ggaaagtggt ctctgcccta acattttggt aagtgttgat    720
cattcgtttg aacccatgac aggaccttca atagcagtac cttcaatgga accaagtgtg    780
gcagtacctt caatggcacc aactatgcct ggtgatatcg atggcatggt acaaacaacg    840
tctgtctcta acatcagc aacgaaatca ataagtaccg acggcgatac tgctgtaact     900
tcatcatcca cttcaacaac tacgacatcg actgtgataa ttgataaaag tgatgatttc    960
tcttgcctgt ttgacatcga cgcgtttgat ttattcaaac catacgacgg tctcaaaatc   1020
tataaaaata tggataaacc aacaatcaga cgtgccttgt ctggaaatta tttcatgacc   1080
caagctacac cttgttcgtt ttacgatacc cccaaatcaa agtaggatt attgaatacg    1140 tgtttccctg gatgtggaat gcaactcagt tttgatgata catcaattga tgattgggat   1200
tgcgttactc ctcgtatggt tatggatcgt ggttacaata tgagaaccgg tgaagtgcaa   1260
atgacgagaa gttatattac tccagtctat cctgaagacc atccatttgg tactaccaca   1320
tatgcattat attctgaagg atattatgat acaccaattg atgaaatgga tatcctaaca   1380
ttagatggaa tgatttgcaa agcacccta gatatataca agaaccaaat catagcaagt   1440
attatcggtt acaaagacaa tgattactta atgattagca ttgctaaccg atacaagaac   1500
ccgctctttc caaaaaagca agtacctcta gtctattgtt ataccagaga cagaattcca   1560
agtcagacta ctttgaatag tatcacacaa gaaatgttgc gttgtggact taacccaaat   1620
tacttgatga aaattgatca gtcaaaaaca attgaagaca aatttacgtt tgataaagcg   1680
ttttatgaat taccagtgat cagtacatct acgactaaaa gtatagtttc cacacgtgga   1740
atcagtattg taaagtctcc ccttaaagga ttaccttcaa tttgtccaaa agactgggat   1800
gttaaaactt ttgacagtca atacgctacc cttgcattcc aaggaacatg gaatgtacag   1860
atgactacac caacatatat aaatggaaac aaccccattaa aaaccgggct attctgtaac   1920
agttatccat gcaccagaaa tcaattgata ttcaaggata ccacccgtg tgatgatacc    1980 gattacaaca ctgaatacga aatgattgat tcatcataca atctctatac ccagtgcaca   2040
gaaacccaaa aagcattatt acgcccagcg tatggcagtt ccagcccata tgcaatcttt   2100
aacgtcggtt cacaaaaata ttataatatc ccgattattg aaaaacatcc atttgttgac   2160
aaggatttat tcaggcataa gatagtcaag ggtacctgtg agagagaata cacaatcgct   2220
gtaatcggtg ctgatgactg ttggaaagag tatatggtgt tagctgttat caacgagtat   2280
gacaacttct tttgcggaaa taatcatatt atttggttg tgacgagaga tgctaaccct   2340
aaatggagta cttataagaa agcatacgaa gacattgaga gaagtggtct ctgctctaac   2400
tattgataaa gtgtg                                                     2415
```

<210> SEQ ID NO 6
<211> LENGTH: 801
<212> TYPE: PRT
<213> ORGANISM: Sitobion avenae

<400> SEQUENCE: 6

Gly Gly Tyr Tyr Trp Leu Ala Gly Cys Gly Met Pro Ile Ile Ile Lys
1               5                   10                  15

Ile Lys Arg Val Val Leu Ala Asn Leu Pro Lys Ile Cys Pro Pro Ser
            20                  25                  30

Trp Lys Ile Lys Thr Phe Asp Ser Gln Tyr Ala Thr Leu Ala Phe Gln
        35                  40                  45

Gly Lys Trp Tyr Leu Gln Leu Thr Thr Pro Thr Tyr Ile Asp Gln Gln

```
                50                  55                  60
Ser Pro Leu Lys Thr Gly Leu Phe Cys Asn Ser Tyr Pro Ser Thr Lys
 65                  70                  75                  80

Asn Glu Leu Leu Phe Lys Asp Thr Thr Pro Cys Asp Asp Thr Asp Tyr
                     85                  90                  95

Asn Thr Glu Tyr Glu Val Ile Asp Ser Ser Tyr Asn Ile Tyr Ser Gln
                    100                 105                 110

Cys Thr Glu Thr His Lys Ala Leu Leu Ser Pro Ala Tyr Gly Lys Asp
                    115                 120                 125

Ser Pro Tyr Ala Ile Phe Asn Leu Gly Ser Glu Lys Tyr Tyr Thr Ile
130                                 135                 140

Pro Ile Ile Glu Lys Asn Pro Phe Val Asp Leu Asp Leu Ile Arg His
145                 150                 155                 160

Lys Ile Val Lys Gly Thr Tyr Glu Arg Glu Tyr Thr Val Ala Val Ile
                    165                 170                 175

Gly Ala Asp Asp Cys Trp Lys Glu Tyr Met Val Leu Ala Val Ile Asn
                    180                 185                 190

Lys Tyr Asp Asn Phe Phe Gly Gly Asn Asp His Ile Ile Trp Val Val
                    195                 200                 205

Thr Arg Asp Val Asn Arg Asn Trp Ser Thr Tyr Asp Lys Ala Tyr Asn
210                                 215                 220

Asp Ile Lys Glu Ser Gly Leu Cys Pro Asn Ile Leu Val Ser Val Asp
225                 230                 235                 240

His Ser Phe Glu Pro Met Thr Gly Pro Ser Ile Ala Val Pro Ser Met
                    245                 250                 255

Glu Pro Ser Val Ala Val Pro Ser Met Ala Pro Thr Met Pro Gly Asp
                    260                 265                 270

Ile Asp Gly Met Val Gln Thr Thr Ser Val Ser Thr Thr Ser Ala Thr
                    275                 280                 285

Lys Ser Ile Ser Thr Asp Gly Asp Thr Ala Val Thr Ser Ser Ser Thr
                    290                 295                 300

Ser Thr Thr Thr Thr Ser Thr Val Ile Ile Asp Lys Ser Asp Asp Phe
305                                 310                 315                 320

Ser Cys Leu Phe Asp Ile Asp Ala Phe Asp Leu Phe Lys Pro Tyr Asp
                    325                 330                 335

Gly Leu Lys Ile Tyr Lys Asn Met Asp Lys Pro Thr Ile Arg Arg Ala
                    340                 345                 350

Leu Ser Gly Asn Tyr Phe Met Thr Gln Ala Thr Pro Cys Ser Phe Tyr
                    355                 360                 365

Asp Thr Pro Lys Ser Lys Val Gly Leu Leu Asn Thr Cys Phe Pro Gly
                    370                 375                 380

Cys Gly Met Gln Leu Ser Phe Asp Asp Thr Ser Ile Asp Asp Trp Asp
385                                 390                 395                 400

Cys Val Thr Pro Arg Met Val Met Asp Arg Gly Tyr Asn Met Arg Thr
                    405                 410                 415

Gly Glu Val Gln Met Thr Arg Ser Tyr Ile Thr Pro Val Tyr Pro Glu
                    420                 425                 430

Asp His Pro Phe Gly Thr Thr Tyr Ala Leu Tyr Ser Glu Gly Tyr
                    435                 440                 445

Tyr Asp Thr Pro Ile Asp Glu Met Asp Ile Leu Thr Leu Asp Gly Met
                    450                 455                 460

Ile Cys Lys Ala Pro Ser Asp Ile Tyr Lys Asn Gln Ile Ile Ala Ser
465                                 470                 475                 480
```

```
Ile Ile Gly Tyr Lys Asp Asn Asp Tyr Leu Met Ile Ser Ile Ala Asn
            485                 490                 495
Arg Tyr Lys Asn Pro Leu Phe Pro Lys Lys Gln Val Pro Leu Val Tyr
            500                 505                 510
Cys Tyr Thr Arg Asp Arg Ile Pro Ser Gln Thr Thr Leu Asn Ser Ile
            515                 520                 525
Thr Gln Glu Met Leu Arg Cys Gly Leu Asn Pro Asn Tyr Leu Met Lys
            530                 535                 540
Ile Asp Gln Ser Lys Thr Ile Glu Asp Lys Phe Thr Phe Asp Lys Ala
545                 550                 555                 560
Phe Tyr Glu Leu Pro Val Ile Ser Thr Thr Lys Ser Ile Val
            565                 570                 575
Ser Thr Arg Gly Ile Ser Ile Val Lys Ser Pro Leu Lys Gly Leu Pro
            580                 585                 590
Ser Ile Cys Pro Lys Asp Trp Asp Val Lys Thr Phe Asp Ser Gln Tyr
            595                 600                 605
Ala Thr Leu Ala Phe Gln Gly Thr Trp Asn Val Gln Met Thr Thr Pro
            610                 615                 620
Thr Tyr Ile Asn Gly Asn Asn Pro Leu Lys Thr Gly Leu Phe Cys Asn
625                 630                 635                 640
Ser Tyr Pro Cys Thr Arg Asn Gln Leu Ile Phe Lys Asp Thr Thr Pro
            645                 650                 655
Cys Asp Asp Thr Asp Tyr Asn Thr Glu Tyr Glu Met Ile Asp Ser Ser
            660                 665                 670
Tyr Asn Leu Tyr Thr Gln Cys Thr Glu Thr Gln Lys Ala Leu Leu Arg
            675                 680                 685
Pro Ala Tyr Gly Ser Ser Pro Tyr Ala Ile Phe Asn Val Gly Ser
            690                 695                 700
Gln Lys Tyr Tyr Asn Ile Pro Ile Ile Glu Lys His Pro Phe Val Asp
705                 710                 715                 720
Lys Asp Leu Phe Arg His Lys Ile Val Lys Gly Thr Cys Glu Arg Glu
            725                 730                 735
Tyr Thr Ile Ala Val Ile Gly Ala Asp Asp Cys Trp Lys Glu Tyr Met
            740                 745                 750
Val Leu Ala Val Ile Asn Glu Tyr Asp Asn Phe Phe Cys Gly Asn Asn
            755                 760                 765
His Ile Ile Trp Val Val Thr Arg Asp Ala Asn Pro Lys Trp Ser Thr
            770                 775                 780
Tyr Lys Lys Ala Tyr Glu Asp Ile Glu Arg Ser Gly Leu Cys Ser Asn
785                 790                 795                 800
Tyr

<210> SEQ ID NO 7
<211> LENGTH: 2426
<212> TYPE: DNA
<213> ORGANISM: Metopolophium dirhodum

<400> SEQUENCE: 7
gtcctgttgt actgattctt tgcgttatta ttgctgctgc tgtggcatgc ccattatcaa      60
aaaaaaaaga ttgttcttgc aatttgccta aaatatgtcc ttcaacgtgg aaaattaaga     120
catttgattc ccaatacgca acattagcat tccaaggaac atggtttcta caattgacaa     180
caccaacata cattgaccag caaaacccat taaaaccgg gctgttctgt aacagttatc      240
```

```
cttgtaccaa aaatgaactg atatttaagg ataccacacc gtgtgatgat accgattaca      300
acactgaata cgaagtgatt gattcatcat acaatattta ttcccaatct acagaaaccc      360
aaaaagcatt attatgccca gcgtatggca gttgtagccc atatgcaatc tttaacgtcg      420
gttcagaaaa atattataca aacccaatta tcgaaaaaaa tccatttatt gaccaggatt      480
tattcagaca taagatcggc aagggtagct gtgagagaga atacacagtc gctgtaatcg      540
gtgctgatga ctgttggaaa gagtatatgg tgttagctgt tatcaacgag tatgacaact      600
tctttggcgg aaataagtat attatttggg tagtgacgag agatgttaac cctgattggt      660
ctacttatga taaagcatac aatgatatta aggcaagtgg tctctcgccc aactatttgg      720
taagtgttga tcattcgttt gaaccaatgc caggaccttc aatgccagta ccttcaatgg      780
caccaagtat gccagtacct tcaatggcac caactttgcc tggtgatatc gatggcatgg      840
tacaaaaaac gtctgtctct acaacatcag caacaaaatc aatttgtacc gacagcggta      900
ctactgtaac ttcatcatcc acttcaacga ctacaacatc gactgtgata attgataaaa      960
gctcagattt ctctagcctg tatgacgtcg agccgtgtga tttatacaaa ccatacgacg     1020
gtttcaaaat ctataaaaac ctggataaac caacaattaa aaaagccttg tctggaaaat     1080
atttcatgac ccaagctaca ccttgttcgt tttacgatac ccccaaatca aaagtaggat     1140
tattgaatac gtgtttccct ggatgtggaa tgcaactcta ttttgatgat acaccaattg     1200
atgattggga ttgcaatact cctcgtatgg ttatggatcg tggttacaat atgaggaccg     1260
gtgaagtgca tatgacgaga agctatattt cttcagtcta tcctgacgac catccatttg     1320
gtactaccac gtatgcattc cattctgaag gatattatga tgtaccaatt gaagaaacgg     1380
attccctacc attagatgga attatttgca agcaccctc agatatatac aagaaccaaa     1440
tcatagcaag tattattgga tacaaagaca atgattactt aattcttagc attgcgaacc     1500
gatacaagaa cccgctcttt ccaaaaaagc aagtaccttt agtctattgt tataccagag     1560
aaagaattcc aagtcagact actatgaata atatcacaca agaaatgttg cgttgtggac     1620
ttaacccaaa ttacttaatg aaaattgatc agtcaaaaac aattgagaaa gaatttacgt     1680
ttgataaagc gtattatgaa ttatcagtga ccagtacaac tatgactaaa agtacggttt     1740
ccacacgtgg aatcagcatt ggaaagtctc cccttcaagg attaccttca atttgtccac     1800
aagactggga tgttaaaact tttgacagtc aatacgctac ccttgcattc caaggaacat     1860
ggaatgtaca aatgactaca ccaacatata taaatggaaa caacccatta aaaaccgggc     1920
tattctgtaa cagttatcca tgcaccggaa atcaattgat attcaaggat accacaccac     1980
aagataatac cgattacaac actgaatacg aaatgactga ttcatcatac aatctctata     2040
cccagtgcac agaaacccaa aaagcattat tacgcccagc gtatggcagt tccagcccat     2100
atgcaatctt taacgtcggt tcacaaaaat attataatat cccgattatt gaaaaacatc     2160
catttgttga caaggatta ttcaggcata agatagtcaa gggtacctgt gagagagaat     2220
acacaatcgc tgtaatcggt gctgatgact gttggaaaga gtatatggtg ttagctgtta     2280
tcaacgagta tgacaacttc ttttgcggaa ataatcatat tatttgggt gtgacgagag     2340
atgctaaccc taaatggagt acttataaga aagcatacga agacattgag agaagtggtc     2400
tctgctctaa ctattgataa agtgtg                                           2426
```

<210> SEQ ID NO 8
<211> LENGTH: 804
<212> TYPE: PRT
<213> ORGANISM: Metopolophium dirhodum

<400> SEQUENCE: 8

```
Pro Val Val Leu Ile Leu Cys Val Ile Ala Ala Val Ala Cys
1               5                   10                  15

Pro Leu Ser Lys Lys Asp Cys Ser Cys Asn Leu Pro Lys Ile Cys
            20                  25                  30

Pro Ser Thr Trp Lys Ile Lys Thr Phe Asp Ser Gln Tyr Ala Thr Leu
                35                  40                  45

Ala Phe Gln Gly Thr Trp Phe Leu Gln Leu Thr Thr Pro Thr Tyr Ile
    50                  55                      60

Asp Gln Gln Asn Pro Leu Lys Thr Gly Leu Phe Cys Asn Ser Tyr Pro
65                  70                  75                  80

Cys Thr Lys Asn Glu Leu Ile Phe Lys Asp Thr Thr Pro Cys Asp Asp
                85                  90                  95

Thr Asp Tyr Asn Thr Glu Tyr Glu Val Ile Asp Ser Ser Tyr Asn Ile
                100                 105                 110

Tyr Ser Gln Ser Thr Glu Thr Gln Lys Ala Leu Leu Cys Pro Ala Tyr
                115                 120                 125

Gly Ser Cys Ser Pro Tyr Ala Ile Phe Asn Val Gly Ser Glu Lys Tyr
130                 135                 140

Tyr Thr Asn Pro Ile Ile Glu Lys Asn Pro Phe Ile Asp Gln Asp Leu
145                 150                 155                 160

Phe Arg His Lys Ile Gly Lys Gly Ser Cys Glu Arg Glu Tyr Thr Val
                165                 170                 175

Ala Val Ile Gly Ala Asp Asp Cys Trp Lys Glu Tyr Met Val Leu Ala
                180                 185                 190

Val Ile Asn Glu Tyr Asp Asn Phe Phe Gly Gly Asn Lys Tyr Ile Ile
                195                 200                 205

Trp Val Val Thr Arg Asp Val Asn Pro Asp Trp Ser Thr Tyr Asp Lys
                210                 215                 220

Ala Tyr Asn Asp Ile Lys Ala Ser Gly Leu Ser Pro Asn Tyr Leu Val
225                 230                 235                 240

Ser Val Asp His Ser Phe Glu Pro Met Pro Gly Pro Ser Met Pro Val
                245                 250                 255

Pro Ser Met Ala Pro Ser Met Pro Val Pro Ser Met Ala Pro Thr Leu
                260                 265                 270

Pro Gly Asp Ile Asp Gly Met Val Gln Lys Thr Ser Val Ser Thr Thr
                275                 280                 285

Ser Ala Thr Lys Ser Ile Cys Thr Asp Ser Gly Thr Thr Val Thr Ser
            290                 295                 300

Ser Ser Thr Ser Thr Thr Thr Thr Ser Thr Val Ile Ile Asp Lys Ser
305                 310                 315                 320

Ser Asp Phe Ser Ser Leu Tyr Asp Val Glu Pro Cys Asp Leu Tyr Lys
                325                 330                 335

Pro Tyr Asp Gly Phe Lys Ile Tyr Lys Asn Leu Asp Lys Pro Thr Ile
                340                 345                 350

Lys Lys Ala Leu Ser Gly Lys Tyr Phe Met Thr Gln Ala Thr Pro Cys
                355                 360                 365

Ser Phe Tyr Asp Thr Pro Lys Ser Lys Val Gly Leu Leu Asn Thr Cys
                370                 375                 380

Phe Pro Gly Cys Gly Met Gln Leu Tyr Phe Asp Asp Thr Pro Ile Asp
385                 390                 395                 400

Asp Trp Asp Cys Asn Thr Pro Arg Met Val Met Asp Arg Gly Tyr Asn
```

```
                    405                 410                 415
Met Arg Thr Gly Glu Val His Met Thr Arg Ser Tyr Ile Ser Ser Val
                420                 425                 430

Tyr Pro Asp Asp His Pro Phe Gly Thr Thr Thr Tyr Ala Phe His Ser
            435                 440                 445

Glu Gly Tyr Tyr Asp Val Pro Ile Glu Glu Thr Asp Ser Leu Pro Leu
        450                 455                 460

Asp Gly Ile Ile Cys Lys Ala Pro Ser Asp Ile Tyr Lys Asn Gln Ile
465                 470                 475                 480

Ile Ala Ser Ile Ile Gly Tyr Lys Asp Asn Asp Tyr Leu Ile Leu Ser
                485                 490                 495

Ile Ala Asn Arg Tyr Lys Asn Pro Leu Phe Pro Lys Lys Gln Val Pro
                500                 505                 510

Leu Val Tyr Cys Tyr Thr Arg Glu Arg Ile Pro Ser Gln Thr Thr Met
                515                 520                 525

Asn Asn Ile Thr Gln Glu Met Leu Arg Cys Gly Leu Asn Pro Asn Tyr
            530                 535                 540

Leu Met Lys Ile Asp Gln Ser Lys Thr Ile Glu Lys Glu Phe Thr Phe
545                 550                 555                 560

Asp Lys Ala Tyr Tyr Glu Leu Ser Val Thr Ser Thr Thr Met Thr Lys
                565                 570                 575

Ser Thr Val Ser Thr Arg Gly Ile Ser Ile Gly Lys Ser Pro Leu Gln
                580                 585                 590

Gly Leu Pro Ser Ile Cys Pro Gln Asp Trp Asp Val Lys Thr Phe Asp
            595                 600                 605

Ser Gln Tyr Ala Thr Leu Ala Phe Gln Gly Thr Trp Asn Val Gln Met
        610                 615                 620

Thr Thr Pro Thr Tyr Ile Asn Gly Asn Asn Pro Leu Lys Thr Gly Leu
625                 630                 635                 640

Phe Cys Asn Ser Tyr Pro Cys Thr Gly Asn Gln Leu Ile Phe Lys Asp
                645                 650                 655

Thr Thr Pro Gln Asp Asn Thr Asp Tyr Asn Thr Glu Tyr Glu Met Thr
            660                 665                 670

Asp Ser Ser Tyr Asn Leu Tyr Thr Gln Cys Thr Glu Thr Gln Lys Ala
        675                 680                 685

Leu Leu Arg Pro Ala Tyr Gly Ser Ser Pro Tyr Ala Ile Phe Asn
        690                 695                 700

Val Gly Ser Gln Lys Tyr Tyr Asn Ile Pro Ile Glu Lys His Pro
705                 710                 715                 720

Phe Val Asp Lys Asp Leu Phe Arg His Lys Ile Val Lys Gly Thr Cys
                725                 730                 735

Glu Arg Glu Tyr Thr Ile Ala Val Ile Gly Ala Asp Cys Trp Lys
            740                 745                 750

Glu Tyr Met Val Leu Ala Val Ile Asn Glu Tyr Asp Asn Phe Phe Cys
        755                 760                 765

Gly Asn Asn His Ile Ile Trp Val Val Thr Arg Asp Ala Asn Pro Lys
        770                 775                 780

Trp Ser Thr Tyr Lys Lys Ala Tyr Glu Asp Ile Glu Arg Ser Gly Leu
785                 790                 795                 800

Cys Ser Asn Tyr
```